(12) United States Patent
Suppes

(10) Patent No.: US 9,404,027 B2
(45) Date of Patent: Aug. 2, 2016

(54) METHOD OF PRODUCING LOWER ALCOHOLS FROM GLYCEROL

(71) Applicant: The Curators of the University of Missouri, Columbia, MO (US)

(72) Inventor: Galen J. Suppes, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 239 days.

(21) Appl. No.: 14/058,653

(22) Filed: Oct. 21, 2013

(65) Prior Publication Data

US 2014/0042358 A1    Feb. 13, 2014

Related U.S. Application Data

(60) Division of application No. 13/595,185, filed on Aug. 27, 2012, now Pat. No. 8,563,783, which is a continuation of application No. 12/340,371, filed on Dec. 19, 2008, now Pat. No. 8,252,961, application (Continued)

(51) Int. Cl.
| | |
|---|---|
| *C07C 27/04* | (2006.01) |
| *C09K 3/18* | (2006.01) |
| *C07C 29/145* | (2006.01) |
| *C07C 29/60* | (2006.01) |
| *C07C 45/52* | (2006.01) |
| *C09K 5/10* | (2006.01) |

(52) U.S. Cl.
CPC ............... *C09K 3/185* (2013.01); *C07C 27/04* (2013.01); *C07C 29/145* (2013.01); *C07C 29/60* (2013.01); *C07C 45/52* (2013.01); *C09K 5/10* (2013.01)

(58) Field of Classification Search
CPC ........................................................ C07C 27/04
USPC ........................................................ 568/861
See application file for complete search history.

(56) References Cited

U.S. PATENT DOCUMENTS

| | | |
|---|---|---|
| 3,871,445 A | 3/1975 | Wanka et al. |
| 4,451,677 A | 5/1984 | Bradley et al. |
| 4,516,632 A | 5/1985 | Swift et al. |
| 4,626,604 A | 12/1986 | Hiles et al. |
| 4,642,394 A | 2/1987 | Che |
| 5,214,219 A | 5/1993 | Casale et al. |

(Continued)

FOREIGN PATENT DOCUMENTS

| | | |
|---|---|---|
| DE | 524 1001 C | 5/1931 |
| DE | 41 28 692 A1 | 3/1993 |

(Continued)

OTHER PUBLICATIONS

U.S. Appl. No. 11/088,603 Office Action mailed Feb. 18, 2009; 9 pages.

(Continued)

*Primary Examiner* — Elvis O Price
(74) *Attorney, Agent, or Firm* — Thompson Coburn LLP

(57) ABSTRACT

A reactive-separation process converts glycerin into lower alcohols, having boiling points less than 200° C., at high yields. Conversion of natural glycerin to propylene glycol through an acetol intermediate is achieved at temperatures from 150° to 250° C. at pressures from 1 and 25 bar. The preferred applications of the propylene glycol are as an antifreeze, deicing compound, or anti-icing compound. The preferred catalyst for this process in a copper-chromium.

11 Claims, 17 Drawing Sheets

Related U.S. Application Data

No. 14/058,653, which is a continuation-in-part of application No. 12/278,634, filed as application No. PCT/US2006/042707 on Oct. 31, 2006, now abandoned, said application No. 12/340,371 is a continuation-in-part of application No. 11/510,992, filed on Aug. 28, 2006, now Pat. No. 8,017,816, said application No. 12/340,371 is a continuation-in-part of application No. 11/088,603, filed on Mar. 24, 2005, now Pat. No. 7,663,004, said application No. 11/510,992 is a continuation-in-part of application No. 11/088,603, and a continuation-in-part of application No. 10/420,047, filed on Apr. 21, 2003, now abandoned.

(60) Provisional application No. 61/008,334, filed on Dec. 19, 2007, provisional application No. 60/731,673, filed on Oct. 31, 2005, provisional application No. 60/556,334, filed on Mar. 25, 2004, provisional application No. 60/374,292, filed on Apr. 22, 2002, provisional application No. 60/410,324, filed on Sep. 13, 2002.

(56) References Cited

U.S. PATENT DOCUMENTS

| | | | |
|---|---|---|---|
| 5,254,758 | A | 10/1993 | Hiles et al. |
| 5,266,181 | A | 11/1993 | Matsumura et al. |
| 5,276,181 | A | 1/1994 | Casale et al. |
| 5,426,249 | A | 6/1995 | Haas et al. |
| 5,616,817 | A | 4/1997 | Schuster et al. |
| 5,811,597 | A | 9/1998 | Hwan et al. |
| 6,080,898 | A | 6/2000 | Drent et al. |
| 6,488,742 | B1 | 12/2002 | Grunewald et al. |
| 2002/0077501 | A1 | 6/2002 | Hoyme et al. |
| 2005/0244312 | A1 | 11/2005 | Suppes et al. |
| 2007/0287865 | A1 | 12/2007 | Arredondo et al. |

FOREIGN PATENT DOCUMENTS

| | | |
|---|---|---|
| DE | 4302464 A1 | 8/1994 |
| EP | 0523 015 A | 1/1993 |
| EP | 0523014 A2 | 1/1993 |
| EP | 0544 157 | 6/1993 |
| EP | 0713849 A1 | 5/1996 |
| EP | 0 826 691 A | 3/1998 |
| GB | 490 211 | 8/1938 |
| JP | 2002 265986 | 9/2002 |
| WO | WO 93/05006 | 3/1993 |
| WO | WO 01/46102 | 6/2001 |
| WO | WO 01/66499 | 9/2001 |
| WO | WO 03/087041 | 10/2003 |
| WO | WO2005/095536 A2 | 10/2005 |
| WO | WO2007/0537050 | 5/2007 |

OTHER PUBLICATIONS

U.S. Appl. No. 11/088,603 Response to Office Action filed Aug. 18, 2009; 12 pages.
U.S. Appl. No. 11/088,603 Examiner Interview Summary and Notice of Allowance dated Sep. 29, 2009, 7 pages.
U.S. Appl. No. 12/645,213, Notice of Allowance mailed Jun. 14, 2010, 6 pages.
U.S. Appl. No. 11/510,992, Restriction Requirement mailed Mar. 15, 2010, 6 pages.
U.S. Appl. No. 11/510,992, Restriction Requirement filed Apr. 15, 2010, 14 pages.
U.S. Appl. No. 11/510,992, Notice of noncompliant response mailed Apr. 29, 2010, 2 pages.
PCT/US06/042707 International Search Report and Written Opinion; mailed Apr. 7 2007; 16 pages.
U.S. Appl. No. 11/510,992, Response to Notice of noncompliant response filed Apr. 29, 2010, 14 pages.
U.S. Appl. No. 10/420,047 Selected pages of Image File Wrapper dated Apr. 21, 2003 through May 27, 2005; 57 pages.
U.S. Appl. No. 11/088,603 Office Action mailed Jul. 24, 2008; 12 pages.
U.S. Appl. No. 11/088,603 Response to Office Action filed Oct. 24, 2008; 10 pages.
Dasari, M.A., et al.: "Low-Pressure Hydrogenolysis of Glycerol to Propylene Glycol," Applied Catalysis A: General, Elsevier Science, Amsterdam, Netherlands, vol. 281, No. 1-2, p. 225-231, Jan. 1, 2005.
International Search Report and Written Opinion for PCT/US2005/009901, Jan. 19, 2006.
Montassier, C. et al.; Polyol Conversion by Liquid Phase Heterogeneous Catalysis Over Metals; 1998 Elsevier Science Publishers B.V., Amsterdam; pp. 165-170.
Montassier, C., et al.: "Deactivation of Supported Copper Based Catalysts During Polyol Conversion in Aqueous Phase" Applied Catalysis A: General, Elsevier Science, Amsterdam, Netherlands, vol. 121, No. 2, p. 231-244, Jan. 19, 1995.
Montassier, C., et al.: "Polyol Conversion by Liquid Phase Heterogeneous Catalysis Over Metals," Heterogeneous Catalysis and Fine Chemicals, p. 165-170, 1988.
PCT/US05/009901 International Preliminary Report on Patentability, Sep. 26, 2006; 21 pages.
PCT/US2008/087842 International Search Report & Written Opinion mailed Mar. 5, 2009, 14 pages.
ITSUNO, "Organic Reactions" 1998, 1 page.
European Application No. 06836781.2, Communication Pursuant to Article 94(3) EPC dated Apr. 20, 2010, 8 pages.
European Application No. 05726117.4, Communication Pursuant to Article 94(3) EPC dated Jan. 12, 2010, 5 pages.
European Application No. 05726117.4, Response to Communication filed Jul. 22, 2010, 24 pages.
European Application No. 05726117; Examination Report dated Apr. 16, 2007; 3 pages.
European Application No. 05726117; Response to Examination Report dated Oct. 26, 2007; 5 pages.
Office Action received in related U.S. Appl. No. 12/278,634, dated Jul. 19, 2013, 22 pages.
File History in related U.S. Appl. No. 13/595,185.

METHOD OF PRODUCING LOWER ALCOHOLS FROM GLYCEROL

RELATED APPLICATIONS

This application is a divisional of U.S. application Ser. No. 13/595,185, filed Aug. 27, 2012 which is a continuation of U.S. application Ser. No. 12/340,371 filed Dec. 19, 2008 which claims benefit of priority to U.S. Provisional Application Ser. No. 61/008,334 filed Dec. 19, 2007. This application is a continuation-in-part of U.S. application Ser. No. 12/278,634 filed Aug. 7, 2008, which is a national phase entry under 35 U.S.C. §371 of PCT application no. PCT/US2006/042707 filed Oct. 31, 2006, which claims benefit of priority to U.S. Provisional Application Ser. No. 60/731,673 filed Oct. 31, 2005. U.S. application Ser. No. 12/340,371 is also a continuation-in-part of U.S. application Ser. No. 11/510,992 filed Aug. 28, 2006, which claims benefit of priority to U.S. Provisional Application Ser. No. 60/731,673 filed Oct. 31, 2005. U.S. application Ser. Nos. 12/340,371 and 11/510,992 are continuation-in-parts of U.S. application Ser. No. 11/088,603 filed Mar. 24, 2005. U.S. application Ser. No. 11/008,603 claims benefit of priority to U.S. Provisional Application Ser. No. 60/556,334 filed Mar. 25, 2004 and is a continuation-in-part of U.S. patent application Ser. No. 10/420,047 filed Apr. 21, 2003, which claims benefit of priority to U.S. Provisional Patent Application Ser. Nos. 60/374,292, filed Apr. 22, 2002 and 60/410,324, filed Sep. 13, 2002. All of the above-listed applications are incorporated by reference in their entirety herein.

BACKGROUND

1. Field of the Invention

This invention relates generally to a process for value-added processing of fats and oils to yield glycerol and glycerol derivatives. More particularly, the process converts glycerol to acetol and then acetol to propylene glycol (PG) to produce a propylene glycol with ultra-low amounts of ethylene glycol (EG). The process may yield glycerol-based products and glycerol derivatives, such as antifreeze and other products.

2. Description of the Related Art

Existing processes for the hydrogenation of glycerol to form other products are generally characterized by requirements for excessively high temperatures and pressures. For example, high temperatures may degrade the reaction products. Working pressures of several hundred bar create safety concerns and increase the capital costs of implementing these processes. Most of such processes yield substantial impurities that may necessitate costly purification steps to isolate the desired reaction products.

In one example, conventional processing of natural glycerol to propanediols uses a catalyst, for example, as reported in U.S. Pat. Nos. 5,616,817, 4,642,394, 5,214,219 and 5,276,181. These patents report the successful hydrogenation of glycerol to form propanediols. None of the processes shown by these patents provide a direct reaction product mixture that is suitable for use as antifreeze. None provide process conditions and reactions that suitably optimize the resultant reaction product mixture for direct use as antifreeze. None address the use of unrefined crude natural glycerol feed stock, and none of these processes are based on reactive distillation. Generally, existing processes U.S. Pat. No. 5,616,817 issued to Schuster et al. describes the catalytic hydrogenation of glycerol to produce propylene glycol in high yield, such as a 92% yield, with associated formation of n-propanol and lower alcohols. Conversion of glycerol is substantially complete using a mixed catalyst of cobalt, copper, manganese, and molybdenum. Hydrogenation conditions include a pressure of from 100 to 700 bar and a temperature ranging from 180° C. to 270° C. Preferred process conditions include a pressure of from 200 to 325 bar and a temperature of from 200° C. to 250° C. This is because Schuster et al. determined that lower pressures lead to incomplete reactions, and the higher pressures increasingly form short chain alcohols. A crude glycerol feed may be used, such as is obtainable from the transesterification of fats and oils, but needs to be refined by short path distillation to remove contaminants, such as sulfuric acid that is commonly utilized in the transesterification process. The feed should contain glycerol in high purity with not more than 20% water by weight.

U.S. Pat. No. 4,642,394 issued to Che et al. describes a process for catalytic hydrogenation of glycerol using a catalyst that contains tungsten and a Group VIII metal. Process conditions include a pressure ranging from 100 psi to 15,000 psi and a temperature ranging from 75° C. to 250° C. Preferred process conditions include a temperature ranging from 100° C. to 200° C. and a pressure ranging from 200 to 10,000 psi. The reaction uses basic reaction conditions, such as may be provided by an amine or amide solvent, a metal hydroxide, a metal carbonate, or a quaternary ammonium compound. The concentration of solvent may be from 5 to 100 ml solvent per gram of glycerol. Carbon monoxide is used to stabilize and activate the catalyst. The working examples show that process yields may be altered by using different catalysts, for example, where the yield of propanediols may be adjusted from 0% to 36% based upon the reported weight of glycerol reagent.

U.S. Pat. No. 5,214,219 issued to Casale, et al. and U.S. Pat. No. 5,266,181 issued to Matsumura, et al. describe the catalytic hydrogenation of glycerol using a copper/zinc catalyst. Process conditions include a pressure ranging from 5 MPa to 20 MPa and a temperature greater than 200° C. Preferred process conditions include a pressure ranging from 10 to 15 MPa and a temperature ranging from 220° C. to 280° C. The concentration of glycerol may range from 20% to 60% by weight in water or alcohol, and this is preferably from 30% to 40% by weight. The reaction may be adjusted to produce significant amounts of hydrocarbon gas and/or lactic acid, such that gas generation is high when lactic acid formation is low and lactic acid formation is high when gas generation is low. This difference is a function of the amount of base, i.e., sodium hydroxide, which is added to the solvent. Alcohol reaction products may range from 0% to 13% of hydrocarbon products in the reaction mixture by molar percentages, and propanediols from 27% to 80%. Glycerol conversion efficiency exists within a range from 6% to 100%.

SUMMARY

The presently disclosed instrumentalities advance the art and overcome the problems outlined above by producing value-added products in exceptionally high yield and purity from hydrogenation of natural glycerol feed stocks. The presently disclosed instrumentalities also advance the art by producing propylene glycol with ultra-low amounts of ethylene glycol from renewable feed stocks. In the process of overcoming these problems, the energy costs are also reduced. In other aspects, the disclosure pertains to the manufacture of products that do not require exceptionally high yield and purity, such as antifreeze.

In one aspect, a process for converting glycerol to acetol with high selectivity, commences with providing a glycerol-containing material that has 50% or less by weight water. This material may be, for example, a byproduct of biodiesel manufacture. The glycerol-containing material is contacted with a catalyst that is capable of hydrogenating glycerol, in order to form a reaction mixture. Conditions for reaction of the reaction mixture are established to include a temperature within a range from 150° C. to 250° C. and a pressure within a range from 0.1 bar to 25 bar. The reaction mixture is reacted under the conditions for reaction to dehydrate the glycerol with resultant formation of acetol as a reaction product. The reaction may be performed at temperatures of up to 270° C., 280° C. or even 290° C.; however, the use of these increased temperature results in thermal degradation of the reaction product together with die-reactions, and so is not recommended for applications where high purity of the reaction product is required. It is possible by use of this process according to one or more of the embodiments described below to achieve, for example, propylene glycol that is 90% pr even 98% pure at a high yield of better than 85% or even 95%.

In various other aspects, the glycerol-containing feedstock preferably contains from 5% to 15% water by weight. The catalyst may be a heterogenous catalyst that contains at least one element from Groups I or VIII of the Periodic Table. The catalyst may be a heterogeneous catalyst including at least one material selected from the group consisting of palladium, nickel, rhodium, copper, zinc, chromium and combinations thereof. The dehydration catalyst may, for example, contain from 5 wt % to 95 wt % chromium, and may be comprised of compositions of copper expressed as CuO and chromium expressed as $Cr_2O_3$ at 30-80 wt % of CuO and 20-60 wt % of $Cr_2O_3$. In one example, the catalyst may be expressed as $Cr_2O_3$ at 40-60 wt % of CuO and 40-50 wt % of $Cr_2O_3$. The presence of hydrogen reduces these oxides with their reduced form which is the active form of the catalyst for hydrogenation of acetol.

A small amount of hydrogen may be added to deter the acetol reaction product during formation from scavenging hydrogen from other hydrocarbon materials in the reaction mixture. If acetol is the desired final product, the partial pressure of hydrogen may be sufficiently low, such as about 0.1 bar, to prevent substantial conversion of acetol to propylene glycol.

A greater amount of hydrogen may be added to facilitate conversion of the acetol to other products. Where hydrogen is added under the foregoing reaction conditions, the dominant product is suitably propylene glycol.

It is possible to use a gas flow for stripping the reaction products from the reaction mixture, where such reaction product may include acetol and propylene glycol. In one embodiment, the glycerol-containing material is in liquid phase and the process entails removing the reaction product(s) during the step of reacting. This may be done by facilitating selective release of acetol as vapor from the reaction mixture by action of partial pressure through contact with a gas, such as nitrogen or a noble gas, that is essentially inert to the reaction mixture and the acetol reaction product.

The acetol may be condensed and further reacted to form downstream products, such as by reaction with hydrogen to produce propylene glycol or lactaldehyde. A condenser for this purpose suitably operates at a temperature between 25° C. and 150° C., or more preferably from 25° C. to 60° C. One process for converting acetol to propylene glycol with high selectivity entails contacting an acetol-containing feedstock that contains less than 50% by weight water with a catalyst that is capable of hydrogenating acetol to form a reaction mixture; and heating the reaction mixture to a temperature between 50° to 250° C. at a pressure between 1 and 500 bar to form propylene glycol.

In another embodiment, the gas that strips reaction [products from the initial reaction mixture may be reactive with the acetol reaction product, such as hydrogen gas is reactive with the acetol. Accordingly, the stripper gas may be supplemented with hydrogen for this effect, such that a different reaction product is condensed. This different reaction product may be propylene glycol. Unused hydrogen may be recycled from the condenser back to the reactor vessel.

A more preferred temperature range for facilitating the reaction is from 180° C. to 220° C. A more preferred pressure range is from 1 to 20 bar, where low pressures of from 1 to 15 bar and 1 to 5 bar may yield especially pure products. The reaction may persist for a duration in a slurry phase with reaction limited by catalyst within a range from 0.1 hour to 96 hours, such as from 4 to 46 hours or from 4 to 28 hours. It is possible to operate the reaction at higher catalyst loadings and even in a gas phase with much shorter reaction times within the range from 0.001 to 8 hours, or more-preferably 0.002 to 1 hour, or even more preferably from 0.05 to 0.5 hours.

In another embodiment, the reaction does not require a glycerol feed, but may be a polyhydric material, such as a three-carbon or greater sugar or polysaccharide. The process equipment in use on these materials may form an alcohol product having a boiling point less than 200° C.

Batch reactor effluent may be used as an antifreeze, anti-icing agent or de-icing agent, for example, as may be obtained from the crude glycerol byproduct of the C1 to C4 alkyl alcohol alcoholysis of a glyceride. An alternative glycerol source is the crude from hydrolysis of a glyceride. Such materials as this may contain, on a water-free basis, from about 0.5% to about 60% glycerol, and from about 20% to about 85% propylene glycol. Another such composition may contain, on a water-free basis, from about 10% to about 35% glycerol, from about 40% to about 75% propylene glycol, and from about 0.2% to about 10% C1 to C4 alkyl alcohol. The compositions may also contain from about 1% to 15% residue by-product from a reaction of glycerol.

In one embodiment, a process for producing antifreeze from a crude glycerol byproduct of a $C_1$ to $C_4$ alkyl alcohol alcoholysis of a glyceride, entails neutralizing the crude glycerol to achieve a pH between 5 and 12. This is followed by separating $C_1$ to $C_4$ alcohol and water from the crude glycerol such that the combined concentrations of water and $C_1$ to $C_4$ alcohols is less than about 5(wt) %. The separated crude glycerol is contacted with a hydrogenation catalyst and hydrogen at a pressure of between about 0.1 and 200 bar and at a temperature between about 100° C. and 280° C. for a period of time sufficient to achieve a conversion of the glycerol of between 60 and 90% on the basis of glycerol in the crude glycerol. The pressure is more preferably within a range from 0.1 to 25 bar and is even more preferably from 1 to 20 bar. Separation of $C_1$ to $C_4$ alcohols and water may be achieved by flash separation at a temperature greater than about 60° C., or by thermal diffusion. The hydrogenation catalyst may contain at least one metal from the group consisting of palladium, nickel, zinc, copper, platinum, rhodium, chromium, and ruthenium.

A gas phase reaction may be performed for converting glycerol to a product at high selectivity to propylene glycol and low selectivity to ethylene glycol. The reaction commences with providing a gas phase reaction mixture that is essentially free of liquid and contains: glycerol with a partial pressure of glycerol in a range from 0.01 bars and 0.5 bars of glycerol, and hydrogen with a partial pressure of hydrogen between 0.01 and 25 bars of hydrogen. The reaction mixture is maintained at a total pressure between 0.02 and 25 bars and contacts a heterogeneous catalyst at a temperature between 150° C. and 280° C. to form propylene glycol.

In the gas phase reaction, a partial pressure of glycerol is preferably less than glycerol's dew point partial pressure in the reaction mixture, and greater than one fourth the dew point partial pressure in the reaction mixture. This partial pressure is also preferably greater than half the dew point partial pressure in the reaction mixture. The gas phase reaction mixture contains essentially no liquid and has a partial pressure of glycerol between 0.01 and 0.5 bars of glycerol and a partial pressure of hydrogen between 0.01 and 5 bars of hydrogen; and the reaction may be performed at a temperature between 150° C. and 280° C. to facilitate a reaction by use of the same catalysts described above. The total pressure of reaction may be between 0.02 and 5 bars.

The process may be tuned to produce increased amounts of lactaldehyde with high selectivity. This is done by combining a glycerol-containing feedstock with less than 50% by weight water with a catalyst that is capable of dehydrating glycerol to form a reaction mixture; and heating the reaction mixture to a temperature between 150° to 200° C. at a pressure between 0.01 and 25 bar. A preferred temperature range for this reaction is from 165° C. to 185° C., while the pressure exists within a range from 0.02 to 2 bars. The lactaldehyde condenser may operate at a temperature between 0° C. to 140° C.

The propylene glycol product may be produced in high purity. especially from the gas-phase reaction. The propylene glycol reaction product may be further purified by adding a base to the said propylene glycol product to achieve a pH greater than 8.0 and distilling the propylene glycol from the product having a pH greater than 8.0. The base may be selected from the group comprised of sodium hydroxide, potassium hydroxide, and calcium oxide.

Although a batch reactor is preferred, other suitable reactor types include slurry batch reactors, trickle bed reactors, and teabag reactors. One reactor for use with highly exothermic reactions comprised of an outer shell containing U-tubes with an orientation such that the U-end of the U-Tubes is facing upward. The shell has an upper removable head where catalyst is loaded between shell and tubes from the top by removing the upper head. An inert packing may be is placed in the lowest portion of the space between the shell and U-Tubes at a depth between 2 and 24 inches In another aspect of the present disclosure, an improved process containing at least one separation step for converting glycerol to acetol with high selectivity is provided. This PG producing process with one or more separation steps ("the improved process" hereinafter) may comprise the steps of: (a) contacting a glycerol-containing material with a catalyst that is capable of hydrogenating glycerol, in order to form a reaction mixture; (b) reacting the reaction mixture under a first condition for reaction to dehydrate the glycerol with resultant formation of acetol as a main component of a first reaction product, said first condition including a temperature within a range from 150° C. to 250° C. and a pressure within a range from 0.02 bar to 25 bar; (c) separating the acetol formed in step (b) from other components in the first reaction product; and (d) reacting the separated acetol from step (c) to form a second reaction product.

The second reaction product preferably comprises propylene glycol. In one aspect, more than 50% (w/w) of the second reaction product is propylene glycol. In another aspect, more than 80% (w/w) of the second reaction product is propylene glycol.

In another embodiment, the first condition of the improved process is in favor of formation of acetol. In one aspect, the first condition includes a temperature within a range from 190° C. to 250° C. More preferably, the first condition includes a temperature within a range from 200° C. to 230° C. In another aspect, the first condition includes a pressure within a range from 0.05 bar to 1.2 bar. More preferably, the first condition includes a pressure within a range from 0.1 bar to 0.3 bar. The molar ratio between different reactants also play an important role in the yield, efficiency and quality of the reaction. In one aspect, the molar ratio of hydrogen to glycerol for the first condition is about 0.1.

In another embodiment, step (d) of the improved process is performed under a second condition that is in favor of formation of propylene glycol. In one aspect, the second condition includes a temperature within a range from 140° C. to 220° C. More preferably, the second condition includes a temperature within a range from 160° C. to 200° C. In another aspect, the second condition includes a pressure within a range from 1.2 bar to 500 bar. More preferably, the second condition includes a pressure within a range from 2 bar to 30 bar. In yet another aspect, the molar ratio of hydrogen to glycerol for the second condition is between 1 to 1000. More preferably, the molar ratio of hydrogen to glycerol is between 1.2 to 15.

During step (c) of the improved process, acetol may be substantially separated from at least one component selected from the group consisting of ethylene glycol and propylene glycol. Thus, the acetol that is subsequently subjected to the reaction of step (d) is substantially free from ethylene glycol. Preferably, at least 70% by weight of ethylene glycol present in the first reaction product is removed from the acetol before the acetol is further converted to PG. More preferably, at least 90% by weight of ethylene glycol present in the first reaction product is removed from the acetol.

In another aspect of the improved process, the acetol in the first reaction product is substantially separated from hydrogen and water in step (c). The separated hydrogen and water may be recycled and reused in the process.

The improved process may further comprise a step (e) wherein the second reaction product is separated from other components present in the second reaction product. Preferably, acetol is substantially separated from propylene glycol in step (e) to obtain a relatively pure final PG product.

DETAILED DESCRIPTION

There will now be shown and described by way of non-limiting example a process for producing lower alcohols from glycerol feed stock to provide glycerol-based and/or propylene glycol-based antifreezes. The lower alcohols include, for example, as acetol and propylene glycol. Preferred uses of reaction product mixtures that are derived from the process include but are not limited to deicing fluids, anti-icing fluids, and antifreeze applications. These uses of the glycerol-based and/or propylene glycol-based antifreezes displace the use of toxic and non-renewable ethylene glycol with non-toxic and renewable glycerol-derived antifreeze. In this regard, use of propylene glycol that is derived from natural glycerol is a renewable alternative to petroleum-derived propylene glycol. Other downstream uses for propylene glycol include any substitution or replacement of ethylene glycol or glycerol with propylene glycol.

Equipment for Reactive-Separation Preparation of Antifreeze from Poly-Alcohols Like Glycerol One method of preparing antifreeze from glycerol includes reaction at a temperature ranging from 150° to 250° C. and in some embodiments this temperature is more preferably from 180° C. to 220° C. The reaction occurs in a reaction vessel. The pressures in the reaction vessel are preferably from 1 to 25 bars and in some embodiments this pressure is more-preferably between 5 and 18 bars. The process equipment may include, for example, a reactor at these temperature and pressure conditions connected to a condenser and condensate tank where the condenser is preferably at a temperature between about 25° C. and 150° C. and in some embodiments this is more preferably between 25° and 60° C.

Figure 1:
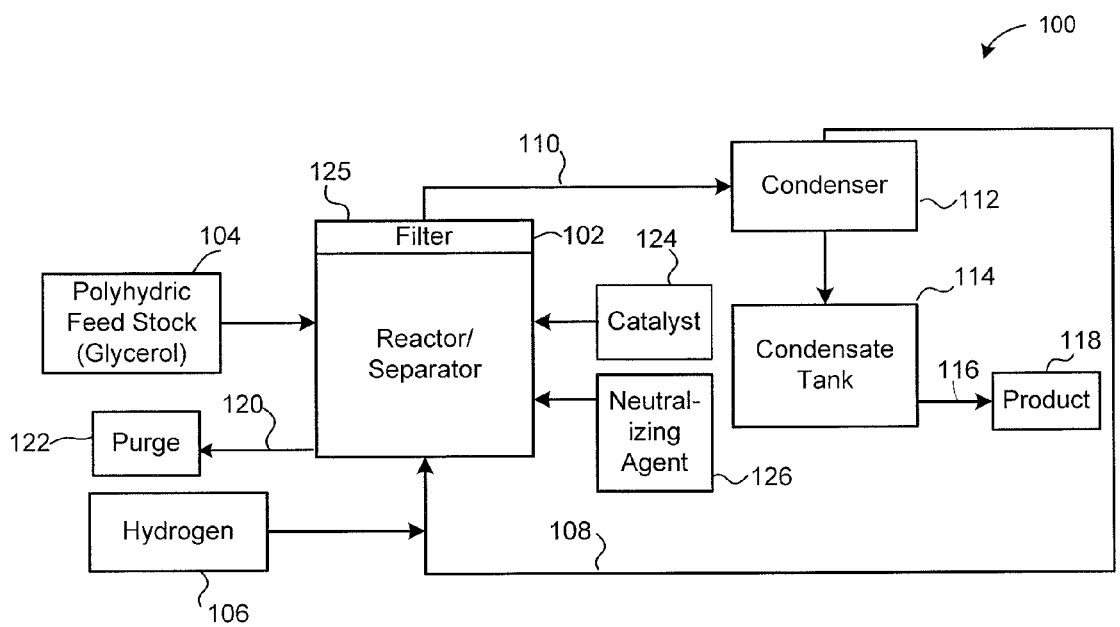
FIG. 1 is a schematic block flow diagram illustrating preferred reactor-separator with a reactor, condenser, and condensate tank, and recycle of unreacted hydrogen.

FIG. 1 provides a block flow diagram of process equipment 100 including a reactor-separator 102. A polyhydric feed stock 104, for example, containing glycerol, is introduced stepwise or continuously into the reactor separator 102. Hydrogen 106 is added to hydrogen line 108 to promote conversion of glycerol 104 to propylene glycol within the reactor-separator 102. The process temperatures are such that a distillation occurs with the formation or presence of propylene glycol, short chain alcohols, and water, which vaporize and flow through overhead line 110 to a condenser 112. Most of the alcohol, water and propylene glycol vapors condense in the condenser 112 and are collected in the condensate tank 114 for discharge through discharge line 116 as product 118. Unreacted hydrogen and remaining vapors from the condenser 112 are recycled back to the reactor-separator 102 through the hydrogen recycle line 108.

Reaction products 118 are removed from the condensate tank 112 through discharge line 116, and the reaction mixture inside reactor-separator 102 may be purged periodically or at a slow flow rate through purge line 120 to obtain purge mixture 122. Purging is necessary or desirable when non-volatile reaction by-products are formed and when metals or inorganic acids, such as residual biodiesel catalysts, are present in the polyhydric feed stock 104. Catalysts and useful components, such as glycerol and propylene glycol, are preferably recovered from the purge mixture 122.

The reaction inside reactor-separator 102 is catalyzed, and may be facilitated at periodic intervals or by the continuous introduction of a suitable catalyst 124, which may be any catalyst that is suitable for use in converting glycerol into lower alcohols, such as acetol and/or propylene glycol. The catalyst 124 may reside within the reactor-separator as a packed bed, or distribution of the catalyst 124 inside reactor-separator 102 may be improved by using the hydrogen gas 108 to provide a fluidized bed, or by stirring (not shown). Agitated slurry reactors of a liquid phase reaction with a vapor overhead product are preferred. The catalyst 124 is mixed with the polyhydric feedstock 104 that is undergoing reaction in the reactor separator 102 to facilitate breaking of carbon-oxygen or carbon-carbon bonds including but not limited to hydrogenation. As used herein, hydrogenolysis and hydrogenation are interchangeable terms.

By way of example the reaction of glycerol with hydrogen to form propylene glycol and water is referred to frequently as hydrogenation in this text. Suitable catalysts for this purpose may include, without limitation, such metals as platinum, palladium, ruthenium, chromium, nickel, copper, zinc, rhodium, chromium, ruthenium, and combinations thereof. Catalysts may be deposited on a substrate, such as an alumina substrate. In a broader sense, suitable catalysts may include those catalyst containing one or more elements of the subgroups from Group I, Group VI, and/or Group VIII of the Periodic Table. The best catalysts are non-volatile, and are preferably prevented from exiting the reactor separator 102 into the condensate tank 114. A filter 125 in the overhead discharge line 110 from the reactor separator 102 retains solid catalysts in the reactor separator 102. No limitations are placed or implied on whether the catalyst is soluble or solid, the oxidative state of the catalyst, or the use of solid supports or soluble chelates.

Reaction times at preferred conditions may range from a few minutes to 96 hours. Reaction time may be defined as the volume of liquid in the reactor divided by the time-averaged flow rate of liquids into the reactor. While the preferred reaction times are greater than 2 hours, the average residence time at higher loadings of catalyst 124 can be less than an hour and typically longer than 0.5 hours. While preferred temperatures are up to 250° C., the reactor-separator may be operated at temperatures up to 270° C. with satisfactory results.

The polyhydric feed stock 104 preferably contains glycerol. In a broader sense, polyhydric feedstock 104 may contain, for example, from 5% to substantially 100% of a polyol, for example, glycerol, sorbitol, 6-carbon sugars, 12-carbon sugars, starches and/or cellulose.

Figure 2:
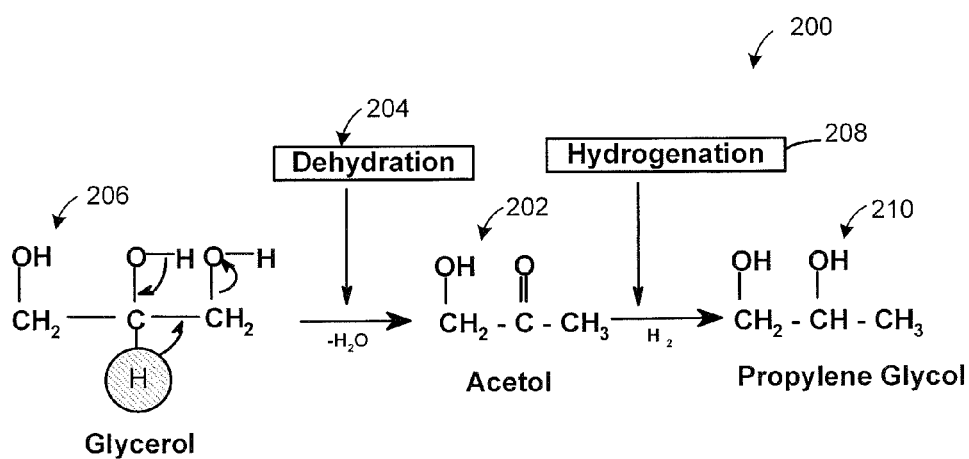
FIG. 2 is a schematic of the disclosed reaction mechanism for conversion of glycerol to propylene glycol via acetol intermediate.
Figure 3:
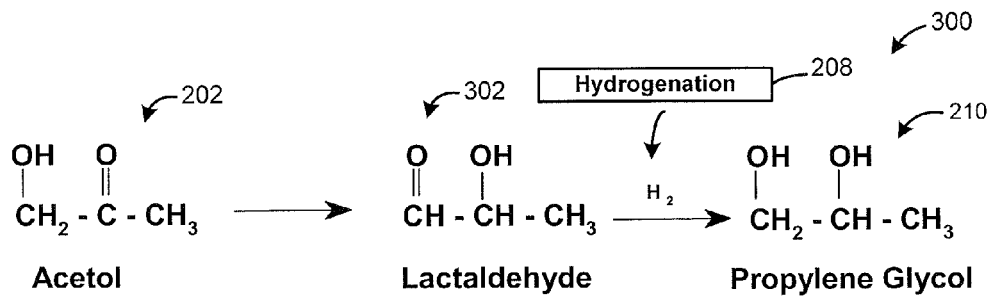
FIG. 3 is a schematic of the disclosed reaction mechanism for conversion of acetol to propylene glycol via lactaldehyde intermediate.

As illustrated in FIG. 1, the process equipment 100 is preferably configured to provide hydrogen 106 as a reagent; however, the use of hydrogen is optional. Commercially valuable products may be formed as intermediates that collect in the condensate tank in the absence of hydrogen. Accordingly, use of hydrogen 106 is preferred, but not necessary. For example, the intermediates collecting in condensate tank 114 may include acetol (hydroxy-2-propanone), which may be subjected to hydrogenolysis by at least two mechanisms as shown in FIGS. 2 and 3. In addition to reagents, the material within reactor separator 102 may contain water, salts, or catalysts residue from previous processes.

One type of polyhydric feedstock 104 may contain glycerol that is prepared by transesterification of oils or fatty acids, for example, as described in co-pending application Ser. No. 10/420,047 filed Apr. 23, 2003, which is incorporated by reference to the same extent as though fully replicated herein. In a polyhydric feedstock 104 of this type, water may be present in an amount ranging from 0% to 70%. More preferably, water is present in an amount ranging from 5% to 15%. Water may be added to reduce side-reactions, such as the formation of oligomers.

One advantage of using the process equipment 100 is that volatile alcohol products are removed from the reaction mixture as they are formed inside reactor separator 102. The possibility of degrading these products by continuing exposure to the reaction conditions is commensurately decreased by virtue of this removal. In addition, the volatile reaction products are inherently removed from the catalysts to provide relatively clean products. This reaction-separation technique is especially advantageous for catalysts that are soluble with or emulsified in the reaction mixture.

A preferred class of catalyst 124 is the copper chromite catalyst, $(CuO)_x (Cr2O3)_y$. This type of catalyst is useful in the process and is generally available commercially. In this class of catalyst, the nominal compositions of copper expressed as CuO and chromium expressed as $Cr_2O_3$ may vary from about 30-80 wt % of CuO and 20-60 wt % of $Cr_2O_3$. Catalyst compositions containing about 40-60 wt % copper and 40-50 wt % of chromium are preferred.

Preferred catalysts for use as catalyst 124, in addition to the copper and chromium previously described, also include barium oxide and manganese oxide or any of their combinations. Use of barium and manganese is known to increase the stability of the catalyst, i.e., the effective catalyst life. The nominal compositions for barium expressed as barium oxide can vary 0-20 wt % and that for manganese expressed as manganese oxide can vary from 0-10 wt %. The most preferred catalyst compositions comprise from 40%-60 wt % of CuO 40-55 wt % of $Cr_2O_3$, 0-10 wt % of barium oxide and 0-5 wt % manganese oxide.

Reaction Mechanism

According to one mechanism proposed by Montassier et al. (1988), dehydrogenation of glycerol on copper can form glyceric aldehyde in equilibrium with its enolic tautomer. The formation of propylene glycol was explained by a nucleophilic reaction of water or adsorbed OH species, a dehydroxylation reaction, followed by hydrogenation of the intermediate unsaturated aldehyde. This reaction mechanism was observed not to apply in our investigation.

FIG. 2 shows a preferred reaction mechanism 200 for use in the reactor-separator 102 of FIG. 1, and for which process conditions may be suitably adjusted as described above. As shown in FIG. 2, hydroxyacetone (acetol) 202 is formed, and this is possibly an intermediate of an alternative path for forming propylene glycol by a different mechanism. The acetol 202 is formed by dehydration 204 of a glycerol molecule 206 that undergoes intramolecular rearrangements as shown. In a subsequent hydrogenation step 208, the acetol 202 further reacts with hydrogen to form propylene glycol 210 with one mole of water by-product resulting from the dehydration step 204.

Early studies to investigate the effect of water on the hydrogenolysis reaction indicated that the reaction takes place even in absence of water with a 49.7% yield of propylene glycol. Moreover, and by way of example, the reaction is facilitated by use of a copper-chromite catalyst, which may be reduced in a stream of hydrogen prior to the reaction. In this case, the incidence of surface hydroxyl species taking part in the reaction is eliminated. The above observations contradict the mechanism proposed by Montassier et al. where water is present in the form of surface hydroxyl species or as a part of reactants.

In another embodiment of the present disclosure, a separation step is included between two reaction steps which result in propylene glycol with ultra-low amount of ethylene glycol. More generally, the embodiment removes efficiently a number of chemicals with boiling points near propylene glycol. Yet another separation step may be included after the second reaction, as illustrated in Example 16. Via this improved process, propylene glycol may be produced with ultra-low amounts of ethylene glycol from renewable feed stocks. Because of the increased efficiency and reuse of intermediated during the process, the cost of energy is also reduced for this improved process as compared to other previously disclosed processes.

The following example provides insight into reaction mechanisms and selectivities that supports the embodiments of this invention, but are not meant to limit the scope of this disclosure.

EXAMPLE 1

Confirmation of Reaction Mechanism

An experiment was performed to validate the reaction mechanism 200. Reactions were conducted in two steps, namely, Steps 1 and 2. In step 1, relatively pure acetol was isolated from glycerol. Temperature ranged from 150° C. to 250° C. and more specifically from 180° C. to 220° C. There was an absence of hydrogen. Pressure ranged from 1 to 14 psi (6.9 MPa to 96 MPa) more specifically from 5 to 10 psi (34 MPa to 69 MPa). A copper-chromite catalyst was present. In Step 2, the acetol formed in Step 1 was further reacted in presence of hydrogen to form propylene glycol at a temperature ranging from 150° C. to 250° C. and more preferably between 180 to 220° C. Excess hydrogen was added at a hydrogen over pressure between 1 to 25 bars using the same catalyst.

It was observed in the Step 2 of converting acetol to propylene glycol that lactaldehyde was formed. Propylene glycol is also formed by the hydrogenation 208 of lactaldehyde 302, as illustrated in FIG. 3. With respect to FIG. 2, lactaldehyde represents an alternative path for forming propylene glycol from acetol. FIG. 3 shows this mechanism 300 where the acetol undergoes a rearrangement of the oxygen double bond to form lactaldehyde 302, but the dehydrogenation step 208 acting upon the lactaldehyde 302 also results in the formation of propylene glycol 210. It was also observed that the formation of lactaldehyde intermediate was predominant at lower reaction temperatures in the range of from 50° C. to 150° C. (see Example 8 below).

The embodiments of this disclosure include production of lactaldehyde. A process for converting glycerol to lactaldehyde with high selectivity preferably includes the steps of combining a glycerol-containing feedstock with less than 50% by weight water with a catalyst that is capable of dehydrating glycerol to form a reaction mixture; and heating the reaction mixture to a temperature between 150° C. to 200° C. over a reaction time interval between 0 to 24 hours at a pressure between 0.02 and 25 bar. Preferably the catalyst used in the step of combining is contains an element of the subgroups from Group I, Group VI, and/or Group VIII of the Periodic Table. Preferably the glycerol-containing feedstock used in the step of combining contains from 0% to 15% water in glycerol by weight. Preferably the catalyst used in the step of combining is a heterogeneous catalyst selected from the group consisting of palladium, nickel, rhodium, copper, zinc, chromium and combinations thereof. Preferably the process includes a step of removing reaction product vapors that form during the step of heating. Preferably the process includes a step of condensing the vapors to yield liquid reaction product. Preferably temperature used in the heating step exists within a range from 165° C. to 185° C. Preferably the pressure used in the heating step exists within a range from 0.02 to 2 bars. Preferably, the step of condensing occurs using a condenser operating at a temperature between 0° C. to 140° C.

This and subsequent reactions were performed in liquid phases with catalyst and sufficient agitation to create a slurry reaction mixture.

EXAMPLE 2

Simultaneous Dehydration and Hydrogenation Using Various Catalysts and Reagent Mixtures A variety of reaction procedures were performed to show that reaction efficiency may be optimized at any process conditions, such as reaction time, temperature, pressure and flash condition by the selection or choice of catalyst for a given polyhydric feedstock.

Table 1 reports the results of reacting glycerol in the presence of hydrogen and catalyst to form a mixture containing propylene glycol. The reaction vessel contained 80 grams of refined glycerol, 20 grams of water, 10 grams of catalyst, and a hydrogen overpressure of 200 psig. The reactor was a closed reactor that was topped off with excess hydrogen. The reaction occurred for 24 hours at a temperature of 200° C. All catalysts used in this Example were purchased on commercial order and used in the condition in which they arrived.

TABLE 1

Summary of catalyst performances based on 80 grams of glycerol reported on a 100 grams basis.

|  | Initial Loading (g) | Best Possible (g) | Catalyst 5% Ruthenium on carbon (g) | Catalyst Raney-Copper (g) | Catalyst Raney-Nickel (g) |
| --- | --- | --- | --- | --- | --- |
| Glycerol | 100 | 0 | 63.2 | 20.6 | 53.6 |
| Water | 25 | 43 | not measured | not measured | not measured |
| Propylene Glycol | 0 | 82 | 14.9 | 27.5 | 14.9 |
| Ethylene Glycol | 0 | 0 | 16.9 | 13.1 | 16.5 |
| Acetol | 0 | 0 | 0.0 | 12.1 | 0.0 |
| Total, excluding water | 100 | 82 | 94.9 | 73.2 | 85.0 |

Table 2 summarizes reaction performance with a higher initial water content, namely, 30 grams of refined glycerol and 70 grams of water. The reactions were conducted at the following initial conditions: 5% wt of catalyst, and a hydrogen overpressure of 1400 kPa. The following table presents compositions after reacting in a closed reactor (with topping off of hydrogen) for 24 hours at a reaction temperature of 200° C.

TABLE 2

Summary of catalyst performances based on 30 grams initial loading of glycerol and 70 grams of water.

|  | Initial Loading (g) | Best Possible (g) | Catalyst 5% Ruthenium on carbon (g) | Catalyst Raney-Copper (g) | Catalyst Raney-Nickel (g) |
| --- | --- | --- | --- | --- | --- |
| Glycerol | 30 | 0 | 20.8 | 19.1 | 3.8 |
| Propylene Glycol | 0 | 24 | 9.3 | 7.23 | 3.1 |
| Ethylene Glycol | 0 | 0 | 0 | 0 | 0 |
| Acetol | 0 | 0 | 1.5 | 1.6 | 1.7 |

Table 3 summarizes the performance of a copper chromium catalyst in the presence of 20 percent of water. The reactions were conducted at the following initial conditions: 5% wt of catalyst, and a hydrogen overpressure of 1400 kPa. The following table presents compositions after reacting in a closed reactor (with topping off of hydrogen) for 24 hours at a reaction temperature of 200° C.

TABLE 3

Summary of copper chromium catalyst performance based on 80 grams initial loading of glycerol and 20 grams of water.

|  | Initial Loading (g) | Best Possible (g) | Catalyst Copper Chromium (g) |
|---|---|---|---|
| Glycerol | 80 | 0 | 33.1 |
| Propylene glycol | 0 | 66.1 | 44.8 |
| Ethylene Glycol | 0 | 0 | 0 |
| Acetol | 0 | 0 | 3.2 |

Table 4 summarizes the impact of initial water content in the reactants on formation of propylene glycol from glycerol. The reactions were conducted at the following initial conditions: 5% wt of catalyst, and a hydrogen overpressure of 1400 kPa. The catalyst was purchased from Sud-Chemie as a powder catalyst having 30 m$^2$/g surface area, 45% CuO, 47% $Cr_2O_3$, 3.5% $MnO_2$ and 2.7% BaO. The following table presents compositions after reacting in a closed reactor (with topping off of hydrogen) for 24 hours at a reaction temperature of 200° C.

TABLE 4

Summary of catalyst performances based on different initial loadings of glycerol in water.

| Water (wt %) | % Conversion | % Yield | % Selectivity |
|---|---|---|---|
| 80 | 33.5 | 21.7 | 64.8 |
| 40 | 48 | 28.5 | 59.4 |
| 20 | 54.8 | 46.6 | 85.0 |
| 10 | 58.8 | 47.2 | 80.3 |
| 0 | 69.1 | 49.7 | 71.9 |

The reaction was performed using a small scale reaction distillation system like that shown as process equipment 100 in FIG. 1 to process a reaction mixture including 46.5 grams of refined glycerol and 53.5 grams water. The catalyst was purchased from Sud-Chemie as a powder catalyst having 30 m$^2$/g surface area, 45% CuO, 47% $Cr_2O_3$, 3.5% $MnO_2$ and 2.7% BaO. Table 5 summarizes performance with higher initial water content using a small reaction distillation system.

TABLE 5

Example of reaction distillation.

|  | Reactor | Distillate |
|---|---|---|
| Glycerol | 21.6 grams | 2.2 |
| Propane Diol | 6.4 | 9.5 |
| Ethylene Glycol | 0 | 0 |
| Acetol | 1.4 | 1.4 |

Use of Glycerol from Fatty Acid Glyceride Refinery

One preferred source of the polyhydric feedstock 104 is crude natural glycerol byproducts or intermediates, for example, as may be obtained from processes that make or refine fatty acid glycerides from bio-renewable resources. These are particularly preferred feedstocks for making an antifreeze mixture. When using these feedstocks, the antifreeze mixture is prepared as explained above by hydrogenation of glycerol over a catalyst, which is preferably a heterogeneous catalyst. The reactor-separator 102 may, for example, be a packed bed reactor, slurry, stirred or fluidized bed reactor. When the hydrogenation reaction is performed in a packed-bed reactor, the reactor effluent is largely free of catalyst. In the case of a slurry reactor, a heterogeneous catalyst may be filtered from the reactor effluent. The reactor-separator 102 may be used for slurry reactions by circulating hydrogen from the top vapor phase to the bottom of the reactor to create increased agitation and by preferably using a catalyst that has a density similar to the density of the liquid in the reactor. A fluidized bed may be used where the densities differ, where a catalyst bed is fluidized by the incoming hydrogen from line 108. Conventional agitation may also promote hydrogen contact in the liquid.

To make antifreeze, the process conditions need only provide moderate hydrogenation conversions of glycerol, e.g., those ranging from 60% to 90% conversion. This is because from 0% to 40% of the glycerol in the polyhydric feedstock 104 on a water-free basis may remain with propylene glycol products in the antifreeze product. For some product applications, the final antifreeze product may suitably contain up to 60% glycerol. Furthermore, when the product 118 contains a low glycerol concentration, e.g., less than 40% where there is an effective conversion of 60% to 90%, other known antifreezes may be mixed with the products 118. Alternatively, the purge materials 122 may be mixed with the contents of condensate tank 114, for example, after filtering, to form a salable product that may be directly discharged from the process equipment 100.

One particularly preferred source of polyhydric feedstock 104 for the reaction is the natural glycerol byproduct that is produced during the value-added processing of naturally occurring renewable fats and oils. For example, the glycerol byproduct may be a vegetable oil derivative, such as a soy oil derivative. This variety of polyhydric feedstock 104 may contain water, soluble catalysts, and other organic matter that are present in intermediate mixtures which are produced in the manufacture of glycerol for sale into the glycerol market. One advantage of the present instrumentalities is that little or no refining of these intermediates are necessary for their use as polyhydric feedstock 104 in making commercial antifreeze or deicing mixtures.

These intermediates and other polyhydric feedstocks 104 may contain high amounts of water. The ability to use polyhydric feedstocks 104 that contain high amounts of water advantageously reduces costs for this process over other uses for the glycerol. The water content both in the polyhydric feedstock 104 prior to the reaction and in the salable reaction product is generally between 0 and 50%.

The polyhydric feedstock 104 may contain residual catalyst that was added during alcoholysis of these intermediates. The fate of soluble residual catalysts, i.e., those that remain from alcoholysis in the polyhydric feedstock 104 and which are in the purge material 122 depends upon:

1. the specific type of soluble residual catalyst, and
2. any interaction between the residual catalyst and another catalyst that is added to the crude glycerol to promote hydrogenation within reactor-separator 102.

The residual catalyst content in the glycerol feedstock 104 from the processing of bio-renewable fats and oils is commonly between 0% and 4% or even up to 10% by weight on a water-free basis. One way to reduce the residual catalyst content is to minimize the amount that is initially used in alcoholysis of the fatty acid glyceride. The alcoholysis may, for example, be acid-catalyzed. Neutralizing the residual catalyst with an appropriate counter-ion to create a salt species that is compatible with the antifreeze specifications is preferred to removing the residual catalyst.

Alternatively, neutralization can be performed to precipitate the catalyst from the liquid glycerol. Calcium-containing base or salt may be used to neutralize the residual catalyst in the polyhydric feedstock 104, and the solid salts generated from this neutralization may be separated from the liquid, for example, by filtration or centrifugation of effluent from reactor-separator 102, such as by filtering purge material 122. Acid-base neutralization to form soluble or insoluble salts is also an acceptable method of facilitating separation. Specifically, neutralizing potassium hydroxide with sulfuric acid to form the dibasic salt is a acceptable procedure. As shown by way of example in FIG. 1, neutralization of sodium or potassium catalyst, which is sometimes introduced into the value-added processing method for fats and oils, can be achieved by adding stoichiometric equivalent amounts of a neutralizing agent 126, such as calcium oxide and/or sulfuric acid, to form the calcium salt of the catalyst. These salts are largely insoluble and may be filtered from the purge material 122. To improve separation of the substantially insoluble salt, the water content is preferably reduced to less than 20% by weight and the filtration is preferably performed at temperatures less than 40° C. and more preferably below 30° C. The optimal filtration temperature depends upon composition where the reduced solubility of salts at lower temperatures is weighed against lower viscosities at higher temperatures to identify the best filtration conditions.

One general embodiment for processing of crude glycerol to antifreeze in the fatty acid glyceride refinery embodiment follows a $C_1$ to $C_4$ alkyl alcohol alcoholysis process. The incoming crude glycerol feedstock 104 is neutralized by the addition of a neutralizing agent 126 to achieve a pH between 5 and 12, which is more preferably a pH between 5 and 9. The $C_1$ to $C_4$ alcohol and water are separated by distillation from the crude glycerol, such that the combined concentrations of water and $C_1$ to $C_4$ alcohols within reactor-separator 102 are less than 20 wt % by weight and, preferably, less than 5% by weight. In a stepwise process where the polyhydric feedstock 104 is added to the reactor-separator 104 at periodic intervals, selected components of these alcohols and/or their reaction products may be isolated by fractional distillation through overhead line 110 and discharged from condensate tank 114. This may be done by flash liberation of such alcohols at suitable times to avoid or limit their combining with propanediols, according to the principle of fractional distillation. Subsequent hydrogenation of the flashed glycerol within reactor-separator 102 suitably occurs by contacting the crude glycerol with a hydrogenation catalyst and hydrogen at a pressure ranging from 1 bar to 200 bar and at a temperature ranging from 100° to 290° C. until a conversion of the glycerol between 60% and 90% is achieved. More preferably, process conditions entail the contact pressure for hydrogenation ranging from 1 to 20 bar.

Separating the $C_1$ to $C_4$ alcohol and water is preferably achieved by selective flash separation at temperatures greater than 60° C. and less than 300° C. Alternatively, separating the $C_1$ to $C_4$ alcohol and water may be achieved in a process based on thermal diffusion, as is described in related application Ser. No. 10/420,047, where for example the reactor-separator 102 is a thermal diffusion reactor. Alternatively, water is added prior to hydrogenation as water promotes hydrogenation in the presence of certain catalysts.

The amount of organic matter in the polyhydric feedstock is substantially dependent upon the fat or oil from which the glycerol was obtained. The organic matter (other than glycerol) is typically fatty acid derivatives. One method for mitigating residual organic matter is by filtration. Alternatively, it is possible to decant insoluble organics from the glycerol in a gravity separator (not shown) at temperatures between 25 and 150° C. As necessary, the flash point of the mixture is preferably increased to greater than 100° C. by flash separation of volatiles from the glycerol-water mixture. Specifically, the residual $C_1$ to $C_4$ alkyl alcohol content in the feedstock is flash liberated to achieve feedstock concentrations that are preferably less than 1% alkyl alcohol. Depending upon the alkyl alcohol, vacuum may need to be applied to reach achieve the 1% alkyl alcohol concentration.

The following are preferred reaction conditions for conversion for use in processing these feedstocks. These are similar but not exactly the same as preferred+conditions that have been previously described for use in the reactor-separator 102. The reaction temperature is 150° C. to 250° C. The reaction time is from 4 to 28 hours. Heterogeneous catalysts are used which are known to be effective for hydrogenation, such as palladium, nickel, ruthenium, copper, copper zinc, copper chromium and others known in the art. Reaction pressure is from 1 to 20 bar, but lower and higher pressures also work. Water in the polyhydric feedstock is preferably from 0% to 50% by weight, and more preferably from 5 to 15% water by weight.

The preferred reaction conditions provide a number of performance advantages. Operating at temperatures less than 250° C. dramatically reduces the amount of unintended by-product formation, for example, where lower concentrations of water may be used without formation of polymers or oligomers. Furthermore, operation at temperatures near 200° C., as compared to near 300° C., provides an increased relative volatility of propylene glycol that facilitates an improved separation of propylene glycol from the glycerol reaction mixture. The use of lower pressures allows the use of less expensive reaction vessels, for example, as compared to high-pressure vessels that operate above about 28 bars, while also permitting the propylene glycol to distill from solution at these temperatures. Even so, some embodiments are not limited to use at pressures less than 20 bars, and may in fact be practiced at very high hydrogen pressures. The disclosed process conditions are viable at lower pressures (less than 20 bar) whereas most other processes to produce similar products require much higher pressures.

By these instrumentalities, glycerol may also be hydrogenolysed to 1, 2 and 1,3 propanediols. The 1,3 propanediol may be optionally separated from this mixture by methods known in the science and used as a monomer while the remaining glycerol and propanediols are preferably used as antifreeze.

EXAMPLE 3

Packed-Bed Reactor Embodiments

One method of preparing acetol and propylene glycol from glycerol includes a gas phase reaction at a temperature ranging from 150° to 280° C. in a packed-bed reactor. In some embodiments this temperature is more preferably from 180° C. to 240° C. or 250° C. to avoid thermal degradation of reaction products. The reactions described herein occurred in a packed-bed reactor. The pressures in the reaction vessel are preferably from 0.02 to 25 bars and in some embodiments this pressure is more-preferably between 0.02 and 10 bars. Most preferably, the reaction pressure exists within a range from 0.2 and 1.2 bars.

Figure 4:
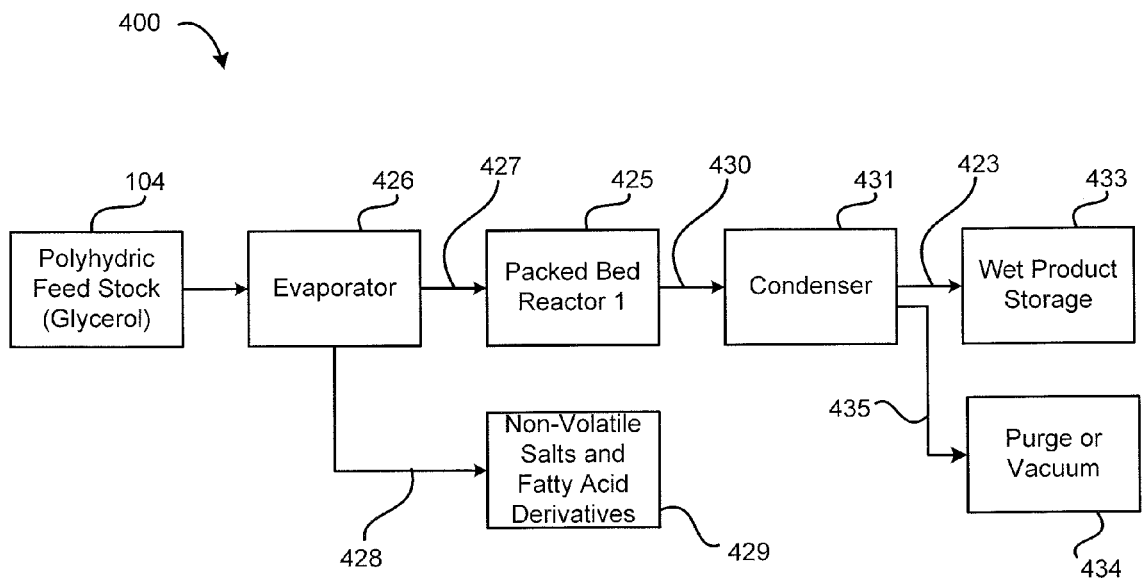
FIG. 4 is a schematic of the disclosed two-step alternative embodiment for converting glycerol to acetol and then converting acetol to propylene glycol, where the process equipment may also be used to make propylene glycol with no intermediate step.

FIG. 4 provides a block flow diagram of process equipment 400 including an evaporator 426 for creating a vapor reaction mixture 427. Non-volatile components 428 in the polyhydric feed 104 are removed from the evaporator 426 in a continuous or semi-batch mode. The evaporator 426 is particularly effective for processing crude glycerol that contains salts where, otherwise, the salts poison the catalyst. A polyhydric feed stock 104, for example, containing glycerol, is introduced stepwise or continuously into the evaporator 426. The vapor reaction mixture 427 proceeds to the packed-bed reactor 425 where the heterogeneous catalyst promotes conversion of glycerol 104 to acetol and propylene glycol in sequential reactions. The vapor product mixture 430 proceeds to the condenser 431 where a condensate product is formed 432 and proceeds to product storage 433. The gas effluent may disposed through purge or vacuum 434.

Water is produced as a reaction byproduct and may be kept with the propylene glycol product or removed. A major advantage of the current process over other processes in the literature is the very low concentration or absence of ethylene glycol resultant from either the use of copper chromite catalyst or formation and purification of acetol as an intermediate. The acetol can be readily purified from any ethylene glycol prior to hydrogenation by distillation.

The processes of this operation may be maintained at pressures below 1 bar through the use of a vacuum source preferably connected to the condensation process at the end of the process. In the most ideal of cases, the condenser 431 itself can maintain pressures less than 1 bar; however, from a practical perspective, a vacuum is needed to pull off any inert gases (nitrogen etc.) that may accumulate in the system.

Figure 5:
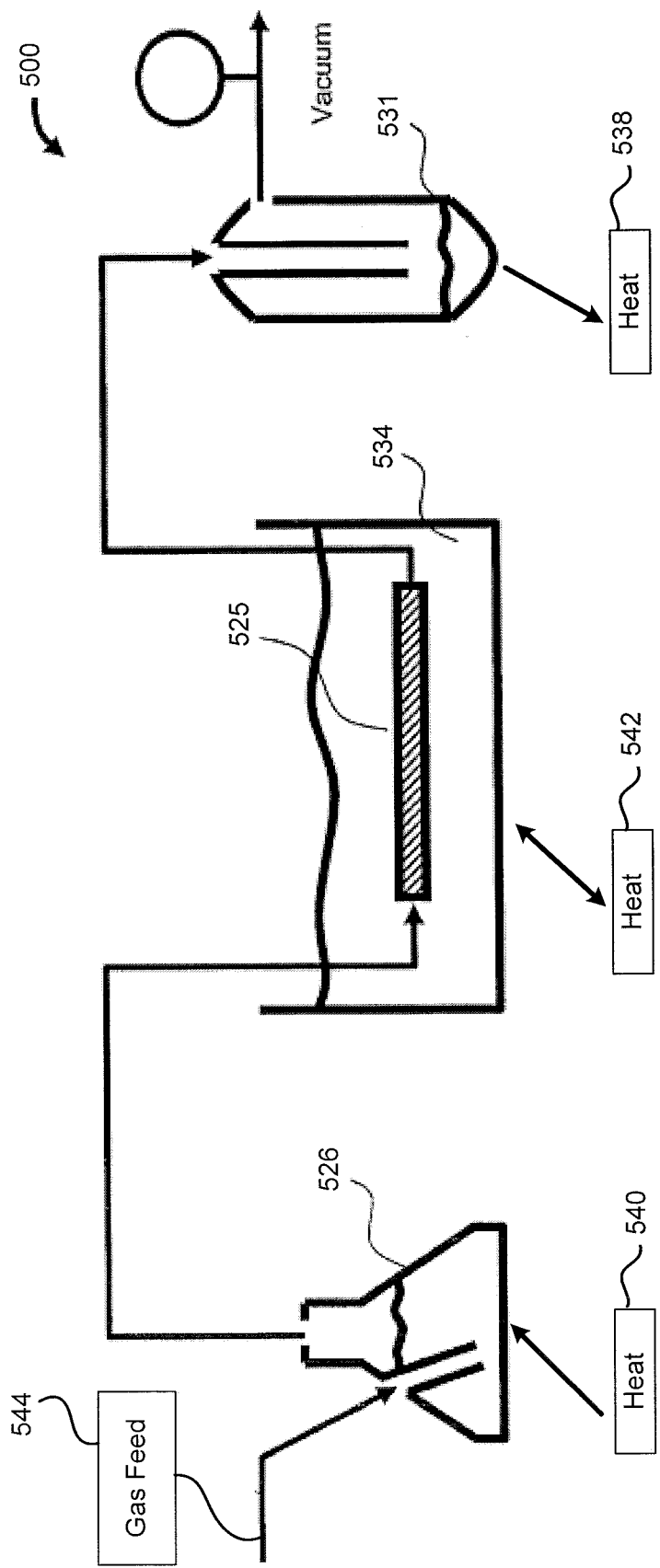
FIG. 5 is a schematic of laboratory process equipment that may be used to demonstrate the process equipment of FIG. 4 or 6.

The reaction system of FIG. 4 is effective for producing either acetol or propylene glycol. FIG. 5 provides a schematic diagram of the laboratory equipment 500 showing a variation of this equipment 500, which includes an evaporator 526 connected to the packed bed reactor 525. Vapor effluent from packed bed reactor 525 is condensed in the condenser 531 by action of a cold bath to draw heat 538. Heat 540 is applied to the evaporator 526 to create the vapor reagent. A vacuum 542 connected to the condenser 531 literally pulls the vapors through the system and allows the glycerol feed to evaporate at lower temperatures than would occur at atmospheric pressure. An oil bath 534 maintains the packed bed reactor 535 at a predetermined temperature or temperature range by flow of heat 542. The glycerol is loaded into the evaporator 526 at the start of the experiment and may be added through an auxiliary feed to the evaporator (not shown) during the experiment. An optional gas feed 544 that contains nitrogen and may also contain hydrogen is directed to the evaporator 526.

The process equipment shown in FIG. 5 was used to react glycerol under various conditions. Various runs were made using the equipment 500 according to the materials and conditions reported in Table 6. Reaction G1 of Table 6 provides example conversion data over 3.3 mm cylindrical pellets of copper chromite catalyst. The pressure of this reaction was less than 0.1 bar, and the temperature is about 230° C. Reaction G1 illustrates the effectiveness of the gas phase reaction over a packed-bed of catalyst for producing acetol in high selectivity.

TABLE 6

Summary of gas phase reactor performances in packed-bed reactor.

| RXN/Date | Conditions | Sample | Acetol (wt %) | PG (wt %) | Glycerin (wt %) | Acetol + PG (wt %) | Water (wt %) | Area of by-product 10.77/ Area of standard | Total Mass balance (wt %) |
|---|---|---|---|---|---|---|---|---|---|
| G1 Before 2005/9/29 | Catalyst packing (size: 3 * 3 mm) ~50-60 g Control (No gas Purge) Reactor temp: 230 C. Pressure: 29.9 in-Hg (vac) | 1 2 3 | 13.44 13.43 12.24 | 0.97 1.08 1.06 | 72.92 77.88 69.51 | 14.41 14.51 13.3 | 8.25 8.07 12 | 0.12 0.11 0.12 | 95.58 100.46 94.81 |
| | Proof of Concept - Low pressure dehydration reaction works. | | | | | | | | |
| G2 Before 2005/9/29 | Catalyst packing (size: 3 * 3 mm) ~50-60 g Hydrogen Purge Reactor temp: 230 C. Pressure: 26 in-Hg (vac) | 1 2 3 4 | 19.01 18.42 16.24 15.81 | 1.68 1.79 1.56 1.62 | 70.70 72.42 75.50 75.87 | 20.69 20.21 17.80 17.43 | 5.86 5.38 5.21 4.97 | 0.10 0.11 0.10 0.11 | 97.25 98.01 98.51 98.27 |
| | Experiment demonstrates that hydrogen partial pressure reduces water formation and leads to improved mass balance - better yields. Conversions appeared to be higher. | | | | | | | | |
| G3 Before 2005/9/29 | Catalyst packing (size: 3 * 3 mm) ~50-60 g Nitrogen Purge Reactor temp: 230 C. Pressure: 26 in-Hg (vac) | 1 | 9.75 | 0.53 | 87.27 | 10.28 | 3.87 | 0.16 | 101.42 |
| | Nitrogen was not as good as hydrogen based on higher water content of nitrogen reaction. Theoretical water is 1 part water for four parts acetol (acetol + propylene glycol). Actual water is greater than theoretical. The ratio of the by-product peak to desired product is higher for this nitrogen run. | | | | | | | | |
| G4 2005/9/29 | Catalyst packing (size: 3 * 3 mm) 50 g HOT PLATE (No gas Purge) Reactor temp: 230 C. Pressure: 27 in-Hg (vac) | 1 2 | 9.88 12.65 | 2.41 0 | 79.15 77.26 | 12.29 12.65 | 9.05 8.03 | 0.12 0.14 | 100.49 97.94 |
| | This run summarizes a different feed mechanism where feed is put on a hot plate to evaporate feed as it is introduced. Method provided improved experimental control but did not lead to new insight into the reaction. | | | | | | | | |
| G5 2005/10/4 | Catalyst packing (size: 3 * 3 mm) 50 g Hydrogen Purge Nitrogen Purge Reactor temp: 230 C. Pressure: 27 in-Hg (vac) | 1 1 | 12.52 7.79 | 2.86 0.81 | 78.4 87.94 | 15.38 8.60 | 4.18 3.56 | 0.11 0.14 | 97.96 100.1 |

TABLE 6-continued

Summary of gas phase reactor performances in packed-bed reactor.

| RXN/Date | Conditions | Sample | Acetol (wt %) | PG (wt %) | Glycerin (wt %) | Acetol + PG (wt %) | Water (wt %) | Area of by-product 10.77/ Area of standard | Total Mass balance (wt %) |
|---|---|---|---|---|---|---|---|---|---|
| | These runs are a repeat comparison of the use of hydrogen versus nitrogen. The hydrogen provided higher yields, more propylene glycol, less additional water, and fewer junk peaks. Motivation for increased use of hydrogen was the fat that production of PG must grab a hydrogen from somewhere, and that somewhere could only be other glycerin or acetol products - leading to the hypothesis that addition of hydrogen would increase the yield of desired products. | | | | | | | | |
| G6 2005/10/5 | Catalyst packing (size: 9-40 mesh) 50 g - fresh Hydrogen Purge Reactor temp: 230 C. Pressure: 27 in-Hg (vac) | 1 2 | 23.05 24.3 | 1.66 1.49 | 73.1 72.21 | 24.71 25.79 | 5.00 5.07 | 0.07 0.08 | 102.81 103.07 |
| | This run summarizes the impact of using smaller catalyst. The conversion increased by 50%. | | | | | | | | |
| G7 2005/10/10 | Catalyst packing (size: 9-40 mesh) 100 g - fresh Hydrogen Purge Reactor temp: 230 C. Pressure: 27 in-Hg (vac) | 1 2 | 44.74 42.56 | 2.4 2.3 | 37.49 38.01 | 47.14 44.86 | 12.00 9.93 | 0.06 0.07 | 96.63 92.8 |
| | This run summarizes the impact of using more smaller catalyst. Doubling the catalyst concentration doubled the conversion. To a first approximation, this reaction is zero-order. | | | | | | | | |
| G8 2005/10/11 | Catalyst packing (size: 9-40 mesh) 150 g - 100 g used 1, 50 g fresh Hydrogen Purge Reactor temp: 240 C. Oil batch temp: 232 C. Pressure: 27 in-Hg (vac) | 1 2 3 | 64.11 63.14 63.73 | 6.42 5.64 5.28 | 4.3 4.46 7.28 | 70.53 68.78 69.01 | 19.00 19.25 17.88 | 0.00 0.00 0.00 | 93.83 92.49 94.17 |
| | This run summarizes the impact of using even more smaller catalyst smaller catalyst. Tripling the catalyst concentration (50 to 150 grams) tripled the conversion. To a first approximation, this reaction is zero-order. | | | | | | | | |
| | Total glycerin reacted: 369.11 g Total products: 360.52 g Reaction time: 2.5 hr Mass balance of glycerin in versus product formed is pretty good for this system. | | | | | | | | |
| G9 2005/10/11 | Catalyst packing (size: 9-40 mesh) 150 g - 100 g used 2, 50 g used 1 Hydrogen Purge Reactor temp: 240 C. Oil batch temp: 232 C. Pressure: 27 in-Hg (vac) Total glycerin reacted: 754.79 g Total products: 750.40 g Reaction time: 5 hr | 1 2 3 | 62.35 64.28 60.39 | 7.51 5.03 4.39 | 6.25 7.24 14.11 | 69.86 69.31 64.78 | 18.57 18.89 19.01 | 0.00 0.00 0.06 | 94.68 95.44 97.9 |
| | This extended run shows good mass balance of glycerin in versus product out. Slight decrease in conversion with time deemed to be within experimental error. | | | | | | | | |
| G10 2005/10/14 | Acetol to PG with H2 Purge on a HOT PLATE Catalyst packing (size: 9-40 mesh) 150 g | | | | | | | | |
| | Pressure: 27 in-Hg (vac), closed valve | 1 | 53.4 | 22.53 | | | 5.42 | | 81.35 |
| | Pressure: 20 in-Hg (vac), open valve to maintain pressure | 2 | 42.16 | 11.09 | | | 37.38 | | 90.63 |
| | Pressure: 20 in-Hg (vac), more H2 flow to maintain pressure | 3 | 33.57 | 14.29 | | | 43.94 | | 91.8 |

Improved Packed-Bed Embodiments

It was observed that propylene glycol was produced in illustrative example G1 of Table 6. Since the only source of hydrogen for reacting with acetol (or glycerol) to form propylene glycol was from another acetol or glycerol molecule it was hypothesized that the absence of free hydrogen in the system led to scavenging of hydrogen from the glycerol and that this scavenging led to undesired byproducts and loss in yield.

Figure 6:
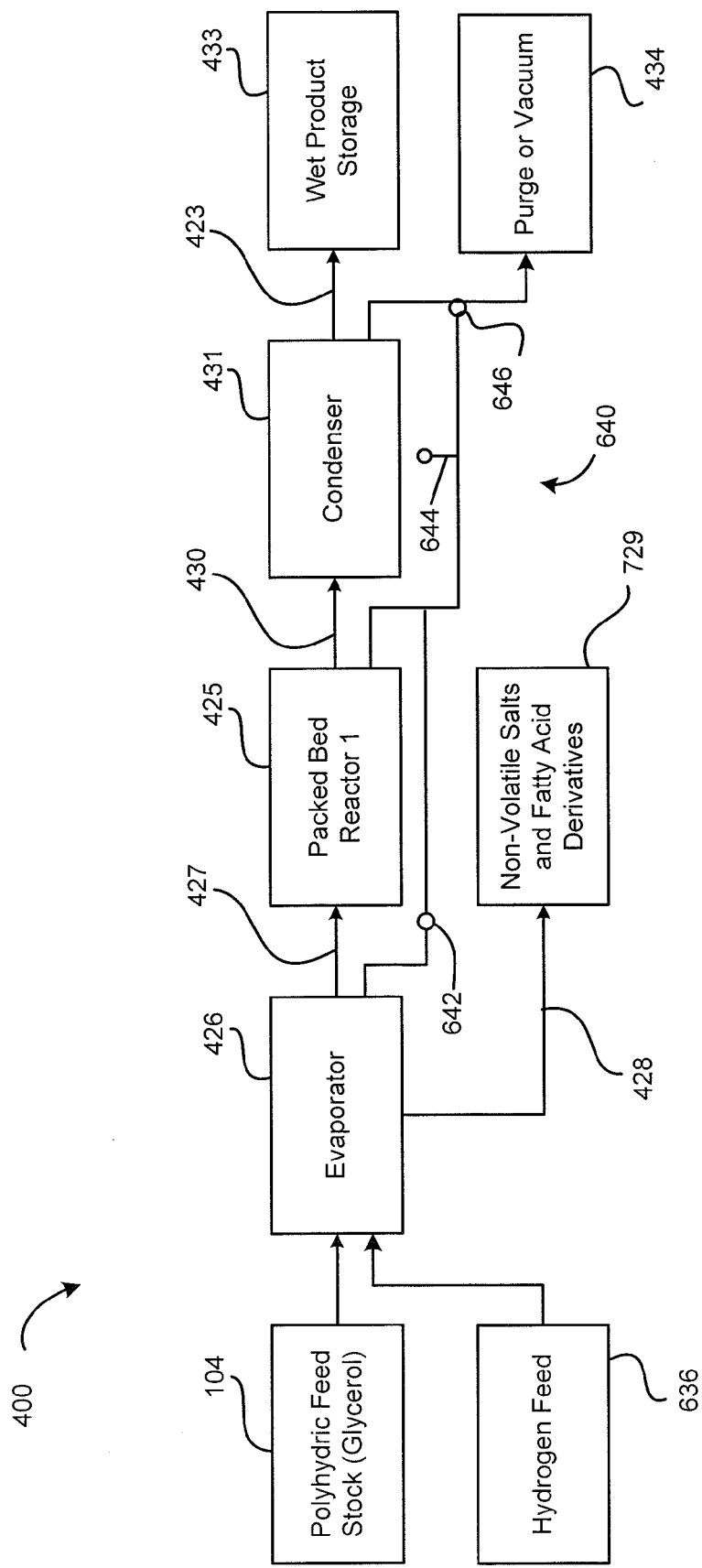
FIG. 6 is a schematic of the disclosed two-step alternative embodiment for converting glycerol to acetol and then converting acetol to propylene glycol where hydrogen is used for the first reactor at a lower pressure and water is removed from the vapor effluents from the first reactor to allow purging of the water from the system.

To overcome the problem with scavenging of hydrogen from glycerol, a small amount of hydrogen was introduced to the system. FIG. 6 illustrates the preferred packed-bed reaction process equipment 600 with hydrogen feed 636 as a modification to the process equipment of FIG. 4 The hydrogen feed 636 was introduced to the evaporator 426 since this gas diluents, in addition to being useful in hydrogenating acetol, also promotes evaporation of glycerol. Since glycerol has a vapor pressure of a mere 0.15 bar at 230° C., the hydrogen overpressure can add to this pressure to increase overall pressure—but this is primarily possible if glycerol is evaporated in the presence of a gas like hydrogen. The condenser 431 condenses the acetol and propylene glycol from unreacted gas. although the unreacted gas may be purged 434, a recycle loop 640 may be used to resupply the evaporator 426, packed bed reactor 425, or condenser 431 by selective arrangement of valves 642, 644, 646.

Reaction G2 of Table 6 provides example conversion data illustrating the beneficial impact of a hydrogen feed (purge) 544 (see FIG. 5) as the hydrogen feed 636 of FIG. 6 combined with the glycerol feed in the packed-bed reactor 425. The pressure of was 0.13 bars, and the temperature was 230° C. A higher yield to acetol and propylene glycol was observed.

The desired dehydration reactions produce one water molecule for every acetol (or propylene glycol) molecule that is formed. Water present in excess of this indicates excess dehydration and lower selectivities. The ratio of actual to theoretical water content decreased from 2.3-3.6 to 1.07-1.17 as a result of hydrogen being present during the dehydration reaction. In addition, a GC peak at 10.77 minutes is a by-product. The ratio of this peak area to the mass fractions of desired acetol and propylene glycol decreased from 0.76-0.9 to 0.47-0.63 as a result of hydrogen being present during the dehydration reaction.

To confirm that the desired results were a result of hydrogen rather than any diluent in the system, experiment G3 was performed using nitrogen instead of hydrogen. The ratio of actual to theoretic water increased to 1.51 with nitrogen. In addition the ratio of the 10.77 minute peak increased to 1.56.

Both the hydrogen and nitrogen diluent/purge experiments were repeated in experiment G5 with generally repeatable results and validation of the benefit of using hydrogen as a diluent/purge during the dehydration reaction that forms primarily acetol as a product.

The preferred process uses a hydrogen diluent and reagent 636 introduced to the evaporator 426.

The following are a summary of the experiments summarized in Table 6 and what the results indicate:

Experiment G1 provides proof of concept of low-pressure dehydration over a packed-bed catalyst.

Experiment G2 demonstrates that hydrogen partial pressure reduces water formation and leads to improved mass balance—better yields. Conversions appeared to be higher.

Experiment G3 demonstrates that nitrogen was not as good as hydrogen based on higher water content of nitrogen reaction. Theoretical water is 1 part water for four parts acetol (acetol+propylene glycol). Actual water for this experiment is considerably greater than theoretical. The ratio of the by-product peak (10.77 minutes) to desired product is higher for this nitrogen run.

Experiment G4 demonstrates a continuous feed mechanism approach where feed is put on a hot plate to evaporate feed as it is introduced. Method provided improved experimental control but did not lead to new insight into the reaction.

Experiment G5 provides a repeat comparison of the use of hydrogen versus nitrogen. The hydrogen provided higher yields, more propylene glycol, less additional water, and fewer junk peaks. Motivation for increased use of hydrogen was the fat that production of PG must grab a hydrogen from somewhere, and that somewhere could only be other glycerol or acetol products—leading to the hypothesis that addition of hydrogen would increase the yield of desired products.

Experiment G6 summarizes the impact of using smaller catalyst. The conversion increased by 50%.

Experiment G7 summarizes the impact of using more smaller catalyst. Doubling the catalyst mass doubled the conversion. To a first approximation, this reaction is zero-order.

Experiment G8 summarizes the impact of using even more smaller catalyst smaller catalyst. Tripling the catalyst mass (50 to 150 grams) tripled the conversion. To a first approximation, this reaction is zero-order.

Experiment G9 summarizes a good mass balance of glycerol relative to the reaction products.

Experiment G10 repeats the mass balance run of G9 illustrating a good mass balance of glycerol in versus product out. A slight decrease in conversion with time was deemed to be within experimental error.

Experiments validated conversions of greater than 95% for the conversion of glycerin to acetol. At conversions of about 98%, approximately 70% acetol and 9% propylene glycol were present in the product. Continued contact of both hydrogen and acetol over the copper chromite catalyst continued to increase yields to propylene glycol.

Other Packed-Bed Embodiments

Figure 7:
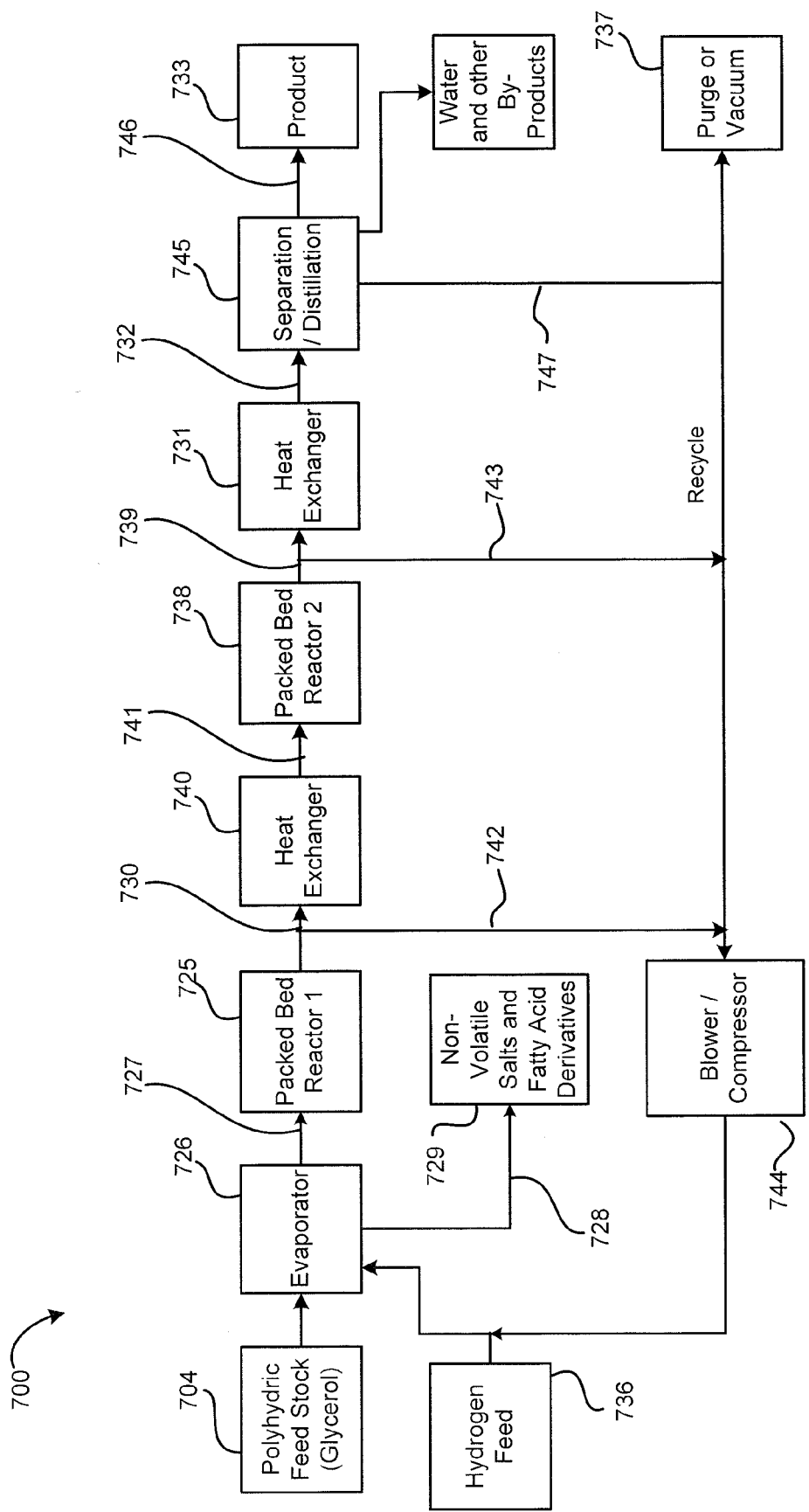
FIG. 7 is a schematic block flow diagram illustrating a packed-bed reactor with an evaporator, reactor, and condenser.

FIG. 7 shows a more preferred process of preparing propylene glycol from glycerol.

FIG. 7 provides a block flow diagram of process equipment 700 including glycerol (or polyhydric) 704 and hydrogen feeds 736. The hydrogen is contacted with the glycerol in an evaporator 726 operated between about 200 and 250° C., which promotes evaporation of glycerol to form a vapor reactor enfluent 727. A first packed-bed reactor 725 converts glycerol to acetol with some formation of propylene glycol.

If hydrogen is present, the acetol will react with hydrogen to form propylene glycol in the first packed-bed reactor 725. At low hydrogen partial pressures, about 0.1 bar, acetol is predominantly formed. At higher hydrogen pressures, more propylene glycol is formed. The formation of acetol is predominantly rate limited. The reaction of acetol to propylene glycol is fast relative to the reaction of glycerol to acetol; however, the acetol to propylene glycol reaction is equilibrium limited. Since reaction of acetol to propylene glycol is equilibrium limited, recycle of acetol is useful to maximize production of propylene glycol. Distillation can be used to concentrate acetol from the product stream for recycle to the evaporator or other locations prior to the reactor.

One method of operating the process of FIG. 7 is to add additional hydrogen to stream 741 whereby acetol is primarily formed in the first packed-bed reactor 725 and propylene glycol is primarily formed in the second packed-bed reactor 738.

The dehydration reaction in the first packed-bed reactor 725 is highly exothermic. For example, the heat of reaction will increase glycerol initially at 200° C. to acetol at 414° C. at 100% conversion and without any solvent/diluent. The higher temperatures lead to a loss of production and generation of undesired by-products. Heat must be continuously or stepwise removed from the reaction mixture to maintain temperatures below 250° C., preferably below 230° C., and most preferably below 220° C.

The mixture is preferably cooled to about 220° C. in a heat exchanger 740 prior to hydrogenolysis 741 in packed-bed reactor two 738. Reactor two 738 is preferably a packed-bed reactor. Copper chromite catalyst is effective in reactor two; however, other hydrogenation catalysts may also be used such as Raney-nickel catalyst. The hydrogenolysis reaction is also highly exothermic.

Although high conversions are possible for both the dehydration and hydrogenolysis reaction, a separator 745 is used to further purify the product 733.

Preferably, the reactor 1 effluent 730 and reactor 2 effluent 739 are recycled 742/743 along with the overheads 747 of the separator 745. A blower 744 is used to overcome pressure drops for the recycle. If the separator overhead 747 is a liquid, it is pumped rather than compressed. The hot recycle streams 742/743 may have temperatures up to 300° C. and reduce or eliminate the need for auxiliary heat addition to the evaporator 726. This direct contact heat exchange and evaporation is very efficient. These recycle streams serve the addition purpose of providing additional heat capacity to the reactor effluents 727/741, and this additional heat capacity minimizes temperature increases in the reactors. Minimizing temperature increases maximizes yields of acetol and propylene glycol.

Recycled vapors 742/743/747 add additional partial pressures from acetol, water, and propylene glycol; combined, these may add from 0.2 to 1.2 bars of partial pressure. Recycle stream 1042 has the advantage of providing heat to the evaporator 1026, but has the disadvantage of increasing the residence time of acetol that can degrade acetol. Recycle stream has advantages associated with providing heat to the evaporator. Recycle stream 1047 can be enriched in hydrogen as a recycle, which is advantageous for the reaction, but is not advantageous for providing heat to the evaporator. The corresponding total pressure in the evaporator and downstream unit operations is about 0.3 to 1.5 bars. The preferred pressure is about 1.1 bars such that about 0.3 bars is fresh feed glycerol and hydrogen, about 0.4 bars is recycled hydrogen, and about 0.4 bars is recycled water vapor—heat exchangers are preferred to recover heat from the hot reaction products into the evaporator and vapors recycled to the evaporator.

Due to the exothermic nature of the both the dehydration and hydrogenolysis reactions, temperature control is most important. The preferred means to control temperature is to use recycled water and hydrogen as a diluent in combination with heat exchangers between a first and second reactor. More than two reactors is optional. In addition, use of cold shots of propylene glycol or water in either reactor 1025/1038 or the heat exchanger between the reactors 1040. For example, cold shots of propylene glycol from the product stream 1046 can be used to maintain temperatures less than 250° C. throughout the system.

Figure 8:
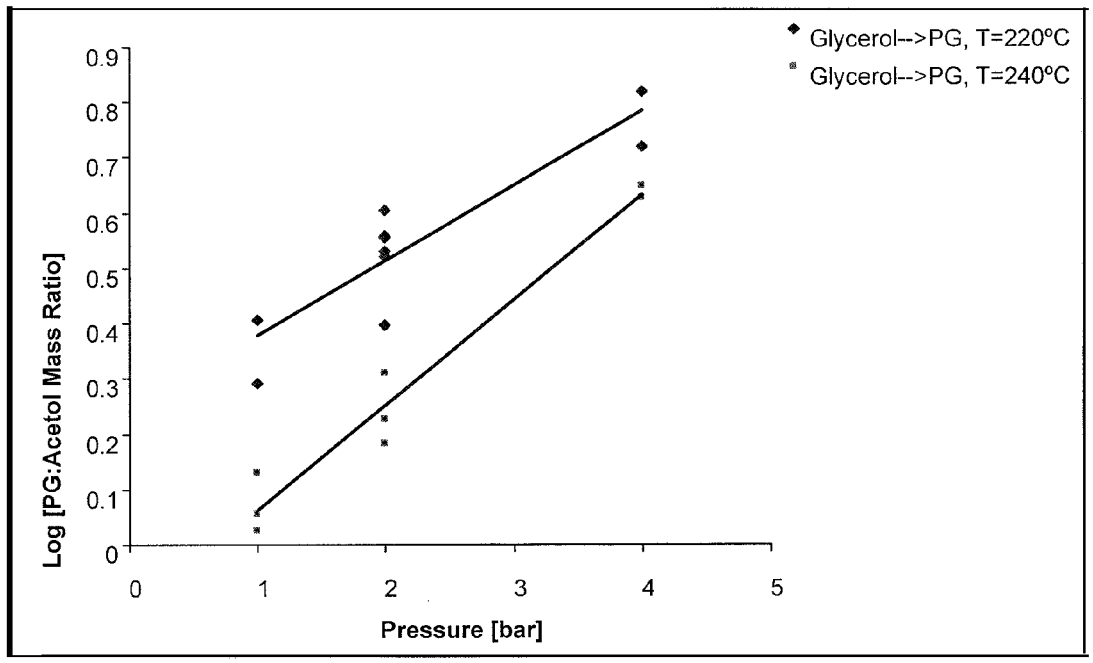
FIG. 8 shows pressure dependence of the glycerol to propylene glycol reaction at temperatures of 220° C., and 240° C.

Table 7 and FIG. 8 show the impact of temperature and pressure on the ratio of propylene glycol to acetol in the product for a reaction at a residence time slightly longer than is necessary to fully react all the glycerol. Table 7 summarizes the ratio of propylene glycol to acetol where propylene glycol was used as the feed (not glycerol in the system). The fact that propylene glycol reacts to form acetol fully validates that this reaction is equilibrium limited. The fact that the forward (glycerol as reactant) and backward (propylene glycol is reactant) produce essentially the same ratios of propylene glycol at similar temperatures and pressures indicates that the acetol to propylene glycol reaction is predominantly equilibrium limited rather than rate limited.

TABLE 7

Effect of Temperature and Pressure on the Formation of Propylene Glycol from Glycerol.*

| Reactor Temperature [° C.] | Pressure of Discharge [bar] | Acetol [wt %] | PG [wt %] | [PG:Acetol Mass Ratio] | Reactor Temperature [K] | 1000/ Temperature [K] | Log [PG:Acetol Mass Ratio] |
|---|---|---|---|---|---|---|---|
| 220 | 1 | 26.00 | 50.84 | 1.96 | 493 | 2.03 | 0.29 |
| 220 | 1 | 18.58 | 47.29 | 2.55 | 493 | 2.03 | 0.41 |
| 238 | 1 | 20.29 | 27.31 | 1.35 | 511 | 1.96 | 0.13 |
| 241 | 1 | 24.45 | 27.73 | 1.13 | 514 | 1.94 | 0.05 |
| 240 | 1 | 29.70 | 31.35 | 1.06 | 513 | 1.95 | 0.02 |
| 220 | 2 | 22.64 | 56.31 | 2.49 | 493 | 2.03 | 0.40 |
| 220 | 2 | 17.56 | 63.71 | 3.63 | 493 | 2.03 | 0.56 |
| 220 | 2 | 18.34 | 65.75 | 3.59 | 493 | 2.03 | 0.55 |
| 221 | 2 | 16.60 | 56.51 | 3.40 | 494 | 2.02 | 0.53 |
| 220 | 2 | 12.74 | 51.20 | 4.02 | 493 | 2.03 | 0.60 |
| 221 | 2 | 14.88 | 49.38 | 3.32 | 494 | 2.02 | 0.52 |
| 237 | 2 | 23.35 | 35.53 | 1.52 | 510 | 1.96 | 0.18 |
| 236 | 2 | 19.91 | 40.56 | 2.04 | 509 | 1.96 | 0.31 |
| 240 | 2 | 18.85 | 31.80 | 1.69 | 513 | 1.95 | 0.23 |
| 220 | 4 | 10.50 | 69.47 | 6.62 | 493 | 2.03 | 0.82 |
| 220 | 4 | 12.55 | 65.83 | 5.25 | 493 | 2.03 | 0.72 |
| 240 | 4 | 6.95 | 30.91 | 4.45 | 513 | 1.95 | 0.65 |
| 240 | 4 | 12.12 | 51.36 | 4.24 | 513 | 1.95 | 0.63 |

*For these reactions, the total pressure is predominantly comprised of hydrogen where the molar ratio of hydrogen to alcohols is about 13:1.

FIG. 8 illustrates the data of Table 7 as pressure dependence of the glycerol to propylene glycol reaction, at temperatures of 220° C., and 240° C.

TABLE 8

Effect of Temperature and Pressure on the Formation of Acetol from Propylene Glycol.*

| Reactor Temperature [° C.] | Pressure of Discharge [bar] | Acetol [wt %] | PG [wt %] | [PG:Acetol Mass Ratio] | Reactor Temperature [K] | 1000/ Temperature [K] | Log [PG:Acetol Mass Ratio] |
|---|---|---|---|---|---|---|---|
| 203 | 1 | 17.36 | 64.31 | 3.70 | 476.15 | 2.10 | 0.57 |
| 239 | 1 | 34.27 | 39.16 | 1.14 | 512.15 | 1.95 | 0.06 |

TABLE 8-continued

Effect of Temperature and Pressure on the Formation of Acetol from Propylene Glycol.*

| Reactor Temperature [° C.] | Pressure of Discharge [bar] | Acetol [wt %] | PG [wt %] | [PG:Acetol Mass Ratio] | Reactor Temperature [K] | 1000/ Temperature [K] | Log [PG:Acetol Mass Ratio] |
|---|---|---|---|---|---|---|---|
| 202 | 1 | 21.33 | 72.40 | 3.39 | 475.15 | 2.10 | 0.53 |
| 237 | 1 | 34.56 | 34.67 | 1.00 | 510.15 | 1.96 | 0.00 |
| 177 | 2 | 6.39 | 88.90 | 13.91 | 450.15 | 2.22 | 1.14 |
| 181 | 2 | 11.07 | 85.55 | 7.73 | 454.15 | 2.20 | 0.89 |
| 184 | 2 | 11.06 | 87.84 | 7.94 | 457.15 | 2.19 | 0.90 |
| 181 | 2 | 11.6 | 87.06 | 7.51 | 454.15 | 2.20 | 0.88 |
| 182 | 2 | 11.03 | 89.24 | 8.09 | 455.15 | 2.20 | 0.91 |
| 183 | 2 | 10.15 | 92.22 | 9.09 | 456.15 | 2.19 | 0.96 |
| 207 | 2 | 15.58 | 75.00 | 4.81 | 480.15 | 2.08 | 0.68 |
| 220 | 2 | 18.19 | 63.25 | 3.48 | 493.15 | 2.03 | 0.54 |
| 216 | 2 | 17.25 | 61.20 | 3.55 | 489.15 | 2.04 | 0.55 |
| 237 | 2 | 35.1 | 36.08 | 1.03 | 510.15 | 1.96 | 0.01 |
| 240 | 2 | 23.61 | 43.64 | 1.85 | 513.15 | 1.95 | 0.27 |
| 242 | 2 | 21.77 | 36.54 | 1.68 | 515.15 | 1.94 | 0.22 |
| 204 | 4 | 10.35 | 80.10 | 7.74 | 477.15 | 2.10 | 0.89 |
| 239 | 4 | 21.91 | 58.34 | 2.66 | 512.15 | 1.95 | 0.43 |
| 197 | 4 | 5.8 | 94.01 | 16.21 | 470.15 | 2.13 | 1.21 |
| 242 | 4 | 11.29 | 34.45 | 3.05 | 515.15 | 1.94 | 0.48 |
| 242 | 4 | 20.96 | 52.45 | 2.50 | 515.15 | 1.94 | 0.40 |
| 241 | 4 | 9.15 | 41.65 | 4.55 | 514.15 | 1.94 | 0.66 |
| 240 | 4 | 13.02 | 59.51 | 4.57 | 513.15 | 1.95 | 0.66 |
| 240 | 4 | 13.63 | 55.59 | 4.08 | 513.15 | 1.95 | 0.61 |

*For these reactions, the total pressure is predominantly comprised of hydrogen where the molar ratio of hydrogen to alcohols is about 13:1.

Since the conversion of acetol to propylene glycol is equilibrium limited, reaction residence times that are longer than it takes to react the glycerol are not advantageous in forming more propylene glycol. In fact, at longer residence times, the product concentrations will decrease as the acetol and/or propylene glycol continue to react to form undesired by-products. As the data in Tables 7 and 8 indicate, higher pressures (4 bar rather than 1 bar) and lower temperatures (220° C. rather than 240° C.) tend to favor formation of propylene glycol. These trends are fully consistent with the exothermic nature of the hydrogenation of acetol to form propylene glycol and the fact that this reaction results in a reduction in the total moles in the system (two moles, one each of hydrogen and acetol, react to form one mole of propylene glycol).

Table 9 summarizes conversion data on a 15 foot reactor loaded with 760 and 1160 grams of 3×3 mm pellet copper chromium catalyst. The reactions were evaluated with glycerol evaporated at 230° C. The by controlling the vacuum at the exit from the cold trap (condenser), the pressure of the system was able to be operated at 27, 19, and 8 inches of mercury in vacuum (0.074, 0.34, and 0.71 bars absolute pressure). This increase in pressure causes the partial pressure and the stoichiometric excess of hydrogen to increase.

TABLE 9

Summary of gas phase reactor performances in "cobra' (15 flexible steel tube, 0.5 inch ID) packed-bed reactor.

| Date | Conditions | Sample | Acetol (wt %) | PG (wt %) | Glycerin (wt %) | Acetol + PG (wt %) | Water (wt %) | Unknown (wt %) | Total Mass balance (wt %) |
|---|---|---|---|---|---|---|---|---|---|
| G11 Oct. 22, 2005 Cobra | Direct Glycerin to PG with H2 Purge Catalyst packing (size: 3 * 3 mm) 760 g Hydrogen Purge Reactor temp: 240 C. | | | | | | | | |
| Increase H2 flow | Pressure: 27 in-Hg (vac) Pressure: 19 in-Hg (vac) | 1 2 | 55.13 42.41 | 13.91 23.88 | 10.88 18.23 | 69.04 66.29 | 16.4 16.06 | | 96.32 100.58 |
| G12 Oct. 24, 2005 Cobra | Direct Glycerin to PG with H2 Purge Catalyst packing (size: 3 * 3 mm) 1160 g Hydrogen Purge Reactor temp: 240 C. | | | | | | | | |
| Increase H2 flow | Pressure: 27 in-Hg (vac) Pressure: 19 in-Hg (vac) | 1 2 | 46.88 40.44 | 6.44 17.19 | 0 0 | 53.32 57.63 | 23.91 22.3 | 24.7 16.6 | 77.23 79.93 |
| Increase H2 flow | Pressure: 8 in-Hg (vac) | 3 | 36.63 | 37.1 | 0 | 73.73 | 18.18 | 9.3 | 91.91 |
| G13 Oct. 26, 2005 Cobra | Direct Glycerin to PG with H2 Purge Catalyst packing (size: 3 * 3 mm) 1160 g Hydrogen Purge Reactor temp: 230 C. | | | | | | | | |

TABLE 9-continued

Summary of gas phase reactor performances in "cobra' (15 flexible steel tube, 0.5 inch ID) packed-bed reactor.

| Date | Conditions | Sample | Acetol (wt %) | PG (wt %) | Glycerin (wt %) | Acetol + PG (wt %) | Water (wt %) | Unknown (wt %) | Total Mass balance (wt %) | |
|---|---|---|---|---|---|---|---|---|---|---|
| Increase H2 flow | Pressure: 27 in-Hg (vac) | 1 | 58.56 | 5.58 | 0 | 64.14 | | | 64.14 | excluding water |
| Increase H2 flow | Pressure: 19 in-Hg (vac) | 2 | 44.94 | 25.07 | 0 | 70.01 | | | 70.01 | excluding water |
| | Pressure: 8 in-Hg (vac) | 3 | 32.33 | 38.71 | 0 | 71.04 | | | 71.04 | excluding water |
| G14 Oct. 25, 2005 Cobra | Direct Glycerin to PG with H2 Purge Catalyst packing (size: 3 * 3 mm) 1160 g Hydrogen Purge Reactor temp: 220 C. | | | | | | | | | |
| Increase H2 flow | Pressure: 27 in-Hg (vac) | n | n | n | n | n | n | n | n | |
| Increase H2 flow | Pressure: 19 in-Hg (vac) | 1 | 44.58 | 29.9 | 0 | 74.48 | 19.71 | | 94.19 | |
| | Pressure: 8 in-Hg (vac) | 2 | 32.14 | 53.37 | 0 | 85.51 | 15.92 | | 101.43 | |
| G15 Oct. 26, 2005 Cobra | Direct Glycerin to PG with H2 Purge Catalyst packing (size: 3 * 3 mm) 1160 g Hydrogen Purge Reactor temp: 210 C. | | | | | | | | | |
| | Pressure: 27 in-Hg (vac) | 1 | 58.91 | 10.18 | 3.26 | 69.09 | | | 72.35 | excluding water |
| Increase H2 flow | Pressure: 19 in-Hg (vac) | 2 | 44.2 | 28.92 | 4.3 | 73.12 | | | 77.42 | excluding water |
| Increase H2 flow | Pressure: 8 in-Hg (vac) | 3 | 32.56 | 41.33 | 8.39 | 73.89 | | | 82.28 | excluding water |
| G16 Oct. 26, 2005 Cobra | Direct Glycerin to PG with H2 Purge Catalyst packing (size: 3 * 3 mm) 1160 g Hydrogen Purge Reactor temp: 200 C. | | | | | | | | | |
| | Pressure: 27 in-Hg (vac) | 1 | 56.13 | 3.53 | 2.11 | 59.66 | | | 61.77 | excluding water |
| Increase H2 flow | Pressure: 19 in-Hg (vac) | 2 | 38.42 | 31.13 | 3.78 | 69.55 | | | 73.33 | excluding water |
| Increase H2 flow | Pressure: 8 in-Hg (vac) | 3 | 28.54 | 41.8 | 9.93 | 70.34 | | | 80.27 | excluding water |

As seen by the data G11 through G16, in every instance the increase in hydrogen pressure resulted in better closure of the mass balance (higher selectivity) and higher conversions from acetol to propylene glycol. At 240° C., the selectivity to acetol/propylene glycol was lower than at 220° C.—at this higher temperature more "junk" peaks were on the GC indicating that product was lost to undesirable side-products. Selectivity increased as the progressively as the temperature was lowered from 240° C. (G12) to 230° C. (G13) to 220° C. (G14). At 210° C. (G15) and 200° C. (G16), the conversion of glycerin was less than 100%. The optimal temperature is near 220° C.

The preferred operation of the evaporator is at a temperature near 230° C., and contact of glycerin with gases is such that glycerin attains a partial pressure of about 0.15 bars. A preferred stoichiometric addition of hydrogen feed 1036 will add an additional partial pressure of about 0.15 bars or more of hydrogen.

It is possible to operate a two-reactor system such that acetol is predominantly formed in the first reactor and acetol is predominantly converted to propylene glycol in the second reactor. The first reactor could be a reactive distillation reactor operated at lower pressures or it could be a packed-bed reactor operated at lower pressures. There is little advantage to using higher pressures in the first reactor if the goal is to form acetol; the acetol is preferably produced from a process operated at a pressure less than 5 bars. Higher pressures are preferred for the hydrogenation of acetol to propylene glycol; for this reaction the preferred pressure is greater than 25 bar and acetol may be present as a liquid phase at these high pressures. When liquids are present, higher pressures are preferred, from at least 1 bar up to 500 bar or higher. If liquid acetol is present in the reactor, the reactor is preferably a slurry batch reactor, trickle bed reactor, and teabag reactor. The temperature for the hydrogenation is preferably less than 220° C. A gas phase packed bed reactor may also be used for the conversion of acetol to propylene glycol.

The advantage of using a reactor where acetol is a liquid for converting acetol to propylene glycol is that the liquid product can be selectively removed (rather than hydrogen) from the reaction environment. This can reduce separation costs and the costs of recycling hydrogen. An additional advantage is that the high pressures and lower temperatures (less than 220° C.) can substantially overcome the equilibrium limitations of the acetol-to-propylene glycol hydrogenation. The advantage of using a gas-phase packed-bed reactor is that lower pressures are required. An additional advantage of using a gas-phase packed-bed reactor is that by-product formation tends to be promoted in liquid phases—especially the formation of tar.

As an alternative to the two-reactor system, it is possible to form propylene glycol in a single reactor by operating this reactor with sufficient hydrogen present. Tables 7 and 8 illustrate how 1 to 4 bars of hydrogen pressure are sufficient for high selectivity. The data clearly extrapolates to favorable formation of acetol at lower hydrogen pressures (corresponding to lower partial pressures of hydrogen) and favorable formation of propylene glycol at higher pressures (corresponding to high partial pressures of hydrogen).

Alternatively, it is possible to use a two-reactor system where the first reactor is operated to promote conversion of glycerol predominantly to propylene glycol and the second reactor is operated at lower temperatures that create equilibrium favorable for further conversion of acetol to propylene glycol. Here, the first reactor preferably has reaction temperatures greater than 200° C. and the second reactor preferably has temperatures less than 220° C. Preferably the glycerol concentration entering the second reactor is less than half the glycerol concentration entering the first reaction step. More preferably, the first reaction step has reaction temperatures greater than 210° C. and the second reaction step has temperatures less than 210° C.

For gas phase reactions operated at moderate pressures (less than 25 bar), it is important to avoid formation of liquids. Liquids exhibit increased rates of by-product formation. At a given pressure, there is a minimum temperature below which liquids form. This temperature is a function of composition. The least volatile component is glycerol, and so, higher glycerol concentrations necessitate operating at higher temperatures, hence, in a two-reactor system the first reactor is operated at a higher temperature because the first reactor has the higher glycerol concentration.

The partial pressure of glycerol is the key parameter to be followed and controlled to avoid formation of liquids in the gas-phase packed-bed reactor. The partial pressure of glycerol must be kept below glycerol's dew point partial pressure. Glycerol's dew point partial pressure is defined as the partial pressure of glycerol below which glycerol does not form dew and at which a dew is formed that contains glycerol—this definition implies that the glycerol-free ratios of all other components in the system remain constant and the temperature is constant as the partial pressure of glycerol is increased until the a dew is formed. Being defined in this manner, glycerol's dew point partial pressure is a state property that is a function of temperature and the glycerol-free concentration of other components in the gas.

The preferred processes of this embodiment have a partial pressure of glycerol less than glycerol's dew point partial pressure in the reaction mixture and greater than one fourth the dew point partial pressure in the reaction mixture. More preferably, the partial pressure of glycerol is greater than half the dew point partial pressure in the reaction mixture. The reaction temperature is preferably below 230° C. because at higher temperatures, byproduct formation is favored. When the temperature gets too low (such as 180° C.), glycerol's dew point pressure becomes so low that reactor throughput can become too low to be economically viable. Also, at lower temperatures the dehydration of glycerol becomes slower, further leading to increased reactor sizes.

The partial pressure of glycerol is approximately the mole fraction of glycerol in the gas phase times the total pressure. Furthermore, for relatively pure glycerol in a gas entering the reactor, the dew formed at glycerol's dew point partial pressure is relatively pure glycerol. Hence at the dew point, to a good approximation, $y^{Dew}_{Glyc} P = P^{Sat}_{Glyc}$. where $y^{Dew}_{Glyc}$ is the dew point mole fraction of glycerol in the gas phase, P is total pressure, and $P^{Sat}_{Glyc}$ is the saturation pressure of pure glycerol at the temperature of the system. The dew point mole fraction of glycerol is the maximum that can be held in the gas phase. Table 10 summarizes dew point mole fractions at 1, 10, and 100 bar total pressure.

TABLE 10

Maximum mole fractions of glycerol in system at indicated temperature above which liquids will form in system.

| T (° C.) | Vapor Pressure Glycerol (bar) | Maximum $y_{Glyc}$ (Dew Point) @ 1 bar | Maximum $y_{Glyc}$ (Dew Point) @ 10 bar | Maximum $y_{Glyc}$ (Dew Point) @ 100 bar |
|---|---|---|---|---|
| 150 | 0.007 | 0.007 | 0.0007 | 0.00007 |
| 180 | 0.025 | 0.025 | 0.0025 | 0.00025 |
| 200 | 0.058 | 0.058 | 0.0058 | 0.00058 |
| 220 | 0.126 | 0.126 | 0.0126 | 0.00126 |
| 250 | 0.345 | 0.345 | 0.0345 | 0.00345 |

If the reactor feed of a gas phase reactor is comprised mostly of hydrogen and glycerol, at higher pressures and lower temperatures, extremely large quantities of hydrogen need to be removed from the product. If this hydrogen is not to be lost, it needs to be recycled. This recycling can be very costly. Reasonably larger mole fractions at higher temperatures are problematic because by-products rapidly form at temperatures greater than about 230° C. A system analyses reveals that preferred conditions for gas phase glycerol reaction. Optimization balances high versus low temperature to achieve high reaction rates (higher temperatures) without high by-product formation (lower temperature). Optimization also balances more-favorable equilibrium and reduced by-product formation (higher pressure) with maintaining reasonably high concentrations of glycerol in the feed (lower pressure). For the gas phase reaction, the optimal conditions for glycerol conversion without by-product formation tends to be 210 to 230° C. and 2 to 10 bars.

Figure 9:
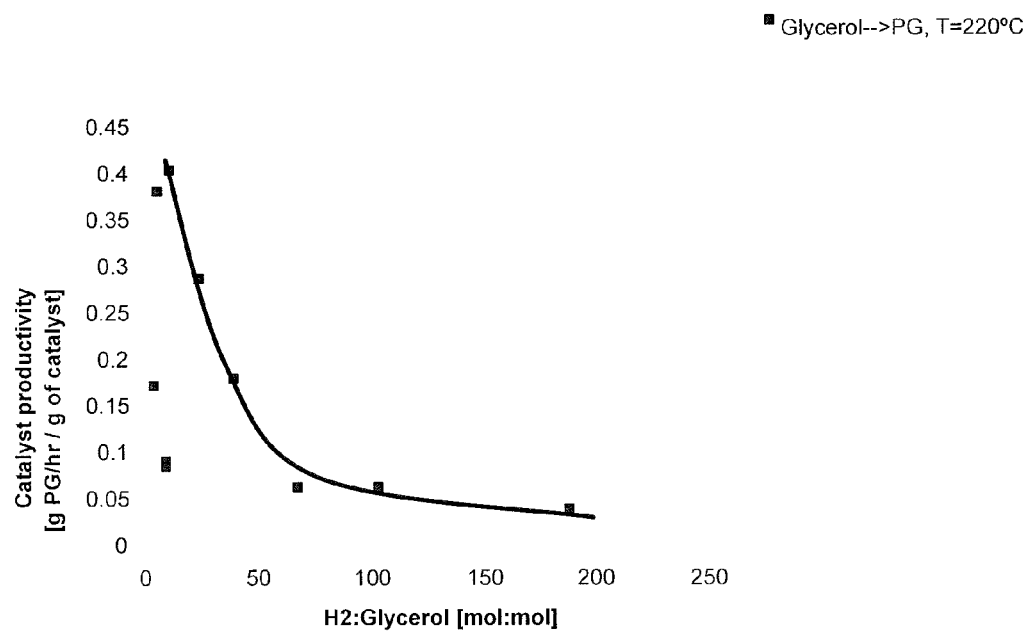
FIG. 9 shows glycerol to propylene glycol reaction effect of $H_2$: glycerol mole ratio on catalyst productivity at 220° C.

It is possible to operate gas phase reactors a very low concentrations of glycerol with the remainder predominantly hydrogen; however, a disadvantage of this approach is that the hydrogen rapidly carries the glycerol through the packed-bed reactor leading to low catalyst productivity and high catalyst costs. FIG. 9 and Table 11 summarize the impact of the molar ratio of hydrogen to glycerol on catalyst productivity (measured in grams of propylene glycol produced per hour per gram of catalyst in the packed-bed reactor). The maximum catalyst productivity is at a mole fraction of glycerol right below the dew point mole fraction of glycerol. The previously indicated preferred concentrations of glycerol expressed in terms of partial pressure indirectly specify the preferred molar ratios—the partial pressure specification is independent of total system pressure. All data is from 1 to 4 bars total pressure with most of the data at 2 bars pressure.

TABLE 11

Effect of $H_2$: Glycerol mole ratio on catalyst productivity for the glycerol to propylene glycol reaction.

| Reactor Temperature [° C.] | Pressure of Discharge [bar] | Hydrogen flowrate [L/min] | Glycerin flow rate [g/hr] | H2:Glyc [mol:mol] | Product flow rate [g/hr] | PG [wt %] | Catalyst Productivity [g PG/g cat] |
|---|---|---|---|---|---|---|---|
| 220 | 1 | 16.7 | 500.0 | 8.83 | 473.88 | 50.84 | 0.37 |
| 220 | 1 | 22.1 | 90.0 | 70.98 | 70.20 | 47.29 | 0.05 |
| 220 | 2 | 36.2 | 226.2 | 42.26 | 195.43 | 56.31 | 0.17 |
| 220 | 2 | 24.7 | 90.0 | 192.17 | 28.74 | 63.71 | 0.03 |
| 220 | 2 | 24.7 | 90.0 | 106.82 | 51.92 | 65.75 | 0.05 |
| 221 | 2 | 5.0 | 201.6 | 7.02 | 185.00 | 56.51 | 0.16 |

TABLE 11-continued

Effect of H₂: Glycerol mole ratio on catalyst productivity for the glycerol to propylene glycol reaction.

| Reactor Temperature [° C.] | Pressure of Discharge [bar] | Hydrogen flowrate [L/min] | Glycerin flow rate [g/hr] | H2:Glyc [mol:mol] | Product flow rate [g/hr] | PG [wt %] | Catalyst Productivity [g PG/g cat] |
|---|---|---|---|---|---|---|---|
| 220 | 2 | 5.0 | 127.2 | 12.14 | 99.96 | 51.20 | 0.08 |
| 221 | 2 | 5.0 | 127.2 | 12.40 | 97.68 | 49.38 | 0.07 |
| 220 | 4 | 29.9 | 226.2 | 26.72 | 258.84 | 69.47 | 0.28 |
| 220 | 4 | 22.1 | 500.0 | 13.70 | 386.76 | 65.83 | 0.39 |
| 238 | 1 | 2.5 | 99.5 | 8.78 | 71.56 | 27.31 | 0.03 |
| 241 | 1 | 2.5 | 99.5 | 6.58 | 99.90 | 27.73 | 0.04 |
| 240 | 1 | 5.0 | 198.0 | 6.83 | 191.23 | 31.35 | 0.09 |
| 237 | 2 | 5.0 | 198.0 | 9.91 | 125.00 | 35.53 | 0.07 |
| 236 | 2 | 5.0 | 198.0 | 9.79 | 126.80 | 40.56 | 0.08 |
| 240 | 2 | 5.0 | 198.0 | 7.52 | 170.80 | 31.80 | 0.08 |
| 240 | 4 | 5.0 | 198.0 | 12.70 | 95.23 | 30.91 | 0.05 |
| 240 | 4 | 10.0 | 390.6 | 7.63 | 336.24 | 51.36 | 0.27 |

It is possible to operate the gas phase reaction at higher pressures with high selectivity by making sure the partial pressure of glycerol does not exceed glycerol's dew point partial pressure. The advantage of this approach is to use high hydrogen pressures to push the equilibrium from acetol to propylene glycol and possibly reduce the need for some product purification unit operations and possibly eliminate the need to recycle acetol. Here, a process for converting glycerol to a product at high selectivity to propylene glycol and low selectivity to ethylene glycol preferably includes a reaction by: contacting a gas phase reaction mixture containing no liquid and containing a partial pressure of glycerol between 0.01 and 0.5 bars of glycerol and a total pressure between 25 and 500 bars with a heterogeneous catalyst at a temperature between 150° C. and 280° C. for a reaction time interval between 0.01 to 60 seconds. The solid catalyst preferably contains an element of the subgroups from Group I, Group VI, and/or Group VIII of the Periodic Table. Preferably, the partial pressure of glycerol is less than glycerol's dew point partial pressure in the reaction mixture and greater than one fourth the dew point partial pressure in the reaction mixture. More-preferably, the partial pressure of glycerol is greater than half the dew point partial pressure in the reaction mixture.

A gas phase reactor can be used to produce acetol where pressures beyond 1 bar little advantage—pressures lower than one bar can present a hazard if air leaks into the system. Here, a process for converting glycerol to a product at high selectivity to a mixture of acetol and propylene glycol and low selectivity to ethylene glycol preferably includes a reaction comprising: contacting a gas phase reaction mixture containing no liquid and containing a partial pressure of glycerol between 0.01 and 0.5 bars of glycerol and a partial pressure of hydrogen between 0.01 and 5 bars of hydrogen with a heterogeneous catalyst at a temperature between 150° C. and 280° C. for a reaction time interval between 0.01 to 60 seconds. The solid catalyst preferably contains an element of the subgroups from Group I, Group VI, and/or Group VIII. Preferably, the partial pressure of glycerol is less than glycerol's dew point partial pressure in the reaction mixture and greater than one fourth the dew point partial pressure in the reaction mixture. More-preferably, the partial pressure of glycerol is greater than half the dew point partial pressure in the reaction mixture. The slight amount of hydrogen in the system reduces by-product formation.

At 220° C. and 1 to 2 bars of pressure, the most preferred catalyst loading in the reactor is about 4 grams of catalyst per gram of propylene glycol produced per hour (a 4:1 ratio). Ratios from 1:0.4 to 1:0.05 are preferred. Higher catalyst loadings at the previously indicated preferred partial pressures of glycerol can lead to excessive product loss to by-products.

Use of Base Neutralization in Finishing Process

Reaction by-products from the gas phase reaction include multiple esters of propylene glycol and ethylene glycol. Ethylene glycol is at times observed in concentrations less than 2%. One method of purifying the reaction products is to convert the esters back to propylene glycol and ethylene glycol (along with corresponding acid) using a base (the reaction is effective at room temperature as well as temperatures higher than room temperature). After this hydrolysis reaction, the glycols can be evaporated/distilled from the salt formed from reaction of the base with the ester's acid. The glycols can than be purified by distillation.

Here, the preferred product purifying process includes the steps of: adding a base to the said propylene glycol product to achieve a pH greater than 8.0 and distilling the propylene glycol from the product having a pH greater than 8.0. The base is preferably selected from the group comprised of sodium hydroxide, potassium hydroxide, and calcium oxide.

Packed-Bed Reactor Design

Temperature control is most important to maximize reaction selectivity to acetol and/or propylene glycol. Reactors and methods known in the art can be used effectively, including but not limited to fluidized bed reactors and packed bed reactors. The preferred reactor is a novel reactor for use with highly exothermic reactions comprised of an outer shell containing U-tubes with an orientation such that the U-end of the U-Tubes is facing upward, said shell having an upper removable head where catalyst is loaded between shell and tubes from the top by removing the upper head. An inert packing may be placed in the lowest portion of the space between the shell and U-Tubes at a depth between 2 and 24 inches.

The design recommendation is to use a reactor sizing and loading of 4 lb of catalyst for each lb/hr of PG production. It is anticipated that at least 2000 lbs of propylene glycol (PG) is expected to be produced per pound of catalyst. Table 12 summarizes the catalyst loadings based on anticipated capacity.

TABLE 12

Summary of catalyst loading recommendations.

| Basis | Catalyst | Comment |
|---|---|---|
| 60M lb PG/yr | 30,000 lb cat | Total loading {0.25 lb PG/[lb cat × hr]} |
| 100M lb PG/yr | 50,000 lb cat | Total loading |
| " | 25,000 lb/reactor | Initial Loading Per Reactor, 75% full |
| " | 33,000 lb/reactor | Loading Per Reactor, 100% full |
| Fallback Capacity | 100,000 lb cat | Catalyst loading if all 3 reactors full |

An initial total catalyst loading of 30,000 lb (assumes 0.25 lb PG/[lb cat×hr])) (4 lb catalyst per lb/hr of PG production) may be appropriate if the initial capacity is targeted at 60 million lb per year.

One design uses three reactors arranged to operate in series with each reactor capable of holding 33,000 lb of catalyst when full and with the intent of only operating two in series at any time. Initially, each reactor would be 75% full and catalyst would be added as the initial loading deactivates—catalyst will be added until the reactor is full of catalyst. When catalyst activity is too low to meet production capacity, the first reactor in the series will be removed from operation and the reserve reactor will be placed as the second reactor in series with an initial catalyst loading of 50-75%. Inert material should be used in the first reactor for initial startup. After this startup, no inert material should be required in any of the reactors because the catalyst will be sufficiently deactivated in the second reactor by the time it is placed first in the series. This is with the exception that inert packing is always to be placed in the bottom 6 inches of the reactor as it is in this location were dead spots might occur relative to flow.

The design recommendation on the reactors is for use of tube-and-shell heat exchanger reactors that have U-tube internals. The reactors should be configured with the U end of the tube upward and a flanged/removable head on this upward U-tube side. Catalyst is to be loaded from the top with precautions taken to assure catalyst level is even through out all the spaces between U-tubes. More catalyst can be added to the reactor (added to top of catalyst bed) as the reaction proceeds. An upward flow is recommended. The packing is on the shell side (not tube side).

The desired catalyst loading to provide an ultimate capacity of 100 million lb/yr of PG production is summarized in Table 13 and can be met with 3, 6, or 9 reactors at the sizes and configurations indicated.

TABLE 13

Summary of reactor configuration options to meet catalyst capacity. Assumes ¾ inch tubes with wall-to-wall spacing of 1 inch in triangular configuration.

| # Reactors | Length of Shell (ft) | Diameter of Shell (ft) | Description |
|---|---|---|---|
| 3 | 12' | 7.5 | 3 in series |
| 3 | 16' | 6.5 | 3 in series |
| 6 | 12' | 5.3 | Two sets of 3 in series |
| 6 | 16' | 4.6 | Two sets of 3 in series |
| 9 | 12' | 4.3 | Three sets of 3 in series |
| 9 | 16' | 3.8 | Three sets of 3 in series |

Using these specifications for reactors and a design intended to use 2 of 3 reactors in series, the design productivity ratio is 0.25 [lb PG/lb cat–hr]), but the system is capable of producing at "worst case" rates of 0.125 [lb PG/lb cat–hr]). This should be an ample safety factor to guarantee the design capacity.

Reactor Sizing—

The catalyst density is 111 lb/ft$^3$ (some error exists due to the non-dry nature of the catalysts, all masses assume that free liquids are removed but catalyst surfaces are moist). This translates to 33,300 lb/111 lb/ft$^3$, or 300 cubic feet of void volume per reactor. In tube-and-shell heat exchanger design with ¾" OD tubes on a 1" (wall-to-wall) triangular spacing, the void volume is estimated to be 83%. Assuming a slight packing inefficiency, a value of 75% void volume (shell volume available for packing, not occupied by tubes) is warranted. Thus, the volume of the shell (not including heads) should be 400 cubic feet.

An area of 400 cubic feed divided by 12 ft length (length of heat exchanger) translates to a void cross sectional areas of 33.3 ft$^2$ (400/12) or shell cross sectional areas (75% void volume) of 44.4 ft$^2$. This translates to a shell of 7.5 ft ID. The area in inches is 6400 in$^2$. Under the assumption of one tube for each 1.33 in$^2$, each heat exchanger would have 4828 tubes of ¾" OD (or 2414 U-tubes). Results from these calculations are summarized in Table 12.

Data on Catalyst Loading—

Figure 10:
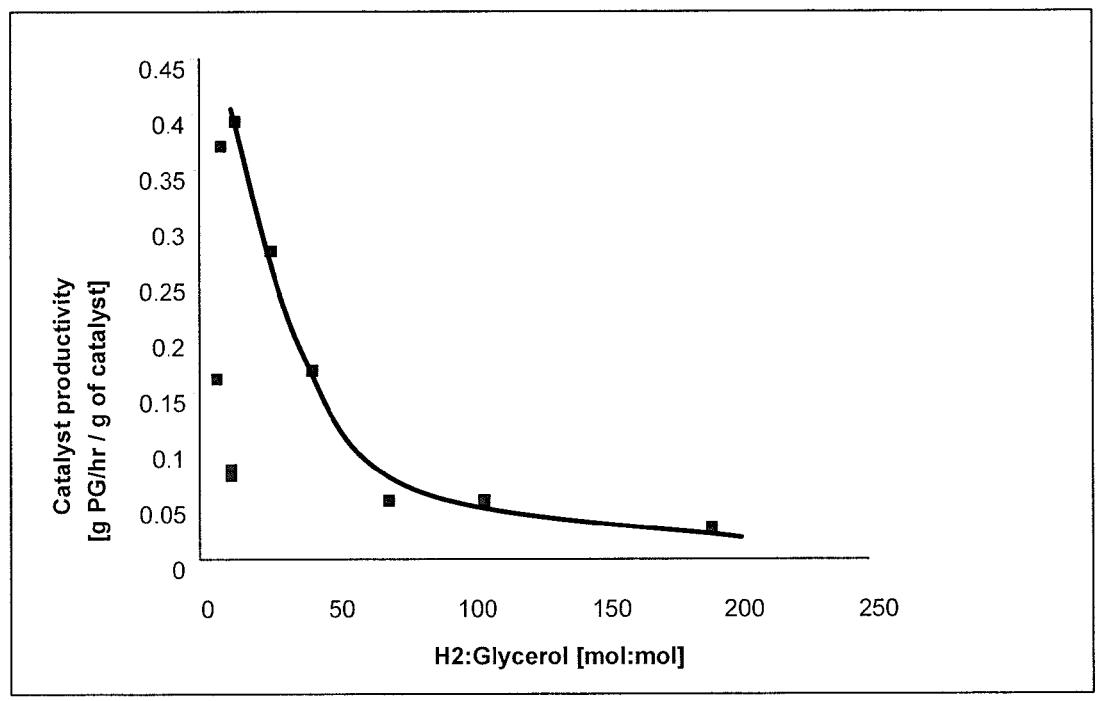
FIG. 10 shows glycerol to PG reaction: effect of H2:Glycerol mole ratio on catalyst productivity at 220° C.

FIG. 10 shows results from such a reactor as modeled by COBRA software. For the multi-tube reactor, the catalyst productivity is approximately 625 grams of PG/hr divided by 3.6 kg of catalyst (or 0.174 [lb PG/lb cat–hr]). Comparing COBRA to multi-tube reactor performances, it is concluded that the performance in the current multi-tube reactor is limited by the evaporator and not the amount of catalyst. In addition, acetol recycle is expected to increase catalyst productivity by up to 50%. For these reasons, the recommended catalyst loading is 0.25 [lb PG/lb cat–hr] (4 lb of catalyst per 1 [lb/hr] PG production) rather than 0.174 [lb PG/lb cat–hr].

The mass of catalyst loading is calculated by taking the hourly production rate of PG and multiplying this number times 4 hrs. The hours of operation in a year are assumed at 360×24=8640 hours/yr or a plant capacity of 11,574 lb/hr. This translates to a catalyst loading of 46,300 lb for a 100 million lb/yr facility (11,574×4).

One type of design is for three reactors in series with each reactor capable of holding 33,000 lb of catalyst when full. The intent is to only operate two reactors in series at any time. Initially, each reactor would be 75% full and catalyst would be added as the initial loading deactivates. Table 13 summarizes six different ways to achieve this capacity.

Comments on Shell-Side Loading—

Figure 11C:
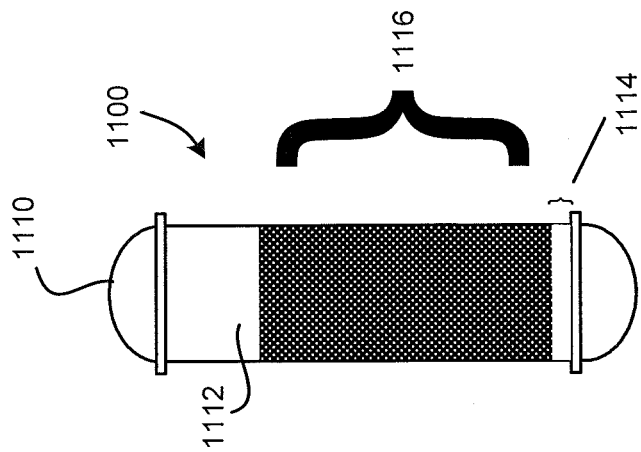
FIGS. 11A, 11B and 11C show an example of reactor configuration.
Figure 11B:
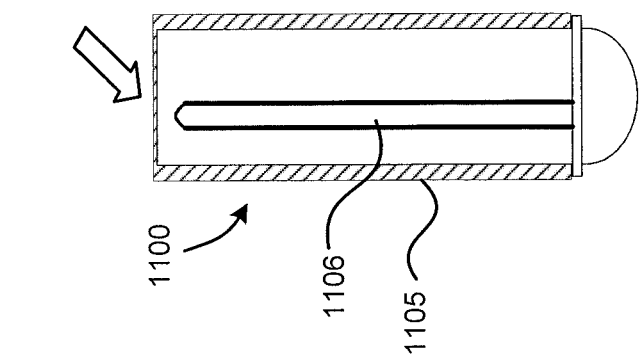
Figure 11A:
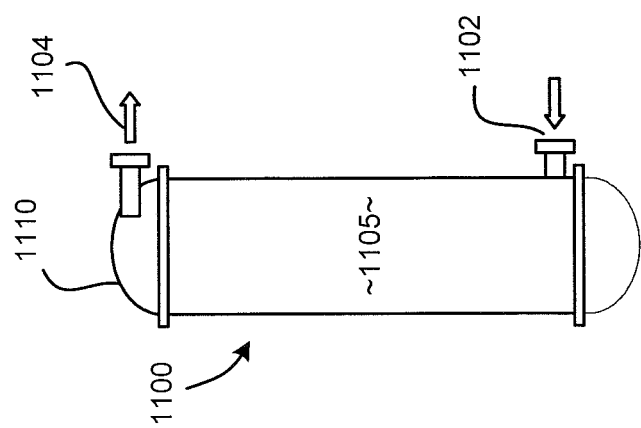

A shell side loading of the reactor is possible because access from the top (U-side) allows easy loading of catalyst in the reactor allows inert packing to be strategically placed in the reactor. As shown in FIG. 11A, a shell-side reactor 1100 has a feed or inlet port 1102, that within the confines of reactor 1100 is in fluidic communication with exit or outlet port 1104. the reactor 1100 is used to perform the reactions describe above. As shown in FIG. 11B, the reactor 1100 has an outer shell 1105 that may be filled with one or more U-tubes 1106 for use as heat exchangers within a jacket 1108 A top 1110 (see FIG. 11A) may be removed to permit top access to the jacket and to the reactor interior. core. As show in FIG. 11 C. the reactor interior core 1112 may be filled with material including a bed of insert packing 1114 beneath a catalyst 1116, as described above. The advantages of this configuration over a tube-side loading are as follows:

- Up to a 5× reduction in reactor size is attained.
- Potential problems of by-passing and hot-spot development that can occur with tube reactors is all but eliminated.
- The pressure drop is considerably less.
- Filling catalyst in the tubes is considerably easier. Basically 2-6 shells are loaded with catalyst as opposed to 50,000 tubes (5×volume).

EXAMPLE 4

Pilot Scale Reactor Validation

Pilot scale reactor validation of the "shell-side" approach to packing the catalyst was successful and is considered fully scalable. This pilot reactor had a 2" ID with three 0.5" OD tubes in which oil was circulated to cool the reactor. Various operational aspects validated in the pilot production run included the following:

Temperatures can be controlled (25% inert loading was used, may or may not be necessary) with distances up to 1 inch from the wall of the tube to the furthest catalyst particles. Conversions were good and product profiles consistent with previous runs.

The system can operate with adequately low pressure drops.

One problem that developed was some (~5%) glycerol vapors were by-passing the catalysts and were in the product stream at conditions that previously exhibited less than 0.2% glycerol in the product. The by-passing was believed due to the low depth of the reactor bed packing—a packing of 3.75 feet of catalyst (5 feet of catalyst plus inert) as compared to 16 or 24 feet of catalyst (axial length of packing) in the cobra reactors. In a commercial facility, the depth may be 18 to 24 feet, and so, this bypass issue should be resolved.

Figures 12A, 12B:
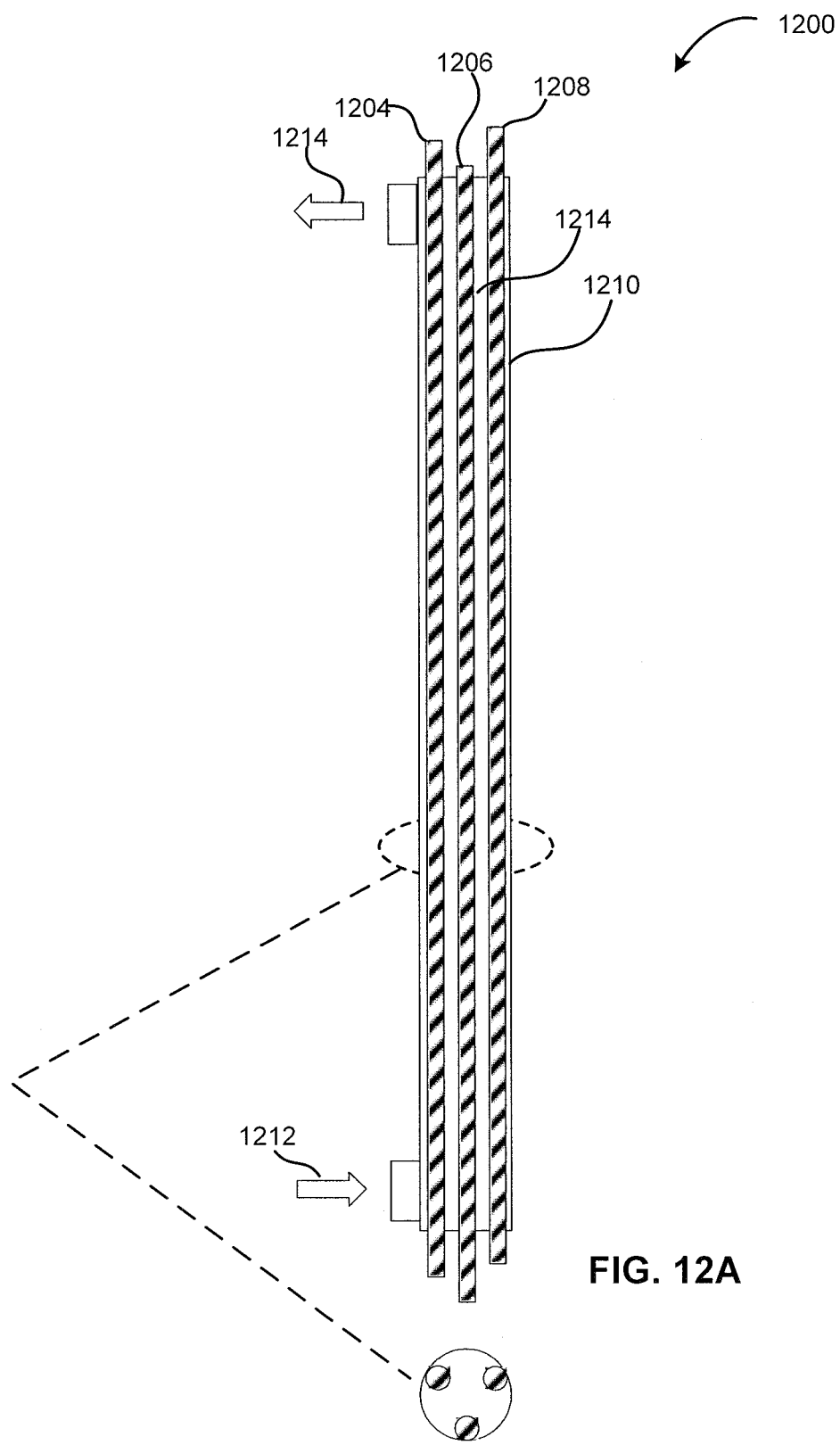
FIG. 12A illustrates a pilot scale reactor.
FIG. 12B shows the cross-sectional view of the reactor.

FIG. 12 shows an axial and radial cross section of the pilot reactor 1200. The heat transfer in this reactor is over the same dimensions as heat exchange in the reactors specified above The reactor 1200 is fully scalable by simply increasing the shell diameter while keeping the spacing of the oil-filled circulating heat exchange tubes 1204, 1206, 1208 the same. The shell surface 1210 was insulated against heat loss. Reactor feed inlet 1212 and reactor feed outlet 1214 are in fluidic communication through a catalyst-packed chamber 1214.

The following three pilot reactors have been demonstrated in the laboratory with the first two having tube loadings and the last having a shell loading:

16' pilot using ¾" OD tube: 1500 g catalyst loading.
10' pilot using 1.0" OD tube: 2280 g catalyst loading.
5' pilot using 2.0" ID shell and 3 tubes: 3600 g catalyst loading Even at the pilot scale, the shell-side loading was much easier to work with and the reactor had a much lower pressure drop.

A preferred pressure drop from compressor exit to compressor entrance is 14.7 psi. The pilot scale system has operated for several days at a pressure drop of 7.5 psi. This validates the capability to operate at the needed low pressure drop.

In the pilot facility, about 5 psi pressure drop is across the evaporator, about 0.5 psi pressure drop is across the 5 feet of reactor packing, and about 2 psi pressure drop is from the condenser and entrance/exit effects. Increasing the bed depth to 20 should result in 2 psi. A further doubling of space velocity through the packing should increase the pressure drop to 4 psi. A 4 psi pressure drop through packing is consistent with targeted commercial reactor operation.

The 5 psi pressure drop in the evaporator is consistent with a "long" travel path of at least 100 feet of evaporator tubing. The targeted evaporator pressure drop for the commercial system is 3 psi. The targeted pressure drop for all other aspects (condenser, flash vessels, and entrance effects) is 3 psi.

Composition of Antifreeze Product from Glycerol of Biodiesel Facility

Biodiesel is one type of product that can be produced from a fatty acid glycerin refinery. After a conventional biodiesel methanolysis reaction, the methoxylation catalyst is preferably removed by filtration from a slurry reaction system. Other methods, such as centrifugation or precipitation, may be used to remove soluble catalysts from the glycerol byproduct of the biodiesel methanolysis reaction process. These processes are compatible with either batch or continuous operation. Methods known in the art may be used to convert the batch process procedures (described herein) to flow process procedures. Hydrogenation of the glycerol is performed to prepare a glycerol byproduct that preferably contains, on a water-free basis, from 0.5% to 60% glycerol, and 20% to 85% propylene glycol. More preferably, the glycerol byproduct contains on a water-free basis from 10% to 35% glycerol, and 40% to 75% propylene glycol. Also, as the preferred antifreeze of this invention is prepared from the crude natural glycerol byproduct of the $C_1$ to $C_4$ alkyl alcohol alcoholysis of a glyceride, the more preferable product also contains 0.2% to 10% C1 to C4 alkyl alcohol and 0 to 5% salt of the neutralized alcoholysis catalyst (more preferably 0.2 to 5% salt).

The glycerol conversion reactions have been observed to form a residue by-product. When this residue is soluble in the

TABLE 14

Pilot Scale Results

| Glycerol flow rate (L/hr) | Shell-and-Tube reactor #1 (¾" OD; 16 ft. length) | | Shell-and-Tube reactor #2 (1" OD; 10 ft. length) | | Tube-cooled reactor (2" ID; 5 ft. length) | |
|---|---|---|---|---|---|---|
| | Color | Unconverted Glycerol (%) | Color | Unconverted Glycerol (%) | Color | Unconverted Glycerol (%) |
| 0.3 | clear | 0 | — | — | — | — |
| 0.5 | clear | 0 | — | — | — | — |
| 0.75 | clear | 0 | clear | 0 | clear | (not include) |
| 0.8 | Very slightly yellow | 1 | clear | 0 | clear | ~3 |
| 1 | Light yellow | 5 | Very slightly yellow | (not include) | clear | ~8 |
| 1.3 | Yellow | 8 | Light yellow | (not include) | clear | ~14 | antifreeze product, the preferred application is to add it to the antifreeze product. The antifreeze may contain 1% to 15% of this residue by-product.

While the antifreeze products of this invention are commonly referred to as antifreeze, these same mixtures or variations thereof may be used as deicing fluids and anti-icing fluids.

When the reaction is run without hydrogen, acetol will form. This mixture can then subsequently (or in parallel) react in a packed-bed flow reactor in the presence hydrogen to be converted to propylene glycol. This process has the advantage that the larger reactor does not contain pressurized hydrogen.

The processes and procedures described in this text are generally applicable to refined glycerol as well as crude glycerol.

The catalyst used for most of the process development was a Sud-Chemie powder catalyst at 30 m$^2$/g surface area, 45% CuO, 47% Cr$_2$O$_3$, 3.5% MnO$_2$ and 2.7% BaO. Also used was a Sud-Chemie tablet catalyst at 49% CuO, 35% Cr$_2$O$_3$, 10% SiO$_2$ and 6% BaO. Also used was a Sud-Chemie powder catalyst at 54% CuO and 45%.

EXAMPLE 5

Processing of Biodiesel Byproduct

Crude glycerol obtained as a by product of the biodiesel industry was used instead of refined glycerol. Biodiesel is produced using alcoholysis of bio-renewable fats and oils. The composition of feedstock 104 used in this example had an approximate composition as follows: glycerol (57%), methyl alcohol (23%), and other materials (soaps, residual salts, water) (20%). The above feedstock was reacted in the presence of hydrogen and catalyst to form a mixture containing propylene glycol. The reaction proceeded using 10 grams of the crude feedstock, 5% by weight of catalyst, and a hydrogen overpressure of 1400 kPa. The following Table 15 presents compositions after reacting in a closed reactor (with topping off of hydrogen) for 24 hours at a temperature of 200° C. The copper chromium catalyst used in this Example was reduced in presence of hydrogen at a temperature of 300° C. for 4 hours prior to the reaction.

TABLE 15

Summary of catalyst performances based on 10 grams of crude glycerol.

|  | Initial Loading (g) | Best Possible (g) | Final Product (g) |
| --- | --- | --- | --- |
| Crude Glycerol | 5.7 | 0 | 0.8 |
| Acetol | 0 | 0 | 0 |
| Propylene glycol | 0 | 4.6 | 3.1 |
| Water | 1 | 2.1 | 2.6 |

Reactive-Separation to Prepare Acetol and Other Alcohols

Figure 13:
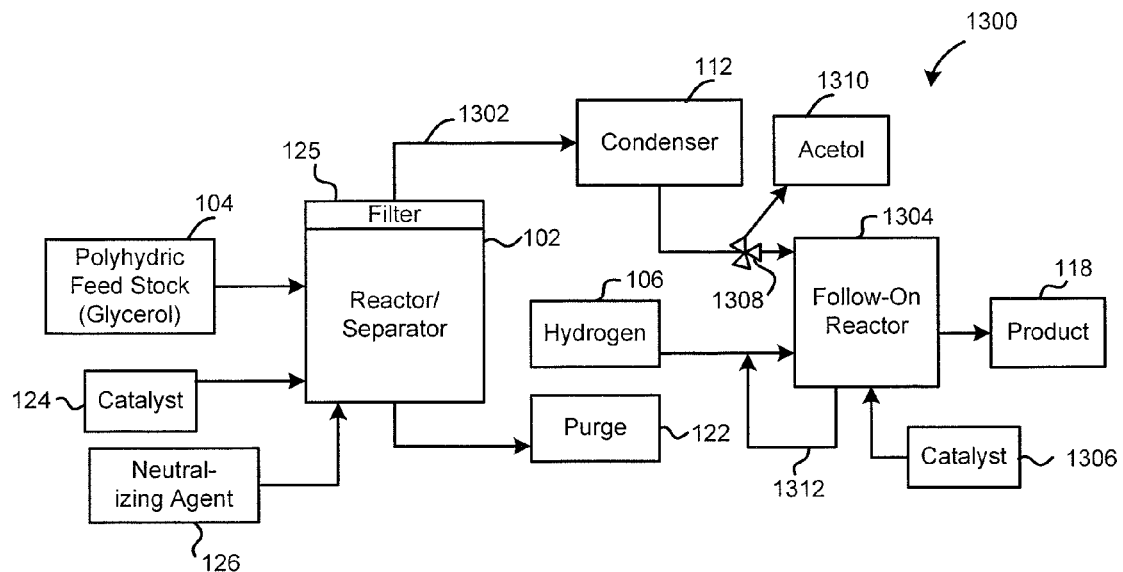
FIG. 13 illustrates a packed-bed reactor with optional gas feed to evaporator.

As an alternative to reacting to form propylene glycol by use of the process equipment 100 shown in FIG. 1, FIG. 13 shows a modified version of the process equipment that has been previously described. Process equipment 1300 is useful for forming acetol or other alcohols having boiling points less than about 200° C. Dehydration is the preferred reaction method, but cracking reactions may be used with feed stocks containing sugars or polysaccharides having carbon numbers greater than 3.

In general, the process equipment 1300 is used for converting a three-carbon or greater sugar or polysaccharide to an alcohol dehydration product having a boiling point less than about 200° C. By way of example, a sugar or polysaccharide-containing feedstock with less than 50% by weight water is combined with a catalyst that is capable of dehydrating glycerol to form a reaction mixture. The reaction mixture is heated to a temperature ranging from 170° to 270° C. over a reaction time interval ranging from 0.5 to 24 hours at a pressure ranging from 0.2 to 25 bar.

One method of converting glycerol to acetol is in a semi-batch slurry reaction where glycerol is continuously added and acetol is removed as a vapor. In this method, residence time may be less than 0.5 hours, depending upon catalyst loading. Also, pressures as low as 0.02 bar will successfully pull off the acetol as a vapor that can then be condensed to form a liquid product.

The preferred reaction conditions for conversion of glycerol to form acetol include a process temperature ranging from 170° C. to 270° C., and this is more preferably from 180° C. to 240° C. The preferred reaction time exists within a range from 0.5 to 24 hours. Heterogeneous catalysts that are known to be effective for dehydration may be used, such as nickel, copper, zinc, copper chromium, activated alumina and others known in the art. The preferred reaction pressure exists within a range from 0.2 to 25 bar, and this is more preferably from The 0.5 to 3 bar. The feedstock may contain from 0% to 50% and more preferably 0 to 15% water by weight.

By these instrumentalities, glycerol may be dehydrated to acetol. Selective formation of acetol is documented for the copper-chromium catalyst by Examples 5 through 7 below. The same reaction conditions with different catalyst are effective for forming other alcohol products where the products have fewer alcohol functional groups than do the reagents. Fractional isolation of intermediates through reactive-distillation is particularly effective to increase yields and the embodiments is inclusive of processes to produce a range of products including but not limited to 1,3 propanediol and acrolein.

FIG. 13 shows process equipment 1300 for the selective conversion of glycol to acetol. In FIG. 13, identical numbering is used for the same components that have been previously described with respect to FIG. 1. The reactor separator 102 as shown in FIG. 13 functions as a dehydration reactor. The polyhydric feedstock 104 and catalyst 124 enter reactor-separator 102 for a reaction that is limited to the dehydration step 204 of FIG. 2 by the absence of hydrogen, and in consequence the hydrogenation step 208 does not occur at this time. The dominant reaction product is acetol 202. Volatile fractions including acetol vapor exit the reactor-separator 102 through an overhead intermediate line 1302 and liquefy in condenser 112. A follow-on reactor 1304 functions as a hydrogenolysis reactor that accepts acetol and other liquids from condenser 112, and contacts the acetol with hydrogen to form propylene glycol as product 118. The catalyst 1306 may be the same as or different from catalyst 126. The condenser 112 preferably operates at a temperature ranging from 25° C. to 150° C. and this is more-preferably from 25° C. to 60° C. It will be appreciated that the condenser 112 may be eliminated or positioned downstream of the follow-on reactor 1304 if the follow-on reactor 1304 operates as a vapor phase reactor.

When the process equipment 1300 is operating in mode of producing propylene glycol product 118, a hydrogen recycle loop 1312 recycles excess hydrogen from the follow-on reactor 1304. This step preferably recycles unused hydrogen from the condenser back to the subsequent step reaction mixture. The reaction time of this subsequent step reaction exists within a range from 0.2 to 24 hours and more-preferably exists within a range from 1 to 6 hours.

The acetol that is delivered through intermediate line 1302 to condenser 112 is optimally diverted through three way valve 1308 to provide an acetol product 1310.

EXAMPLE 6

Stepwise Production of Acetol then Propylene Glycol

Glycerol was reacted in the presence of copper chromium catalyst in two steps to form a mixture containing propylene glycol. In Step 1, relatively pure acetol was isolated from glycerol in absence of hydrogen at a reaction pressure of 98 kPa (vac). In Step 2, the acetol from Step 1 was further reacted in presence of hydrogen to propylene glycol at 1400 kPa hydrogen over pressure using similar catalyst that is used for the formation of acetol. The catalyst used in the step 1 of this Example is used in the condition in which they arrived and the catalyst used in the Step 2 was reduced in presence of hydrogen at a temperature of 300° C. for 4 hours prior to the reaction.

The following table presents composition of the final product in Step 1 and Step 2.

TABLE 16

Example reaction conditions for converting glycerol to propylene glycol.

| | Initial Loading (g) | Best Possible (g) | Final Product (g) |
|---|---|---|---|
| Step 1: Formation and isolation of acetol intermediate from glycerol using copper-chromite catalyst. Catalyst - 5% unreduced powder Cu/Cr, Reaction time - 1.5 hr at 220° C. and 3 hr at 240° C., Reaction Pressure - 98 kPa (vac). | | | |
| Glycerol | 36.8 | 0 | 3.6 |
| Acetol | 0 | 29.6 | 23.7 |
| Propylene glycol | 0 | 0 | 1.7 |
| Water | 0 | 7.2 | 6.9 |
| Step 2: Formation of propylene glycol from acetol intermediate from Step 1 using same catalyst. Catalyst - 5% reduced powder Cu/Cr, Reaction time - 12 hr, Reaction Temperature - 190° C., Reaction Pressure - 1400 kPa. | | | |
| Glycerol | 0 | 0 | 0 |
| Acetol | 4.5 | 0 | 0 |
| Propylene glycol | 0 | 4.6 | 4.3 |

EXAMPLE 7

Batch Versus Semi Batch Processing

Glycerol was reacted in presence of copper chromium catalyst to form acetol by each of two process modes: batch and semi batch. Relatively pure acetol was isolated from glycerol in absence of hydrogen at a reaction pressure of 98 kPa (vac). In this reaction 92 grams of glycerol would form a maximum of 74 grams acetol at the theoretical maximum 100% yield. Either process mode produced a residue. When dried, the residue was a dark solid coated on the catalyst that was not soluble in water.

In semi-batch operation, the reactor was provisioned with catalyst and glycerol was fed into the reactor at a uniform rate over a period of about 1.25 hours. In batch operation, all of the glycerol and catalyst was loaded into the reactor at the start of the reaction. The following results show the semi-batch reactive-distillation has higher yields and selectivities than batch. The higher catalyst loading provided higher yields and selectivities. It was observed that the catalyst activity decreased with reaction time and the amount of residue increased with reaction time.

The copper chromium catalysts used in this Illustrative Example were used in the condition in which they arrived. Process runs were made using the conditions described in Table 17.

TABLE 17

Comparison of Semi-Batch (Continuous) Reactive-distillation and Batch Reactive-distillation. Formation and isolation of acetol intermediate from glycerol using copper-chromite catalyst. Catalyst - 5% unreduced copper chromium powder Reaction conditions:

Reaction Pressure-98 kPa (vac)
Reaction temperature-240° C.
Reaction complete time-2 hr
Glycerol feed rate-33.33 g/hr for Semi-Batch Reactions
The following three reactions were conducted:

RXN 8.1 - Semi-Batch reaction at 5% catalyst loading
RXN 8.2 - Semi-Batch reaction at 2.5% catalyst loading
RXN 8.3 - Batch reaction 5% catalyst loading Table 18 provides reaction details of reaction conditions RXN 8.1 of Table 17. Initial loading of glycerol was 54.29 grams; glycerol in distillate was 4.91 grams; residue was 3.80 grams, and the amount of glycerol reacted was 49.38 grams.

TABLE 18

Mass balance details on RXN 8.1. Catalyst loading was 5%.

| | Reacted Glycerol (g) | Best possible (g) | Distillate (g) |
|---|---|---|---|
| Glycerol | 49.38 | 0 | 3.64 |
| Acetol | 0 | 39.71 | 35.99 |
| Propylene glycol | 0 | 0 | 1.65 |
| Water | 0 | 9.66 | 5.79 |

Table 19 provides details of reaction 8.2: Initial loading of glycerol was 52.8 grams; glycerol in distillate was 3.85 grams; residue was 4.91 grams; and the amount of glycerol reacted was 48.95 grams.

TABLE 19

Mass balance details on RXN 8.2. Catalyst loading was 2.5%.

| | Reacted Glycerol (g) | Best possible (g) | Distillate (g) |
|---|---|---|---|
| Glycerol | 48.95 | 0 | 3.85 |
| Acetol | 0 | 39.37 | 33.51 |
| Propylene glycol | 0 | 0 | 1.63 |
| water | 0 | 9.58 | 6.24 |

Table 20 provides details of reaction 8.2: Initial loading of glycerol was 42.48 grams; glycerol in distillate was 3.64 grams; residue was 5.68; and the amount of glycerol reacted was 33.16 grams.

TABLE 20

Mass balance details on RXN 8.3. Catalyst loading was 5%.

|  | Reacted Glycerol (g) | Best possible (g) | Distillate (g) |
|---|---|---|---|
| Glycerol | 36.80 | 0 | 3.64 |
| Acetol | 0 | 29.60 | 23.73 |
| Propylene glycol | 0 | 0 | 1.67 |
| water | 0 | 7.2 | 6.99 |

As reported n the following examples, various studies were performed to assess the ability to control the residue problem.

EXAMPLE 8

Control of Residue by Water Content of Feedstock

Glycerol was reacted in presence of copper chromium catalyst to form acetol at conditions similar to Illustrative Example 5 with 2.5% catalyst loading and in a semi-batch reactor method. Water was added to the glycerol to evaluate if water would decrease the accumulation of the water-insoluble residue. Table 21 summarizes the conversion results. These data illustrate that a small amount of water reduces the tendency for residue to form. The copper chromium catalyst used in this Illustrative Example was used in the condition in which they arrived.

TABLE 21

Impact of water on residue formation.
Catalyst - 2.5% unreduced powder Cu/Cr
Reaction Pressure-98 kPa (vac)
Reaction temperature-240° C.
Reaction complete time-2 hr
Glycerol feed rate-33.33 g/hr

| Water (wt %) | Initial Glycerol (g) | Glycerol in Distillate (g) | Best Possible of Acetol (g) | Acetol in Distillate (g) | Residue (g) | Conversion (%) | Residue:Initial Glycerol Ratio |
|---|---|---|---|---|---|---|---|
| 0% | 52.8 | 3.85 | 39.37 | 33.51 | 4.91 | 92.71% | 9.30% |
| 5% | 53.26 | 4.93 | 38.87 | 35.23 | 3.47 | 90.74% | 7.02% |
| 10% | 56.25 | 8.55 | 38.36 | 34.48 | 3.45 | 84.80% | 6.13% |
| 20% | 55.52 | 9.67 | 36.87 | 33.13 | 2.95 | 82.58% | 5.31% |

EXAMPLE 9

Control of Residue by Catalyst Loading

Glycerol was reacted in presence of copper chromium catalyst to form acetol in a semi-batch reactor method. The impact of lowering catalyst loadings was evaluated to determine the impact of catalyst loading on acetol yield and residue formation. Table 22 summarizes the conversion results. These data illustrate that the formation of residue may be autocatalytic—it increases more than linearly with increasing throughput of glycerol over the catalyst. Also, the selectivity decreases with increasing throughput of glycerol over a fixed catalyst loading in the reactor.

The copper chromium catalyst used in this Illustrative Example was used in the condition in which they arrived.

TABLE 22

Impact of catalyst to glycerol throughput ratio on residue formation.
Catalyst - 1.25 g unreduced powder Cu/Cr
Reaction Pressure-98 kPa (vac)
Reaction temperature-240° C.
Glycerol feed rate-33.33 g/hr

| Reaction | Catalyst % | Total feed of Glycerol (g) | Residue (g) | Conversion (%) | Acetol Selectivity | Residue:Reacted-Glycerol Ratio |
|---|---|---|---|---|---|---|
| 1 | 5% | 27.15 | 1.9 | 90.96% | 90.62% | 7.70% |
| 2 | 2.50% | 52.80 | 4.91 | 92.71% | 85.11% | 10.03% |
| 3 | 1.67% | 77.22 | 7.54 | 90.44% | 76.94% | 10.76% |
| 4 | 1.25% | 105.68 | 11.7 | 89.23% | 73.50% | 12.11% |
| 5 | 0.83% | 151.69 | 17.18 | 86.87% | 59.76% | 13.03% |

EXAMPLE 10

Regeneration of Catalyst

This example illustrates the stability of the copper chromium catalyst for the formation of propylene glycol from acetol. The following were the approximate initial conditions: 4.5 grams of acetol, 2 wt % of catalyst, and a hydrogen overpressure of 1400 kPa. The following table presents compositions after reacting in a closed reactor (with topping off of hydrogen) for 4 hours at a reaction temperature of 185° C. The copper chromium catalyst was reduced in presence of hydrogen at a temperature of 300° C. for 4 hours prior to the reaction. The catalyst after each run was filtered from the reaction products, washed with methanol and then dried in a furnace at temperature of 80° C. This regenerated catalyst was reused in the subsequent reactions. Similar regeneration procedure is repeated 10 times and the results are summarized in Table 23. These data illustrate the ability to reuse catalyst for the hydrogenation of acetol.

The copper chromium catalyst used in this Illustrative Example was reduced in presence of hydrogen at a temperature of 300° C. for 4 hours prior to the reaction.

TABLE 23

Summary of catalyst performances based on 4.5 grams of acetol.

|  | Acetol (g) | Propylene glycol (g) | Lactaldehyde (g) |
|---|---|---|---|
| initial | 4.5 | 0 | 0 |
| Run 1 | 0.5 | 3.62 | 0.51 |
| Run 2 | 0.29 | 3.85 | 0.56 |
| Run 3 | 0.19 | 4.19 | 0.53 |
| Run 4 | 0.07 | 4.41 | 0.47 |
| Run 5 | 0.05 | 4.42 | 0.49 |
| Run 6 | 0.05 | 4.39 | 0.51 |
| Run 7 | 0 | 4.41 | 0.36 |
| Run 8 | 0.24 | 4.2 | 0.42 |
| Run 9 | 0.27 | 4.2 | 0.43 |
| Run 10 | 0.21 | 4.11 | 0.4 |

EXAMPLE 11

Ability to Reuse Catalyst of Acetol-Forming Reaction

This example illustrates that a powder catalysts may be treated or reactivated by hydrogen treatment, but also that one powder catalyst that contains 54% CuO and 45% $Cr_2O_3$ has better reuse properties than does another powder catalyst at 30 $m^2/g$ surface area, 45% CuO, 47% $Cr_2O_3$, 3.5% $MnO_2$ and 2.7% BaO. For the powder catalyst at 54% CuO and 45% $Cr_2O_3$, the data of Table 24 demonstrate that residue formation rate is similar to that of the powder catalyst at 30 $m^2/g$ surface area, 45% CuO, 47% $Cr_2O_3$, 3.5% $MnO_2$ and 2.7% BaO (Table 23). The data of Table 25 demonstrate the 54% CuO and 45% $Cr_2O_3$ catalyst can be used repeatedly (at laboratory scale, 1-3% of the catalyst was not recovered from reaction to reaction). The data of Table 26 demonstrate that reuse is more difficult with the 45% CuO, 47% $Cr_2O_3$, 3.5% $MnO_2$ and 2.7% BaO Catalyst.

TABLE 24

Impact of catalyst to glycerol throughput ratio on residue formation. The catalyst in this table is a powder catalyst at 54% CuO and 45% $Cr_2O_3$. This compares to the catalyst of Table 13 which is a powder catalyst at 30 $m^2/g$ surface area, 45% CuO, 47% $Cr_2O_3$, 3.5% $MnO_2$ and 2.7% BaO. Reactions were semi-batch.
Catalyst - 1.25 g unreduced Cu/Cr, powder catalyst at 54% CuO and 45% Cr2O3.
Pressure-98 kPa (vac); Temperature-240° C.; Glycerol feed rate-33.33 g/hr

| Reaction | Catalyst (%) | Total feed of Glycerol (g) | Residue (g) | Conversion (%) | Acetol Selectivity (%) | [Residue]:[Reacted-Glycerol] Ratio |
|---|---|---|---|---|---|---|
| 1 | 5% | 26.35 | 1.95 | 89.82% | 87.05% | 8.36% |
| 2 | 2.50% | 53.38 | 5.41 | 91.05% | 82.01% | 11.13% |
| 3 | 1.25% | 102.98 | 12.36 | 89.07% | 78.86% | 13.47% |

TABLE 25

Impact of reuse on powder catalyst at 54% CuO and 45%.
Catalyst is loaded at 5% and is unreduced.
Catalyst - 2.5 g unreduced Cu/Cr, powder catalyst at 54% CuO and 45% $Cr_2O_3$.
Pressure-98 kPa (vac); Temperature-240° C.; Glycerol feed rate-33.33 g/hr

|  | Total feed of Glycerol (g) | Residue (g) | Conversion (%) | Acetol Selectivity (%) | Residue: Initial-Glycerol Ratio |
|---|---|---|---|---|---|
| Fresh | 52.77 | 3.96 | 89.82% | 87.05% | 7.51% |
| Reused 1 | 52.16 | 4.11 | 91.28% | 88.52% | 7.88% |
| Reused 2 | 51.72 | 3.89 | 91.74% | 88.56% | 7.53% |
| Reused 3 | Catalysts still could be recovered | | | | |

TABLE 26

Impact of reuse on powder catalyst at 30 m2/g surface area, 45% CuO, 47% Cr2O3, 3.5% MnO2 and 2.7% BaO.
Catalyst - 2.5 g unreduced powder Cu/Cr
Pressure-98 kPa (vac); Temperature-240° C.; Glycerol feed rate-33.33 g/hr

|  | Total feed of Glycerol (g) | Residue (g) | Conversion (%) | Acetol Selectivity (%) | Residue: Initial-Glycerol Ratio |
|---|---|---|---|---|---|
| Fresh | 54.29 | 3.80 | 90.95% | 90.62% | 7.01% |
| Reused 1 | 53.13 | 3.99 | 88.92% | 88.80% | 7.51% |
| Reused 2 | Catalyst could not be recovered-residue was totally solidified | | | | |

The two catalysts at initial condition performed about the same for the acetol forming reaction; however, the 45% CuO, 47% $Cr_2O_3$, 3.5% $MnO_2$ and 2.7% BaO catalyst at a loading of lesser than 5% formed a different type of residue that was more resistant to catalyst recovery. For both catalysts, it was generally observed that as reactions proceeded, the reaction rates tended to reduce. At the end of the semi-batch reaction a digestion of the mixture was induced by stopping the feed and allowing the reaction to proceed for about 30 min to an hour—during this digestion the volume of the reaction mixture decreased and the residue became more apparent.

For the 54% CuO and 45% $Cr_2O_3$ catalyst, the residue tends to be stable. This residue takes a solid form in room temperature and a slurry form at the reaction temperature during the long period of reaction time. A methanol wash readily removed the residue, allowing the catalyst to be reused multiple times. The solid was soft and tacky in nature and readily dissolved in methanol to form slurry. The catalyst was washed with methanol until the wash was clear and then the catalyst was dried in a furnace at 80° C. to remove the methanol. The physical appearance of this catalyst after washing was similar to that of the new catalyst.

In the case of 45% CuO, 47% $Cr_2O_3$, 3.5% $MnO_2$ and 2.7% BaO catalyst the residue was, however, different. In the case of 5% catalyst loading, residue started foaming on the catalyst at 30 min after total glycerin was fed, i.e., 30 minutes into the reaction. Once foaming started, a methanol wash was not effective for removing the residue from the catalyst. If the reaction was stopped prior to commencement of foaming, the methanol was effective in removing the residue from the catalyst. When catalyst loading less than 2.5%, the residue started foaming while the glycerin was still being fed to the reactor, and the catalyst could not be recovered at end of the reaction. The 54% CuO and 45% Cr2O3 catalyst produced a residue that is a solid at room temperature.

These trends in reuse of catalyst are applicable to conditions for conversion of glycerin to acetol as well as the "single-pot" conversion of glycerin to propylene glycol.

EXAMPLE 12

Lactaldehyde Mechanism

Acetol was hydrogenated in presence of copper chromium catalyst to form a mixture containing propylene glycol. The following were the approximate initial conditions: 10 grams of acetol, 2 wt % of catalyst, and a hydrogen overpressure of 1400 kPa. The following table presents compositions after reacting in a closed reactor (with topping off of hydrogen) for 4 hours at a reaction temperature of 190° C. Table 27 shows the effect of reaction temperature on the formation of propylene glycol from acetol. The data illustrate that good conversions are attainable at 190° C. The data illustrate that the co-product (likely undesirable) of lactaldehyde is produced at lower selectivities at temperatures greater than 150° C. Optimal temperatures appear to be 190° C. or higher. The copper chromium catalyst used in this Illustrative Example was reduced in presence of hydrogen at a temperature of 300° C. for 4 hours prior to the reaction.

TABLE 27

Summary of catalyst performances based on 9 grams of acetol. The pressure is 1400 kPa with a 5% catalyst loading.

| Temperature C. | Acetol (g) | Propylene glycol (g) | Lactaldehyde (g) |
|---|---|---|---|
| Unreacted | 10 | 0 | 0 |
| 50 | 8.25 | 1.86 | 0.13 |
| 100 | 5.74 | 3.93 | 0.47 |
| 150 | 3.10 | 4.31 | 2.82 |
| 180 | 1.64 | 7.90 | 0.89 |
| 190 | 0.56 | 9.17 | 0.58 |

Table 28 shows the effect of initial water content in the reactants on the formation of propylene glycol from acetol. The data illustrate that water can improve yields to propylene glycol. Selectivity to propylene glycol decreases as the reaction goes beyond 10-12 hrs.

TABLE 28

Summary of catalyst performances based on different initial loadings of water. The reaction temperature is 190° C., at a pressure of 1400 kPa, a 5% catalyst loading and a reaction time of 24 hours. The total loading of water with acetol is 10 grams.

| Water (% wt) | Acetol (g) | Propylene glycol (g) | Lactaldehyde (g) |
|---|---|---|---|
| 10 | 0.47 | 7.65 | 0 |
| 20 | 0.22 | 5.98 | 0.7 |
| 50 | 0.22 | 4.35 | 0.27 |

Table 29 shows the effect of initial catalyst concentration on the formation of propylene glycol from acetol. The data illustrate that the highest yields are attained at the higher catalyst loadings.

TABLE 29

Summary of catalyst performances based on 4.5 grams of acetol. The reaction temperature is 190° C., at a pressure of 1400 kPa, and no added water.

| Catalyst Concentration (wt %) | Reaction Time (h) | Acetol (g) | Propylene glycol (g) | Lactaldehyde (g) |
|---|---|---|---|---|
| Initial | — | 4.5 | 0 | 0 |
| 5% | 4 | 0.29 | 4.46 | 0.22 |
| 2% | 4 | 0.14 | 4.27 | 0.2 |
| 1% | 4 | 1.32 | 3.45 | 0.29 |
| 0.5% | 4 | 1.56 | 3.14 | 0.32 |
| 1% | 6 | 0.58 | 3.78 | 0.25 |
| 0.5% | 6 | 1.27 | 3.29 | 0.33 |

Reactive-Separation with Gas Stripping

The use of the reactor-separator 102 is very effective for converting glycerol to acetol as illustrated by the foregoing Examples. These examples illustrate, for example, the effective use of water and catalyst loading to reduce formation of residue. Two disadvantages of the reactions were the formation of residual and operation at small amounts of vacuum.

The most preferred approach overcomes the vacuum operation by using a gas to strip the acetol from solution. Thus, the process equipment operates at a more optimal pressure, such as slightly over atmospheric pressure, to make advantageous use of fugacity (partial pressures) for the selective removal of vapor from the reaction mixture. The stripper gases may be inert gases such as nitrogen to strip out the acetol. Steam may also be used to strip out the acetol. The most-preferred stripping gas is hydrogen.

Use of hydrogen at pressures slightly above atmospheric pressure strips the acetol and/or propylene glycol from solution as they are formed. In addition, the preferred hydrogen stripper gas keeps the catalyst reduced and provides reaction paths that prevent residue formation and/or react with the residue to form smaller molecules that also strip from solution. The reactions that strip the residue may include use of additional catalysts that are known to be effective for catalytic cracking, and the use of such stripper gas in combination with catalytic cracking catalysts is referred to herein as a strip-crack process. The hydrogen is preferably either recycled in the reactor or compressed with the acetol for a second reaction at higher pressure.

The preferred reaction process includes a first reactor. In the first reactor, the first product and alternative product are removed as vapor effluents from a liquid reaction where a sufficient hydrogen pressure is present to reduce the residue formation by at least 50% as compared to the residue formation rate without hydrogen present. The preferred hydrogen partial pressures are between 0.2 and 50 bars, more preferably between 0.5 and 30 bars, and most preferably between 0.8 and 5 bars.

To achieve higher conversions to the alternative product, the first product may be reacted in a second reactor that is operated at higher partial pressures of hydrogen. In the second reactor, the partial pressure of hydrogen is at least twice the partial pressure of hydrogen in the second reactor, more preferably the partial pressure of hydrogen is at least four times the partial pressure of hydrogen in the first reactor.

The respective temperatures of the first and second reactors are preferably above the normal boiling point of the first product.

The use of hydrogen has an additional advantage of reducing residue that tends to deactivate catalysts which are useful in the disclosed process. In this sense, the hydrogen may be used as the gas purge or stripper gas, as well as a reagent in the first reactor. For example, in the cracking of petroleum to gasoline, it is well-known that hydrogen reduces the formation of residue that tends to deactivate of the catalyst; however, the use of hydrogen is more expensive than cracking of petroleum in the absence of hydrogen. In petroleum industry practice, considerable catalytic cracking is performed in the absence of hydrogen with product loss, and specialized equipment is devoted to regenerating the deactivated catalyst. Those other practices differ from the presently disclosed use of hydrogen stripper gas that is sufficient to reduce catalyst deactivation, but is sufficiently low in amount and amount/pressure to allow the non-hydrogen cat-cracking to dominate, e.g., at a pressure less that 50 bars, while the reaction is underway.

Figure 14:
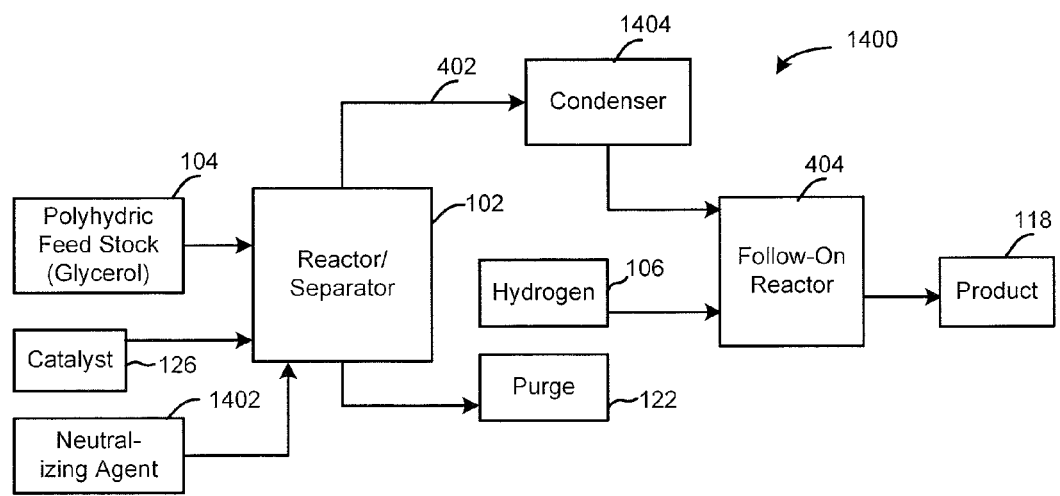
FIG. 14 is a schematic block flow diagram illustrating a preferred packed-bed reactor system including recycle of product to improve temperature control and purification of the reactor effluent in a separator.

FIG. 14 shows one embodiment that implements these concepts. Process equipment 1400 the process where the hydrogen is compressed to proceed to the second reaction. In FIG. 14, like numbering is maintained with respect to identical elements as shown in FIG. 13. The reaction process proceeds as described with respect to FIG. 13, except low pressure hydrogen stripper gas 1402 is applied to reactor separator 102, for example, at a pressure slightly above atmospheric pressure. Although some of this gas does result in the production of propylene glycol, the stripping of acetol is predominant. A mixture of acetol, propylene glycol and water vapor flows through overhead line 402 to condenser 1404, which condenses the vapors for use in the follow-on reactor 404. The extant hydrogen is optionally supplemented by additional hydrogen 106 to establish the preferred reaction conditions discussed above.

Figure 15:
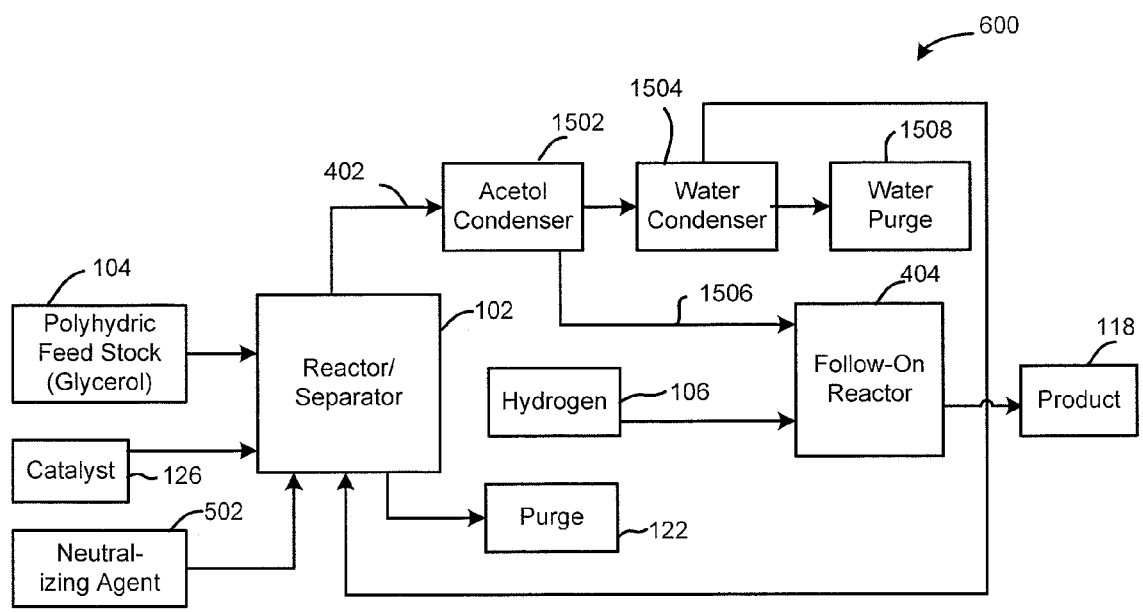
FIG. 15 is a schematic block flow diagram illustrating a preferred packed-bed reactor system including recycle of product to improve temperature control and purification of the reactor effluent in a separator.

FIG. 15 shows another embodiment, that of process equipment 1500. In FIG. 6, like numbering is maintained with respect to identical elements as shown in FIG. 13. In process equipment 1500, the effluent through intermediate overhead line 402 is applied to a series of condensers 1502, 1504 that decrease in their relative temperatures to condense first the acetol in acetol condenser 1504 and then water in water condenser 1504. The condensed acetol is applied to line 1506, e.g., by pumping at the requisite pressure, for delivery to the follow-on reactor 404. Water effluent from water condenser 604 is discharged as water purge 1508.

The hydrogen pressures (or partial pressures) for this process in the respective reactor vessels may be lower than is required for "good" hydro-cracking and/or hydrogenolysis but sufficient to stop catalyst deactivation.

In addition to reactor configurations, other methods known in the science for reducing residue (often an oligomer) formation is the use of a solvent. The solvent can reduce residue formation or dissolve the residue therein extending catalyst life. Solvents are preferably not reactive liquids. Supercritical solvents, such as carbon dioxide, have also been demonstrated as effective for extending catalyst life when residue formation otherwise coats the catalyst.

EXAMPLE 13

Reactor Performance

The following tables summarize additional process results from the pilot reactor.

TABLE 30

Effect of Temperature and Pressure on the Formation of Propylene Glycol from Acetol.

| Reactor Temperature [° C.] | Pressure of Discharge [bar] | Acetol [wt %] | PG [wt %] | [PG:Acetol Mass Ratio] | Reactor Temperature [K] | 1000/T(K) | Log [PG:Acetol Mass Ratio] |
|---|---|---|---|---|---|---|---|
| 202 | 1 | 20.14 | 36.94 | 1.83 | 475.15 | 2.10 | 0.26 |
| 211 | 1 | 14.88 | 36.83 | 2.48 | 484.15 | 2.07 | 0.39 |
| 241 | 1 | 13.43 | 21.1 | 1.57 | 514.15 | 1.94 | 0.20 |
| 241 | 1 | 12.74 | 20.37 | 1.60 | 514.15 | 1.94 | 0.20 |
| 201 | 1 | 13.17 | 53.15 | 4.04 | 474.15 | 2.11 | 0.61 |
| 240 | 1 | 30.18 | 29.81 | 0.99 | 513.15 | 1.95 | −0.01 |
| 242 | 1 | 31.76 | 33.19 | 1.05 | 515.15 | 1.94 | 0.02 |
| 239 | 1 | 24.54 | 26.38 | 1.07 | 512.15 | 1.95 | 0.03 |
| 184 | 2 | 8.56 | 57.3 | 6.69 | 457.15 | 2.19 | 0.83 |
| 202 | 2 | 11.12 | 43.14 | 3.88 | 475.15 | 2.10 | 0.59 |
| 217 | 2 | 14.32 | 39.91 | 2.79 | 490.15 | 2.04 | 0.45 |
| 220 | 2 | 21.64 | 30.28 | 1.40 | 493.15 | 2.03 | 0.15 |
| 221 | 2 | 14.92 | 43.51 | 2.92 | 494.15 | 2.02 | 0.46 |
| 218 | 2 | 13.86 | 46.82 | 3.38 | 491.15 | 2.04 | 0.53 |
| 221 | 2 | 12.91 | 38.95 | 3.02 | 494.15 | 2.02 | 0.48 |
| 243 | 2 | 44.84 | 41.83 | 0.93 | 516.15 | 1.94 | −0.03 |
| 201 | 4 | 6.03 | 55.15 | 9.15 | 474.15 | 2.11 | 0.96 |
| 203 | 4 | 4.68 | 60.46 | 12.92 | 476.15 | 2.10 | 1.11 |
| 244 | 4 | 19.14 | 22.64 | 1.18 | 517.15 | 1.93 | 0.07 |
| 203 | 4 | 5.29 | 59.89 | 11.32 | 476.15 | 2.10 | 1.05 |

TABLE 30-continued

Effect of Temperature and Pressure on the Formation of Propylene Glycol from Acetol.

| Reactor Temperature [° C.] | Pressure of Discharge [bar] | Acetol [wt %] | PG [wt %] | [PG:Acetol Mass Ratio] | Reactor Temperature [K] | 1000/ T(K) | Log [PG:Acetol Mass Ratio] |
|---|---|---|---|---|---|---|---|
| 242 | 4 | 10.3 | 34.33 | 3.33 | 515.15 | 1.94 | 0.52 |
| 240 | 4 | 11.34 | 43.86 | 3.87 | 513.15 | 1.95 | 0.59 |

TABLE 31

Equilibrium constant and Gibbs free energy values for the Propylene Glycol to Acetol Reaction.

| Reactor Temperature [K] | $P_{TOTAL}$ [bar] | YAC | YPG | YPG/ YAC | $YH_2$ | YPG/ (YAC * YH2) | K eq, YPG/ (YAC * YH2 * P) | $\Delta G$ [J/gmol] |
|---|---|---|---|---|---|---|---|---|
| 450 | 2 | 0.06 | 0.85 | 13.55 | 0.89 | 17.84 | 7.58 | −7579.35 |
| 454 | 2 | 0.11 | 0.80 | 7.52 | 0.89 | 10.58 | 4.21 | −5430.3 |
| 457 | 2 | 0.11 | 0.82 | 7.73 | 0.89 | 10.59 | 4.33 | −5572.69 |
| 454 | 2 | 0.11 | 0.81 | 7.31 | 0.89 | 10.08 | 4.09 | −5319.77 |
| 453 | 2 | 0.11 | 0.83 | 7.88 | 0.89 | 10.61 | 4.41 | −5590.19 |
| 456 | 2 | 0.10 | 0.84 | 8.85 | 0.86 | 12.18 | 5.13 | −6197.74 |
| 480 | 2 | 0.15 | 0.72 | 4.69 | 0.86 | 7.63 | 2.74 | −4020.2 |
| 476 | 1 | 0.18 | 0.64 | 3.61 | 0.74 | 7.68 | 4.91 | −6296.26 |
| 475 | 1 | 0.21 | 0.68 | 3.30 | 0.74 | 6.52 | 4.44 | −5887.31 |
| 477 | 4 | 0.09 | 0.70 | 7.54 | 0.93 | 11.58 | 2.03 | −2812.42 |
| 470 | 4 | 0.05 | 0.83 | 15.78 | 0.92 | 20.60 | 4.27 | −5675.43 |
| 493 | 2 | 0.18 | 0.60 | 3.39 | 0.85 | 6.58 | 1.99 | −2811.27 |
| 489 | 2 | 0.17 | 0.59 | 3.45 | 0.85 | 6.89 | 2.02 | −2865.41 |
| 510 | 1 | 0.34 | 0.33 | 0.98 | 0.74 | 4.00 | 1.32 | −1188.67 |
| 510 | 2 | 0.33 | 0.33 | 1.00 | 0.85 | 3.55 | 0.59 | 2243.48 |
| 513 | 2 | 0.22 | 0.40 | 1.80 | 0.85 | 5.31 | 1.06 | −250.565 |
| 515 | 2 | 0.21 | 0.34 | 1.63 | 0.85 | 5.61 | 0.96 | 158.9529 |
| 512 | 1 | 0.30 | 0.34 | 1.11 | 0.73 | 4.51 | 1.52 | −1779.86 |
| 515 | 4 | 0.06 | 0.18 | 2.97 | 0.85 | 19.69 | 0.87 | 577.815 |
| 515 | 4 | 0.18 | 0.44 | 2.44 | 0.85 | 6.46 | 0.72 | 1427.368 |
| 514 | 4 | 0.08 | 0.36 | 4.43 | 0.92 | 13.55 | 1.21 | −805.754 |
| 513 | 4 | 0.12 | 0.52 | 4.45 | 0.92 | 9.34 | 1.21 | −814.523 |
| 513 | 4 | 0.13 | 0.51 | 3.97 | 0.91 | 8.47 | 1.09 | −362.552 |
| 512 | 4 | 0.22 | 0.57 | 2.59 | 0.92 | 4.94 | 0.71 | 1478.77 |

TABLE 32

Equilibrium constant and Gibbs free energy values for the Acetol to Propylene Glycol Reaction.

| Reactor Temperature [K] | $P_{TOTAL}$ [bar] | YAC | YPG | YPG/ YAC | $YH_2$ | YPG/ (YAC * YH2) | K eq, YPG/ (YAC * YH2 * P) | $\Delta G$ [J/gmol] |
|---|---|---|---|---|---|---|---|---|
| 457 | 2 | 0.05 | 0.30 | 6.52 | 0.86 | 25.62 | 3.79 | −5059.54 |
| 475 | 1 | 0.10 | 0.17 | 1.79 | 0.48 | 21.56 | 3.70 | −5171.55 |
| 475 | 2 | 0.05 | 0.21 | 3.78 | 0.85 | 21.74 | 2.23 | −3172.27 |
| 474 | 1 | 0.07 | 0.28 | 3.93 | 0.75 | 18.54 | 5.25 | −6534.36 |
| 476 | 4 | 0.03 | 0.31 | 11.02 | 0.92 | 39.06 | 2.99 | −4333.03 |
| 474 | 4 | 0.03 | 0.27 | 8.91 | 0.92 | 35.93 | 2.43 | −3496.03 |
| 476 | 4 | 0.02 | 0.31 | 12.58 | 0.92 | 44.10 | 3.43 | −4879.46 |
| 484 | 1 | 0.07 | 0.18 | 2.41 | 0.72 | 19.24 | 3.37 | −4888.07 |
| 490 | 2 | 0.06 | 0.17 | 2.71 | 0.87 | 18.49 | 1.56 | −1817.34 |
| 493 | 2 | 0.10 | 0.14 | 1.36 | 0.87 | 11.56 | 0.78 | 993.421 |
| 494 | 2 | 0.07 | 0.20 | 2.84 | 0.87 | 16.25 | 1.64 | −2022.76 |
| 491 | 2 | 0.06 | 0.21 | 3.29 | 0.87 | 18.02 | 1.89 | −2607.56 |
| 494 | 2 | 0.06 | 0.18 | 2.94 | 0.84 | 19.18 | 1.74 | −2272.33 |
| 516 | 2 | 0.18 | 0.16 | 0.91 | 0.84 | 6.72 | 0.54 | 2634.137 |
| 513 | 1 | 0.14 | 0.13 | 0.96 | 0.64 | 11.44 | 1.50 | −1725.2 |
| 515 | 1 | 0.13 | 0.14 | 1.02 | 0.71 | 10.53 | 1.43 | −1536.74 |
| 514 | 1 | 0.06 | 0.09 | 1.53 | 0.71 | 22.71 | 2.15 | −3267.45 |
| 514 | 1 | 0.06 | 0.10 | 1.56 | 0.71 | 22.91 | 2.19 | −3342.4 |
| 512 | 1 | 0.12 | 0.12 | 1.05 | 0.72 | 11.85 | 1.45 | −1576.73 |
| 515 | 4 | 0.05 | 0.16 | 3.25 | 0.91 | 22.41 | 0.90 | 472.8089 |
| 513 | 4 | 0.06 | 0.21 | 3.77 | 0.92 | 19.43 | 1.03 | −110.795 |
| 517 | 4 | 0.12 | 0.14 | 1.15 | 0.92 | 9.05 | 0.31 | 4975.326 |

TABLE 33

Effect of temperature and pressure on total byproducts of the glycerol to propylene glycol reaction.

| Reactor Temperature [° C.] | Pressure of Discharge [bar] | Reactor Temperature [K] | Total Byproducts [wt %] |
|---|---|---|---|
| 220 | 1 | 493 | 6.29 |
| 220 | 1 | 493 | 15.50 |
| 238 | 1 | 511 | 45.29 |
| 241 | 1 | 514 | 42.06 |
| 240 | 1 | 513 | 21.31 |
| 220 | 2 | 493 | 4.27 |
| 220 | 2 | 493 | 4.98 |
| 220 | 2 | 493 | 5.37 |
| 221 | 2 | 494 | 11.36 |
| 220 | 2 | 493 | 18.65 |
| 221 | 2 | 494 | 16.46 |
| 237 | 2 | 510 | 22.32 |
| 236 | 2 | 509 | 22.01 |
| 240 | 2 | 513 | 29.03 |
| 220 | 4 | 493 | 4.54 |
| 220 | 4 | 493 | 1.58 |
| 240 | 4 | 513 | 17.59 |

TABLE 34

Effect of the residence time on byproducts of the glycerol to propylene glycol reaction.

| Reactor Temperature [° C.] | Pressure of Discharge [bar] | Hydrogen flowrate [(ft^3)/min] | Reactor Volume [ft^3] | Residence time [min] | Total Byproducts [wt %] | Water Content [wt %] |
|---|---|---|---|---|---|---|
| 220 | 1 | 0.59 | 0.05 | 0.08 | 6.29 | 18.52 |
| 220 | 1 | 0.78 | 0.05 | 0.06 | 15.5 | 21.96 |
| 220 | 2 | 1.28 | 0.05 | 0.04 | 4.27 | 18.93 |
| 220 | 2 | 0.87 | 0.05 | 0.06 | 4.98 | 13.71 |
| 220 | 2 | 0.87 | 0.05 | 0.06 | 5.37 | 13.30 |
| 221 | 2 | 0.18 | 0.05 | 0.28 | 11.36 | 20.74 |
| 220 | 2 | 0.18 | 0.05 | 0.28 | 18.65 | 21.01 |
| 221 | 2 | 0.18 | 0.05 | 0.28 | 16.46 | 23.29 |
| 220 | 4 | 1.06 | 0.05 | 0.05 | 4.54 | 17.16 |
| 220 | 4 | 0.78 | 0.05 | 0.06 | 1.58 | 15.73 |
| 238 | 1 | 0.09 | 0.05 | 0.56 | 45.29 | 15.72 |
| 241 | 1 | 0.09 | 0.05 | 0.56 | 42.06 | 14.02 |
| 240 | 1 | 0.18 | 0.05 | 0.28 | 21.31 | 25.70 |
| 237 | 2 | 0.18 | 0.05 | 0.28 | 22.32 | 24.01 |
| 236 | 2 | 0.18 | 0.05 | 0.28 | 22.01 | 24.09 |
| 240 | 2 | 0.18 | 0.05 | 0.28 | 29.03 | 26.63 |
| 240 | 4 | 0.18 | 0.05 | 0.28 | 42.86 | 28.78 |
| 240 | 4 | 0.35 | 0.05 | 0.14 | 17.59 | 26.51 |

TABLE 35

Effect of the water content on byproducts of the glycerol to propylene glycol reaction.

| Reactor Temperature [° C.] | Pressure of Discharge [bar] | Water content [wt %] | Total Byproducts [wt %] |
|---|---|---|---|
| 220 | 1 | 18.52 | 6.29 |
| 220 | 1 | 21.96 | 15.5 |
| 240 | 1 | 25.7 | 21.31 |
| 220 | 2 | 18.93 | 4.27 |
| 220 | 2 | 13.71 | 4.98 |
| 220 | 2 | 13.3 | 5.37 |
| 221 | 2 | 20.74 | 11.36 |
| 220 | 2 | 21.01 | 18.65 |
| 221 | 2 | 23.29 | 16.46 |
| 237 | 2 | 24.01 | 22.32 |
| 236 | 2 | 24.09 | 22.01 |
| 240 | 2 | 26.63 | 29.03 |
| 220 | 4 | 17.16 | 4.54 |
| 220 | 4 | 15.73 | 1.58 |
| 240 | 4 | 26.51 | 17.59 |

TABLE 36

Effect of temperature and pressure on byproducts of the propylene glycol to acetol reaction.

| Reactor Temperature [° C.] | Pressure of Discharge [bar] | Reactor Temperature [K] | Total Byproducts [wt %] |
|---|---|---|---|
| 203 | 1 | 476 | 18.94 |
| 202 | 1 | 475 | 10.41 |
| 237 | 1 | 510 | 27.84 |
| 239 | 1 | 512 | 21.51 |
| 177 | 2 | 450 | 3.13 |
| 178 | 2 | 451 | 5.11 |
| 184 | 2 | 457 | 4.02 |
| 181 | 2 | 454 | 4.53 |
| 182 | 2 | 455 | 3.99 |
| 183 | 2 | 456 | 3.35 |
| 207 | 2 | 480 | 10.84 |
| 220 | 2 | 493 | 16.62 |
| 216 | 2 | 489 | 18.99 |
| 237 | 2 | 510 | 25.22 |
| 240 | 2 | 513 | 27.74 |
| 242 | 2 | 515 | 35.03 |
| 204 | 4 | 477 | 8.79 |
| 197 | 4 | 470 | 1.82 |
| 242 | 4 | 515 | 30.03 |
| 242 | 4 | 515 | 19.7 |
| 241 | 4 | 514 | 39.39 |
| 240 | 4 | 513 | 21.98 |
| 240 | 4 | 513 | 25.35 |
| 239 | 4 | 512 | 16.43 |

TABLE 37

Effect of the residence time on byproducts of the propylene glycol to acetol reaction.

| Reactor Temperature [° C.] | Pressure of Discharge [bar] | Hydrogen flowrate [L/min] | Hydrogen flowrate [(ft^3)/min] | Reactor Volume [ft^3] | Residence time [min] | Total Byproducts [wt %] |
|---|---|---|---|---|---|---|
| 177 | 2 | 5.0 | 0.2 | 0.05 | 0.28 | 3.13 |
| 178 | 2 | 5.0 | 0.2 | 0.05 | 0.28 | 5.11 |
| 184 | 2 | 5.0 | 0.2 | 0.05 | 0.28 | 4.02 |
| 181 | 2 | 5.0 | 0.2 | 0.05 | 0.28 | 4.53 |
| 182 | 2 | 5.0 | 0.2 | 0.05 | 0.28 | 3.99 |
| 183 | 2 | 5.0 | 0.2 | 0.05 | 0.28 | 3.35 |
| 203 | 1 | 2.5 | 0.1 | 0.05 | 0.56 | 18.94 |
| 202 | 1 | 5.0 | 0.2 | 0.05 | 0.28 | 10.41 |
| 207 | 2 | 5.0 | 0.2 | 0.05 | 0.28 | 10.84 |

TABLE 37-continued

Effect of the residence time on byproducts of the propylene glycol to acetol reaction.

| Reactor Temperature [° C.] | Pressure of Discharge [bar] | Hydrogen flowrate [L/min] | Hydrogen flowrate [(ft^3)/min] | Reactor Volume [ft^3] | Residence time [min] | Total Byproducts [wt %] |
|---|---|---|---|---|---|---|
| 204 | 4 | 2.5 | 0.1 | 0.05 | 0.56 | 8.79 |
| 197 | 4 | 5.0 | 0.2 | 0.05 | 0.28 | 1.82 |
| 220 | 2 | 5.0 | 0.2 | 0.05 | 0.28 | 16.62 |
| 216 | 2 | 5.0 | 0.2 | 0.05 | 0.28 | 18.99 |
| 239 | 1 | 2.5 | 0.1 | 0.05 | 0.56 | 21.51 |
| 237 | 1 | 5.0 | 0.2 | 0.05 | 0.28 | 27.84 |
| 237 | 2 | 5.0 | 0.2 | 0.05 | 0.28 | 25.22 |
| 240 | 2 | 5.0 | 0.2 | 0.05 | 0.28 | 27.74 |
| 242 | 2 | 5.0 | 0.2 | 0.05 | 0.28 | 35.03 |
| 242 | 4 | 5.0 | 0.2 | 0.05 | 0.28 | 30.03 |
| 242 | 4 | 5.0 | 0.2 | 0.05 | 0.28 | 19.7 |
| 241 | 4 | 5.0 | 0.2 | 0.05 | 0.28 | 39.39 |
| 240 | 4 | 10.0 | 0.4 | 0.05 | 0.14 | 21.98 |
| 240 | 4 | 10.0 | 0.4 | 0.05 | 0.14 | 25.35 |
| 239 | 4 | 2.5 | 0.1 | 0.05 | 0.56 | 16.43 |

TABLE 38

Effect temperature and pressure on byproducts of the acetol to propylene glycol reaction.

| Reactor Temperature [° C.] | Pressure of Discharge [bar] | Reactor Temperature [K] | Total Byproducts [wt %] |
|---|---|---|---|
| 202 | 1 | 475 | 8.12 |
| 211 | 1 | 484 | 12.63 |
| 241 | 1 | 514 | 34.39 |
| 241 | 1 | 514 | 38.74 |
| 201 | 1 | 474 | 4.48 |
| 240 | 1 | 513 | 17.74 |
| 242 | 1 | 515 | 29.39 |
| 239 | 1 | 512 | 16.08 |
| 184 | 2 | 457 | 2.94 |
| 202 | 2 | 475 | 6.11 |
| 217 | 2 | 490 | 13.58 |
| 220 | 2 | 493 | 14.83 |
| 221 | 2 | 494 | 12.56 |
| 218 | 2 | 491 | 12.27 |
| 221 | 2 | 494 | 14.79 |
| 243 | 2 | 516 | 29.96 |
| 201 | 4 | 474 | 5.2 |
| 203 | 4 | 476 | 4.04 |
| 244 | 4 | 517 | 41.81 |
| 203 | 4 | 476 | 6.63 |
| 242 | 4 | 515 | 11.84 |
| 240 | 4 | 513 | 12.77 |

TABLE 39

Effect of the residence time on byproducts of the acetol to propylene glycol reaction.

| Reactor Temperature [° C.] | Pressure of Discharge [bar] | Hydrogen flowrate [L/min] | Hydrogen flowrate [(ft^3)/min] | Reactor Volume [ft^3] | Residence time [min] | Total Byproducts [wt %] |
|---|---|---|---|---|---|---|
| 184 | 2 | 5.0 | 0.18 | 0.05 | 0.28 | 2.94 |
| 202 | 1 | 2.5 | 0.09 | 0.05 | 0.56 | 8.12 |
| 201 | 1 | 5.0 | 0.18 | 0.05 | 0.28 | 4.48 |
| 202 | 2 | 5.0 | 0.18 | 0.05 | 0.28 | 6.11 |
| 201 | 4 | 2.5 | 0.09 | 0.05 | 0.56 | 5.20 |
| 203 | 4 | 2.5 | 0.09 | 0.05 | 0.56 | 4.04 |
| 203 | 4 | 5.0 | 0.18 | 0.05 | 0.28 | 6.63 |
| 211 | 1 | 2.5 | 0.09 | 0.05 | 0.56 | 12.63 |
| 217 | 2 | 5.0 | 0.18 | 0.05 | 0.28 | 13.58 |
| 220 | 2 | 5.0 | 0.18 | 0.05 | 0.28 | 14.83 |
| 221 | 2 | 5.0 | 0.18 | 0.05 | 0.28 | 12.56 |
| 218 | 2 | 5.0 | 0.18 | 0.05 | 0.28 | 12.27 |
| 221 | 2 | 5.0 | 0.18 | 0.05 | 0.28 | 14.79 |
| 241 | 1 | 2.5 | 0.09 | 0.05 | 0.56 | 34.39 |
| 241 | 1 | 2.5 | 0.09 | 0.05 | 0.56 | 38.74 |
| 240 | 1 | 5.0 | 0.18 | 0.05 | 0.28 | 17.74 |
| 242 | 1 | 5.0 | 0.18 | 0.05 | 0.28 | 29.39 |
| 239 | 1 | 10.0 | 0.35 | 0.05 | 0.14 | 16.08 |
| 243 | 2 | 5.0 | 0.18 | 0.05 | 0.28 | 29.96 |

TABLE 39-continued

Effect of the residence time on byproducts of the acetol to propylene glycol reaction.

| Reactor Temperature [° C.] | Pressure of Discharge [bar] | Hydrogen flowrate [L/min] | Hydrogen flowrate [(ft^3)/min] | Reactor Volume [ft^3] | Residence time [min] | Total Byproducts [wt %] |
|---|---|---|---|---|---|---|
| 244 | 4 | 2.5 | 0.09 | 0.05 | 0.56 | 41.81 |
| 242 | 4 | 5.0 | 0.18 | 0.05 | 0.28 | 11.84 |
| 240 | 4 | 10.0 | 0.35 | 0.05 | 0.14 | 12.77 |

EXAMPLE 14

Effective Hydrogenation Catalysts

Most of the experiments validating the embodiments of these inventions were demonstrated using a copper chromite catalyst. Table 40 summarizes a survey of additional catalysts for the hydrogenation of acetol to propylene glycol.

TABLE 40

Effect of the residence time on byproducts of the acetol to propylene glycol reaction. The reactions were at 185° C., 14 bars of hydrogen overpressure, and the reaction time was 4 hours.

| Supplier | Description | Acetol conversion (%) | Propylene Glycol Selectivity (%) |
|---|---|---|---|
| Grace Davison | Raney Copper | 99.07 | 91.72 |
| Degussa | 5% Palladium/Carbon | 76.22 | 74.26 |
| Sud-Chemie | Copper-Zinc a | 91.56 | 87.17 |
| Sud-Chemie | Copper/Alumina b | 82.67 | 96.91 |
| Sud-Chemie | Copper Chromium c promoted by Ba and Mn | 96.89 | 98.92 |
| Sud-Chemie | Copper Chromium d | 98.22 | 93.86 |
| Sud-Chemie | Copper Chromium promoted by Ba e | 74.22 | 95.97 |
| Engelhard | Copper Chromium promoted by Mn f | 98.00 | 96.08 |
| In-house | Copper/Silica g | 82.67 | 93.67 |
| Grace Davison | Raney Nickel | 99.56 | 98.90 |
| Degussa | 5% Platinum/Carbon | 72.89 | 88.71 |
| Johnson Matthey | 5% Ruthenium/Carbon | 100.00 | 100.00 |
| Alfa Aesar | Nickel/silica-alumina | 73.78 | 81.20 |
| Johnson Matthey | Nickel/Carbon | 90.22 | 89.16 |

Nominal Compositions (wt %):
a CuO (33), ZnO (65), Al2O3 (2)
b CuO (56), Al2O3 (34), MnO2 (10)
c CuO (45), Cr2O3 (47), MnO2 (3.5), BaO (2.7)
d CuO (50), Cr2O3 (38)
e CuO (41), Cr2O3 (46), BaO (13)
f CuO (36), Cr2O3 (33), MnO2 (3)
g 23 wt % copper on silica support

EXAMPLE 15

Applicability to Broader Reaction Mechanisms

The process that has been shown and described has been proven effective for production of acetol and propylene glycol, but is not limited to the reaction mechanisms of FIGS. 2 and 3. The process and process equipment is generally applicable to a range of reactions having similar overall mechanisms including at least four classes of such reactions in context of the discussion below.

A first class of liquid phase catalytic reaction occurs where a reactant (e.g. glycerol) distributes predominantly in a liquid phase and the reactant is converted to at least a first product (e.g. acetol) that that has a boiling point at least 20° C. lower in temperature than the reactant.

A second class of liquid phase catalytic reaction occurs where the reactant reacts in a parallel mechanism with hydrogen to form at least one alternative product (e.g. propylene glycol) where the alternative product has a boiling point that is at least 20° C. lower in temperature than the reactant. The selectivity to formation of the alternative produce(s) from this second reaction is greater than 0.5 when in the presence of hydrogen and hydrogen partial pressures in excess of 100 bars.

A third class of reaction proceeds substantially in parallel the first reaction including the reactant forming a higher molecular weight residue species that directly or indirectly reduces the effectiveness of the catalyst promoting the first reaction.

A fourth class of reaction that occurs when hydrogen is present that substantially inhibits the formation of the residue of the third reaction where the rate of formation of residue is reduced by at least 50% with the hydrogen partial pressure in 50 bars.

EXAMPLE 16

Figure 16:
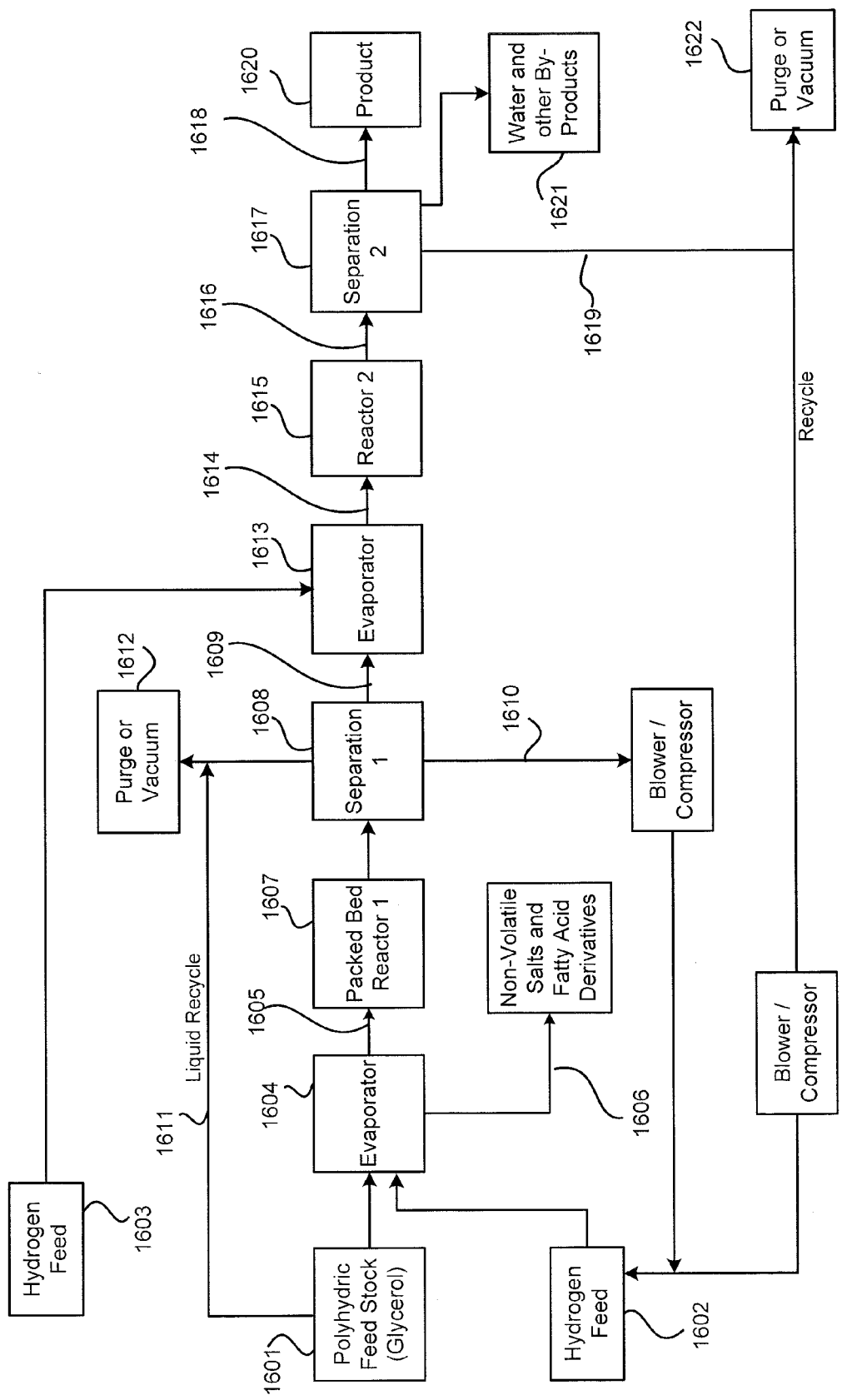
FIG. 16 is a schematic block flow diagram illustrating an improved process which includes a separation step between the reaction to generate acetol and the reaction to generate propylene glycol, as well as another separation step to obtain the end product.

Method of Producing Propylene Glycol from Glycerol with Ultra-Low Ethylene Glycol In another embodiment of the present disclosure, a separation step is included between two reaction steps which result in propylene glycol with ultra-low amount of ethylene glycol. Yet another separation step may be included after the second reaction, as illustrated in FIG. 16.

In greater details, a polyhydric feed 1601 is converted to acetol and propylene glycol in this process. A first hydrogen feed 1602 is used for a first reaction step and a second hydrogen feed 1603 is used for a second reaction step. The polyhydric feed is evaporated in an evaporator 1604 to produce a reactor feed free of liquids 1605 which contains a less than stoichiometric amount of hydrogen. This reacts in a first packed bed reactor 1607 to produce mostly acetol.

A separator 1608 sends an acetol-rich stream 1609 forward for further reaction. Gaseous materials (like hydrogen) preferably exit the separator in a recycle stream 1610 with an optional purge. Water may also be recycled and/or purged. The less volatile components like ethylene glycol and propylene glycol are separated from the acetol, with recycle 1611 preferred for the propylene glycol (and any glycerol) and purge 1612 as the ultimate and preferred destination for the ethylene glycol. Methods known in design are well known to maximize these preferred recycles and purges.

The acetol stream 1609 is preferably pumped to a higher pressure and mixed with hydrogen 1603. While a gas phase is preferred, other approaches including trickle bed reaction work well for further reaction of the acetol. Preferably, the acetol 1609 is evaporated in an evaporator 1613 in the presence of the added hydrogen 1603. The preferred liquid-free stream 1614 reacts in a reactor 1615 at conditions that favor formation of propylene glycol relative to acetol. The propylene glycol rich reaction product 1616 goes to a second separation process 1617 where unreacted hydrogen is separated into a recycle stream 1619, propylene glycol containing less than 0.05% ethylene glycol is sent forward 1618 as a product 1620. Water and other products are preferably separated as a by-product stream 1621.

A primary advantage of this process is that ethylene glycol is separated from the process in a separation process where ethylene glycol is the heavy key and acetol is the light key. Distillation is the preferred means of separation. Table 41 summarizes how, based on these key components (EG and Acetol), that the distillation separation stages and reflux is estimated by the Fenske-Underwood-Gilliland (FUG) method.

In this improved process, EG is separated from acetol, and acetol is reacted to form PG with extremely low quantities of ethylene glycol formation. The separation of ethylene glycol from propylene glycol is avoided. As compared to processes where propylene glycol is separated from ethylene glycol, much smaller columns are needed-23 stages versus 77 stages and diameters that accommodate six times less vapor flow. The reboiler duty is between one third and one fourth for this improved process as compared to processes based on separation of ethylene glycol from propylene glycol.

TABLE 41

FUG estimates of stages (N) and refluc (R) for separation of ethylene glycol (EG) from acetol as compared to separation of EG from propylene glycol (PG).
Table P1. FUG estimates of stages (N) and reflux (R) for separation of ethylene glycol (EG) form acetol as compared to separation of EG from propylene glycol (PG). Simulation is based on a feed flow of 4536 kg/h with one third of each of these components in the feed. Separation is at 1.2 bars as simulated by ChemCAD simulation software. The ethylene glycol is removed from the overhead products to 100 ppm. About 1% of the more-volatile components are in the ethylene glycol bottoms.

| Heavy | Light | $N^{min}$ | $R^{min}$ | N | R | Reboiler (MJ/h) |
|---|---|---|---|---|---|---|
| EG | PG | 35 | 2.27 | 77 | 2.72 | 9,300 |
| EG | Acetol | 10 | 0.94 | 23 | 1.13 | 2,550 |

In one embodiment of this invention first reactor 1607 conditions that favor formation of acetol and second reactor 1615 conditions that favor formation of propylene glycol are employed.

Reactions that favor formation of acetol in the first reactor 1607 are lower pressures and higher temperatures with a trace amount of hydrogen. The pressures are preferably between 0.05 and 1.2 bars and more preferably between 0.1 and 0.3 bars. Preferred temperatures are between 190 and 250° C. and more preferably between 200 and 230° C. The molar ratio of hydrogen to glycerol (preferred polyhydric feed) preferably near 0.1. Copper chromite is the preferred catalyst of this conversion.

Reactions that favor formation of propylene glycol from acetol in the second reactor 1615 are moderate pressures and lower temperatures with ample hydrogen. The pressures are preferably between 1.2 and 500 bars and more-preferably between 2 and 30 bars. Preferred temperatures are between 140 and 220° C. and more preferably between 160 and 200° C. The molar ratio of hydrogen to glycerol (preferred polyhydric feed) preferably between 1.0 and 1000 and more-preferably between 1.2 and 15. Copper chromite is a good catalyst for this conversion, but others are good and have advantages over copper chromite (such as ruthenium).

A further advantage of this process over prior art is the reduced need to recycle hydrogen. In prior gas-phase art higher hydrogen stoichiometries are need to evaporate glycerol. In the embodiments of this invention, lower pressures are used to evaporate glycerol for the first reactor. In the second reactor, acetol is considerably more-volatile than glycerol would be, and little or no hydrogen is needed for evaporation—hydrogen is optimized for conversion in the second reactor 1615 and for overall process considerations largely independent of the getting materials into the gas phase for reaction in the second reactor 1615.

During the conversion of glycerol to propylene glycol, highly selectivity conversion is necessary for commercial viability. The greatest strides in achieving high selectivity are attained with catalyst and temperature. For the conversion of glycerol to propylene glycol, these parameters can be optimized to achieve selectivities of greater than 80%.

This examples relates to the optimization of more-subtle parameters such as concentration, water content, pressure, isothermal operation, and residence time to achieve selectivities in excess of 90%. Data reveal that low concentrations are important to reduce by-products with formation reliant on second-order reaction mechanisms. Water is important to reduce dehydration reactions and indirectly helps to maintain more-isothermal operation.

Petroleum is a diverse mixture of hydrocarbons with respective chemical syntheses being highly reliant on separations for relatively non-selective conversions. In contrast, many biomass feedstocks have more-uniform chemical compositions with respective opportunities to have more-selective conversions during chemical synthesis. Glycerol is an example of a chemical that can be isolated from vegetable oils at high purity with relatively minimal processing.

Figure 17:
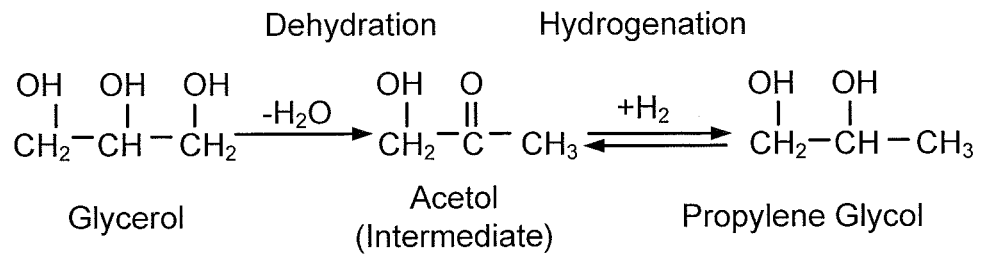
FIG. 17 is a schematic of the disclosed reaction mechanism for conversion of glycerol to propylene glycol via acetol intermediate showing also the conversion from propylene glycol back to acetol.

The chemical reaction of converting glycerol to propylene glycol (PG) is achieved through a reactive intermediate (acetol). First, glycerol is dehydrated to form acetol, and then this acetol is hydrogenated in a further reaction step to produce propylene glycol as illustrated by reaction scheme 1701 in FIG. 17.

In the formation of propylene glycol, competing reactions may exist that consume glycerol and acetol as well as subsequent reactions that consume propylene glycol. For this reaction over copper chromite at 220° C., the reaction of glycerol to propylene glycol achieves a high selectivity toward propylene glycol, while exhibiting little selectivity toward ethylene glycol and other unknown by-products at optimal conditions.

In this example and toward the objective of optimizing propylene glycol production, identification of by-product generation trends was evaluated. The impact of temperature, water concentration, and hydrogen pressure were also studied.

Figure 18:
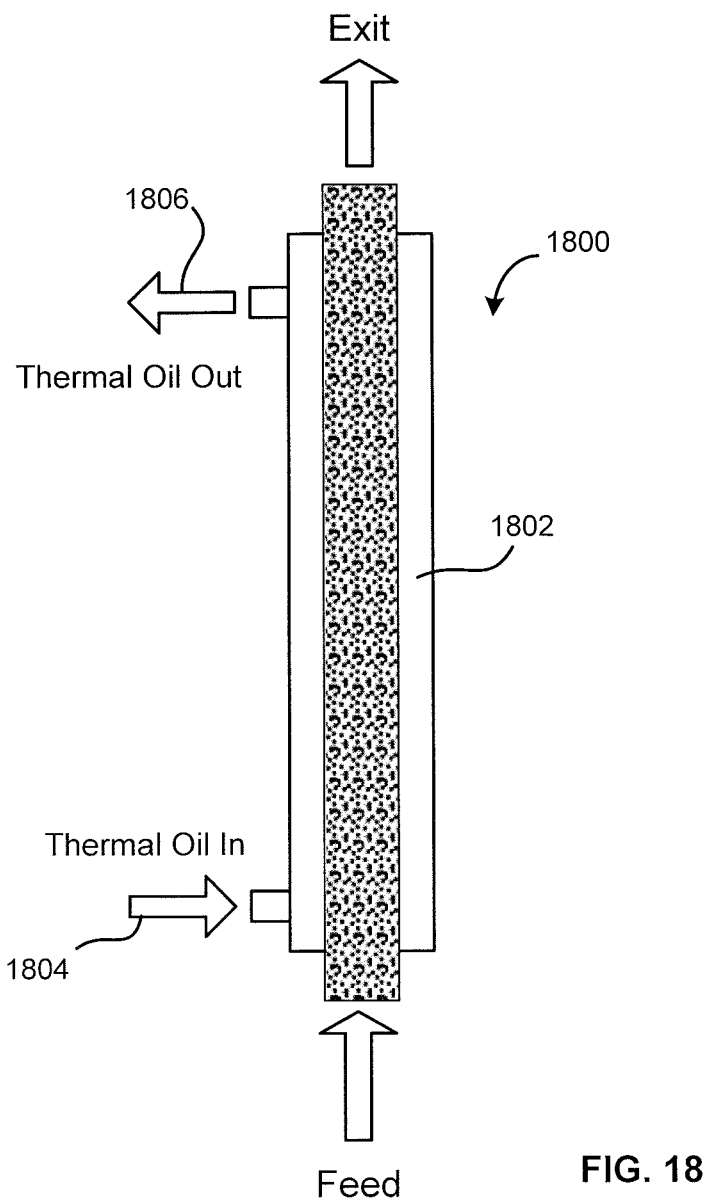
FIG. 18 shows a reactor configuration for gas phase packed bed catalysis reactions.

In more details, the packed-bed reactor for producing propylene glycol from glycerol by means of packed-bed catalytic vapor phase reaction include a catalytic reaction zone, a glycerol evaporator and a heat exchange condenser. Six hundred fifty grams of pre-reduced copper-chromite catalyst purchased from Engelhard Corporation (Elyria, Ohio) were packed in the catalytic reaction zone for producing propylene glycol as a main product. The reactor has a length of 8 ft with an outside diameter of 0.75 in equipped with thermocouples. FIG. 18 illustrates the packed-bed reactor 1800. An evaporator (not shown) precedes the reactor 1800 where the liquid reagent is evaporated while in contact with hydrogen. A condenser (not shown) after the reactors collects liquid for GC analysis. A circulating oil bath 1802 maintains the reaction temperature—either heating or cooling as necessary through thermal oil 1804, 1806.

Propylene glycol and seven unknown by-products that are present in the highest concentration were selected to carry out the study where the trends were studied in relation to propylene glycol production and reaction operating conditions. The seven unspecified by-products 8.74, 8.78, 9.11, 9.15, 9.28, 9.32, and 9.405 are named as the retention time shown in the gas chromatogram. The latest laboratory result on by-product identification indicates that the peak 9.11 was identified as ethylene glycol (EG). Factors taken into consideration in the reaction are operating pressure and temperature. The reactions were carried out at 1, 2, and 4 bar in a vapor-phase packed bed flow reactor. The reaction temperature ranges from 180 to 240° C.

To properly assess these unknown by-products, a Hewlett-Packard 6890 (Wilmington, Del.) gas chromatograph equipped with a flame ionization detector was used to analyze the finish products and collect the data. Chromatogram and area percentage data generated by the gas chromatograph were used to prepare the graphs using Microsoft Excel. Unknown by-products were compared in the ratio of internal standard (IS) and propylene glycol peak areas. All reactions were performed in the vapor-phase packed bed reactor with glycerol feed rate of 100 g/h and hydrogen flow rate of 5 l/min.

Table 42 summarizes reaction conditions and reaction conversions with the purpose of evaluating the impact of water and hydrogen on product quality. Higher product qualities have higher ratios of desired products divided by by-products. Both acetol and propylene glycol are desired products. In all cases, higher water contents provided improved ratios.

In the conversion of glycerol to propylene glycol over copper chromite catalyst the optimal yields are attached at 200-220° C. Many earlier Investigations of copper chromite in this application at higher temperatures revealed very low yields due to over-reaction. The ratio of desired products to byproducts in the absence of hydrogen reveals higher selectivities at lower temperatures.

Interestingly, at zero hydrogen flow propylene glycol is formed. It is believe that the acetol is scavenging hydrogen from glycerol to produce propylene glycol. This would also explain (in part) the higher by-products relative to reactions when hydrogen is present.

An anomaly in the data set is the comparison of product ratios at 75% glycerol at 2-3 l/m of hydrogen. In this case, the by-products ratio of desired products appears to be better at 260° C. (ratio of 3.4) than at 230° C. This anomaly can be in part be explained by experimental deviation especially with respect to hydrogen flow—the hydrogen flow meter was simply not very accurate at these low hydrogen flows (hence reported as a range of 2-3 l/min rather than a single value). In addition, at these conditions the amount of by-products are quite high. Error also accumulates when attempting to integrate tens of small by-product peaks. Conditions with these large amounts of by-product formation (ratios less than 10) may not be of commercial interest.

TABLE 42

Impact of water on reaction

| | | | Peak Area (divided by 1,000,000) | | | | |
|---|---|---|---|---|---|---|---|
| Glyc. | T in C | H2 (l/min) | Acetol | PG | EG | Total Byproducts | Ratios |
| Propylene Glycol From Glycerol | | | | | | | |
| 75% | 230 | 2-3 | 1145 | 822 | 23 | 707 | 2.8 |
| 50% | 230 | 2-3 | 844 | 435 | 15 | 162 | 7.9 |
| 25% | 230 | 2-3 | 624 | 266 | 9 | 54 | 16.4 |
| 75% | 260 | 2-3 | 1403 | 850 | 61 | 661 | 3.4 |
| 50% | 260 | 2-3 | 1305 | 430 | 27 | 308 | 5.6 |
| 100% | 230 | 5 | 927 | 737 | 18 | 283 | 5.9 |
| 75% | 230 | 5 | 826 | 646 | 14 | 209 | 7.1 |
| 50% | 230 | 5 | 680 | 474 | 10 | 115 | 10.0 |
| 25% | 230 | 5 | 515 | 357 | 10 | 54 | 16.1 |
| Acetol from Glycerol | | | | | | | |
| 75% | 230 | 0 | 1305 | 190 | 9 | 743 | 2.0 |
| 50% | 230 | 0 | 1048 | 197 | 6 | 295 | 4.2 |
| 25% | 230 | 0 | 792 | 145 | 4 | 144 | 6.5 |
| 75% | 260 | 0 | 1083 | 75 | 0 | 355 | 3.3 |
| 50% | 260 | 0 | 802 | 59 | 0 | 222 | 3.9 |

Reactions include gas phase flow through a 0.5 inch ID reactor packed with about 85 g of copper-chromite catalyst with glycerol (or acetol) feed rates of about 200 g/hr. Abbreviations include Glyc., H2, PG, and EG for glycerol, hydrogen, propylene glycol, and ethylene glycol. The percent glycerol is the percent glycerol in the liquid feed with the remainder water except with the feed was a mixture of acetol and water.

Figure 19:
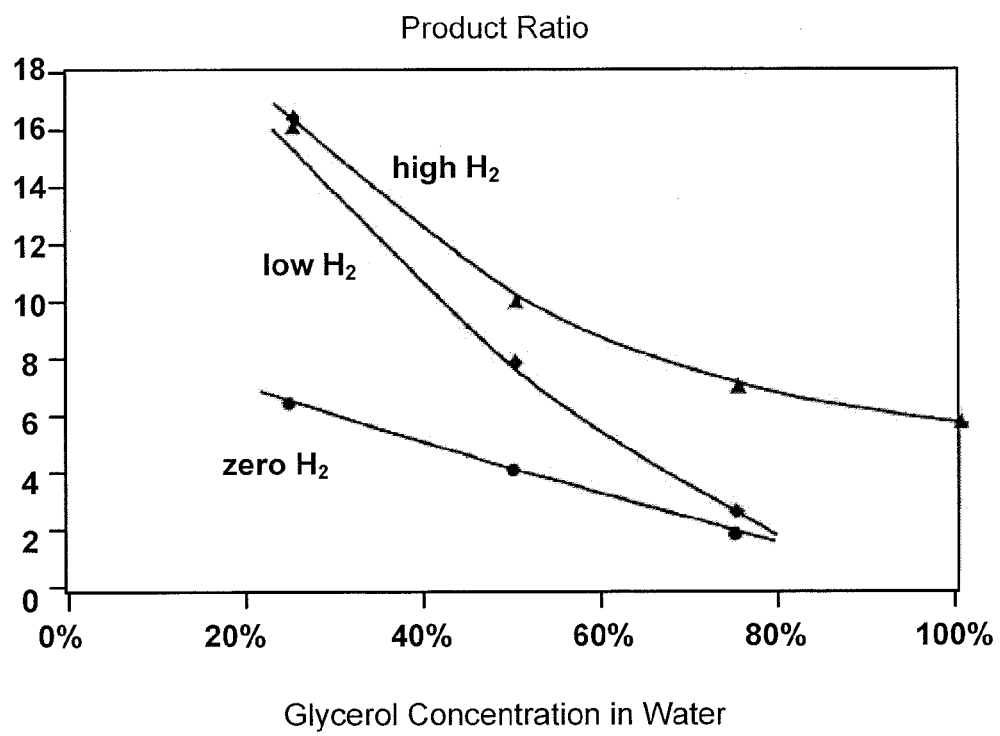
FIG. 19 shows the impact of hydrogen and water concentration on ratio of desired products to sum of undesired by-products at 230° C. The desired products are the sum of acetol and propylene glycol.

FIG. 19 readily illustrates how water improves selectivity. Higher hydrogen flow rates also improve product selectivity. At lower glycerol feed concentrations the impact of hydrogen flow is less. This is believed to be due to the sensitivity of by-product to reaction temperature. At higher temperatures more by-products form. The hydrogenolysis process is highly exothermic, and so the sensible heat of either hydrogen or water will reduce exothermic temperature increases. As more water becomes present in the feed, the secondary purpose of hydrogen as a heat moderator becomes less important.

It is also known that many of the by-products are oligomeric in nature. Oligomer-forming reaction are second order, and so, dilution with water tends to decrease their formation. It is believe that waters dilution and heat capacity contribute to reduced by-product formation.

A third mechanism for the benefits of water is related to its ability to inhibit dehydration reactions when such dehydration reactions are equilibrium limited. In the case of acetol formation, the dehydration reaction is not equilibrium limited, and so, water does not adversely impact glycerol dehydration. However, the formation of some by-products may be equilibrium limited and water could inhibit their formation, More-definitive proof of this third mechanism is not possible using these data due to waters other impact and lack of knowledge on most of the by-products.

Reactions with acetol rather than glycerol as the feed (see Table 43) add additional insight into the mechanism of by-product formation. Even at high hydrogen flow rates, when acetol is used as the feed, generation of by-products increases.

The primary difference between the runs of Tables 42 and 43 at hydrogen flow rates of 5 l/min is that acetol is present at higher concentrations for a longer time when it is used as a feed. This supports the conclusion that by-products are formed primarily from acetol substrate. The higher the average concentration of acetol present, the more by-products form.

The two conditions that result in the highest average acetol concentration during reaction are when acetol is used as the feed (Table 43) and when no hydrogen is present (last set of data in Table 42). Both of these experimental sets resulted in the lowest ratio of desired products to by-products. Acetol is more reactive, and so, being present longer (as compared to glycerol form) results in more by-product formation.

The data of Table 43 also reveal the absence of ethylene glycol formation when acetol is used as the feed. This indicates that ethylene glycol Is produced directly form reaction with glycerol as opposed to reaction with acetol or propylene glycol.

TABLE 43

Reactions at conditions similar to those of Table 42 except with acetol as the reactor feed rather than glycerol.

| | | | Peak Area (divided by 1000,000) | | | | |
|---|---|---|---|---|---|---|---|
| Glyc. | T in C. | H2 (l/min) | Acetol | PG | EG | Total Byproducts | Ratios |
| Propylene Glycol from Acetol. | | | | | | | |
| 100%* | 230 | 5 | 1399 | 2082 | 0 | 913 | 3.8 |
| 75%* | 230 | 5 | 1209 | 1554 | 0 | 581 | 4.8 |
| 50%* | 230 | 5 | 905 | 1276 | 0 | 365 | 6.0 |
| 25%* | 230 | 5 | 966 | 1305 | 0 | 322 | 7.0 |

*Indicates percent acetol in water feed.

Figure 20:
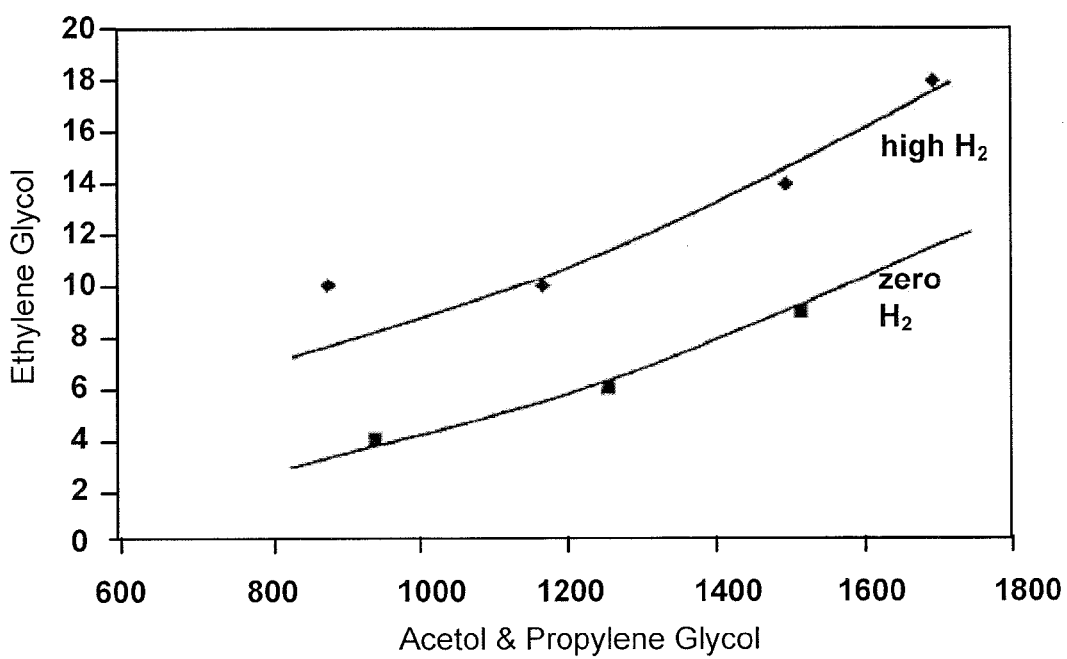
FIG. 20 shows the impact of hydrogen on ethylene glycol formation relative to formation of desired products.

Trends in ethylene glycol production are also evident in Table 42. These trends are best exemplified by the FIG. 20 plot of ethylene glycol versus the desired products. At higher hydrogen flow rates, larger relative amounts of ethylene glycol are produced. This further elucidates that ethylene glycol is likely produced from a hydrocracking reaction with glycerol. While hydrogen has a minimal impact on the rate of dehydration of glycerol to acetol, higher hydrogen pressures would specifically increase the rate of glycerol hydrocracking.

At the conditions of these reactions (1 bar) the amount of ethylene glycol being produced is quite low (less than 1%). At higher hydrogen partial pressures, others have reported ethylene glycol at 10% or higher yields. A general observation based on data beyond that present in this paper suggests that for gas phase reactions there are limited advantages to operating at pressures greater than about 20 bars due to the increased generation of ethylene glycol.

The data in Table 42 indicates that more ethylene glycol forms at lower temperatures than at higher temperatures. At come conditions the ethylene glycol was below detectable limits. While inadequate data is available to explain this trend, it is possible that at higher temperatures the ethylene glycol was formed and rapidly proceeded to react to other products including components that are considerably more volatile than ethylene glycol.

Reaction of Glycerol to Propylene Glycol

Figure 21:
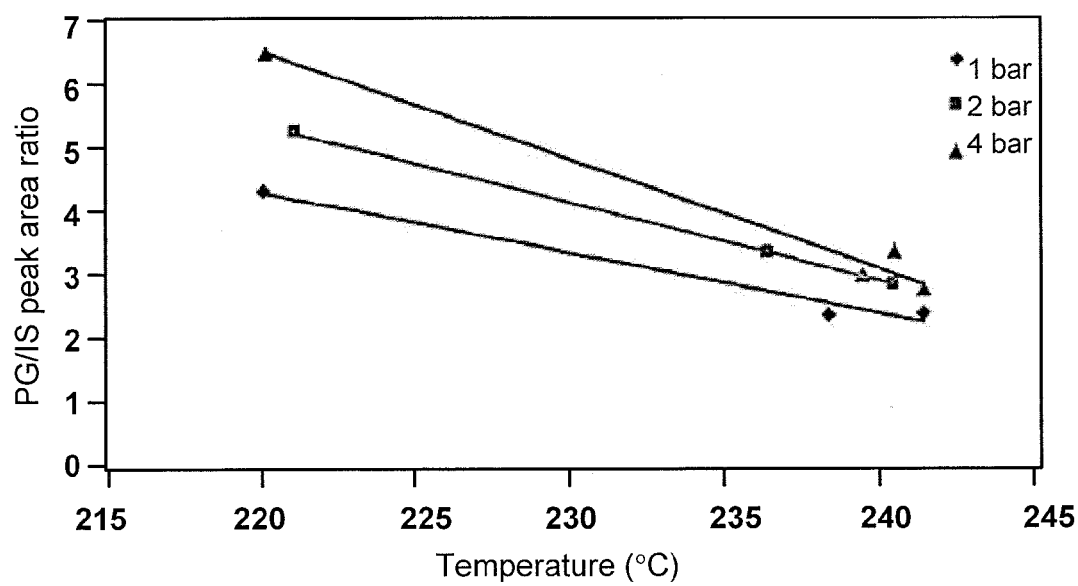
FIG. 21 shows the effect of reaction temperature and pressure on propylene glycol production from glycerol.

FIG. 21 presents the effect of temperature on production of propylene glycol from glycerol at different pressures. The results indicate that as the reaction temperature decreases from 240 to 220° C. there is an increase in the production of propylene glycol. Also, more propylene glycol was produced at higher system pressures.

Figure 22:
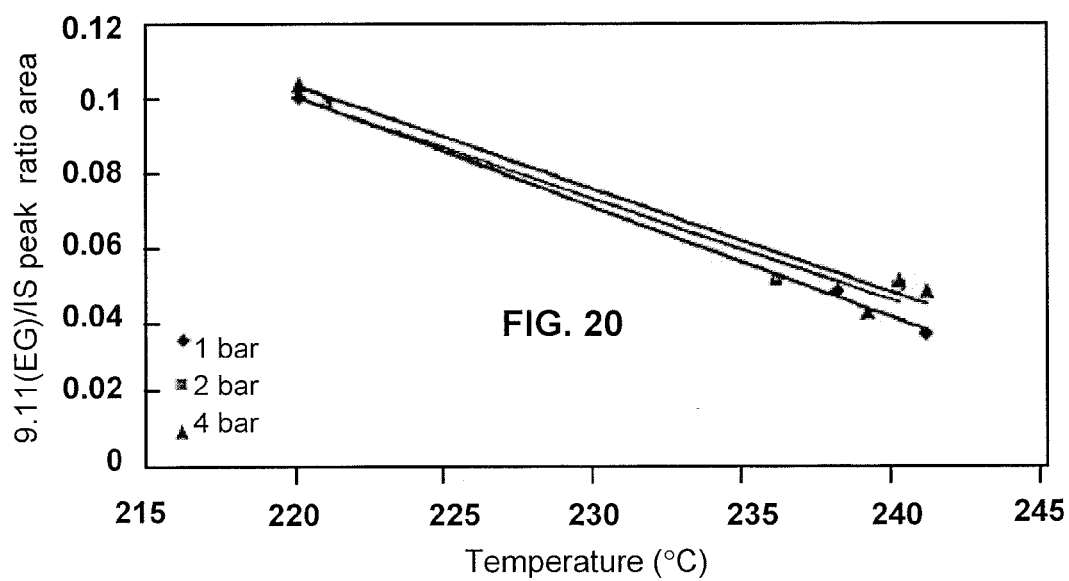
FIG. 22 shows the effect of reaction temperature and pressure on unknown by-product 9.11 (EG) formation of the glycerol to propylene glycol reaction (Data were plotted by 9.11(EG)/IS peak area ratio vs. Temperature).

It was observed that the by-product 9.11 (ethylene glycol) (see FIGS. 22 and 23) is the only by-product studied that follows the trend of propylene glycol production—the formation of ethylene glycol increases with decreasing temperature and increasing propylene glycol production. As the reaction temperature increases, there is a decrease in the formation of ethylene glycol, and more ethylene glycol is produced at higher pressures.

Figure 23:
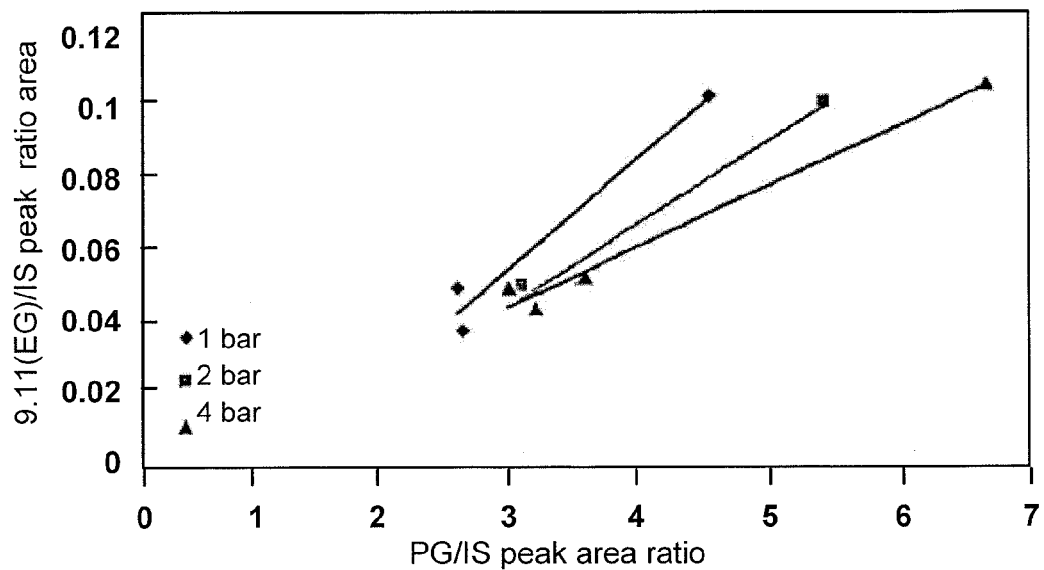
FIG. 23 shows the formation of unknown by-product 9.11 (EG) versus propylene glycol production of the glycerol to propylene glycol reaction (Data plotted by 9.11(EG)/IS peak area ratio vs. PG/IS peak area ratio).

It should be noted that that different x-axes in FIGS. 20 and 23 illustrate different trends. Higher hydrogen pressures favor the formation of ethylene glycol as compared to the sum of acetol and propylene glycol. These same higher pressures shift the equilibrium form acetol to propylene glycol, and so, over a moderate temperature range the formation of propylene glycol is favored over ethylene glycol.

For commercial production, acetol can be recycled to extinction which should be considered when identifying optimal process conditions. Also, at hydrogen pressures above about 20 bars, essentially all the acetol will be shifted to propylene glycol (at 220° C.), and so, at pressures higher than about 20 bars ethylene glycol formation will be favored over propylene glycol formation.

Reaction of Acetol to Propylene Glycol

Figure 24:
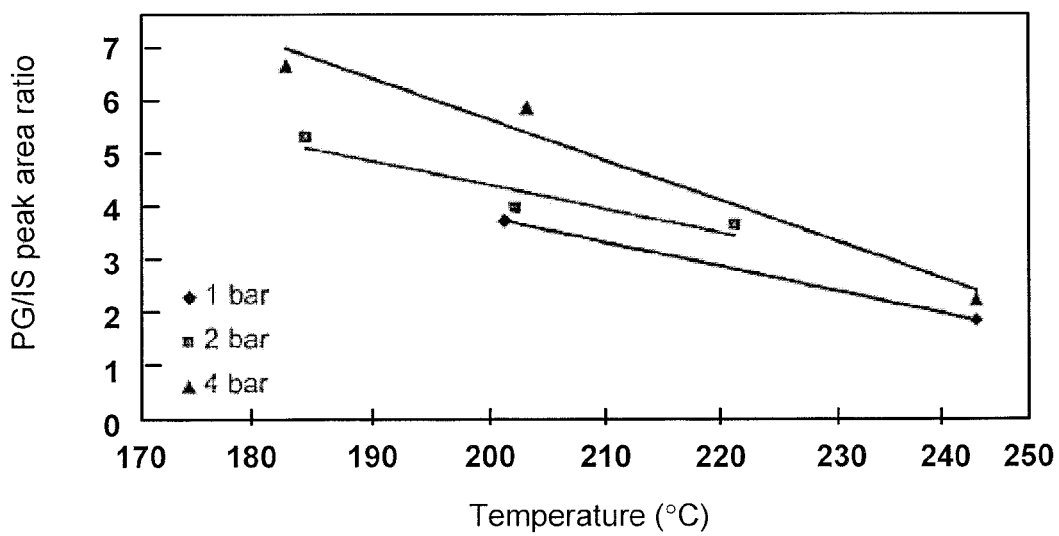
FIG. 24 shows the effect of reaction temperature and pressure on propylene glycol production from acetol.

The effect of temperature (180 to 240° C.) on the conversion of acetol to propylene glycol at three different pressures (1, 2, and 4 bar) is presented in FIG. 24. This figure indicates that more propylene glycol is produced at lower reaction temperatures, and this behavior is evident at each of the three pressure levels. It was also observed that more propylene glycol is produced at higher pressures. In the reaction of acetol to propylene glycol, more propylene glycol is produced at lower temperatures and higher pressures. The result of this reaction is similar to the reaction of glycerol to propylene glycol as presented in FIG. 21.

Figure 25:
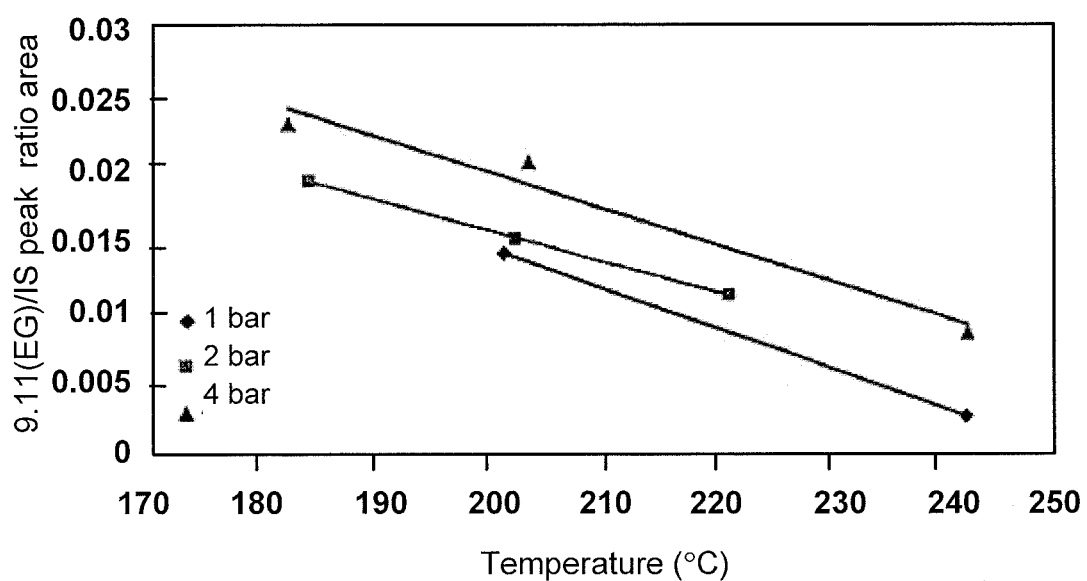
FIG. 25 shows the effect of reaction temperature and pressure on unknown by-product 9.11 formation of the acetol to propylene glycol reaction (Data were plotted by 9.11/IS peak area ratio vs. Temperature).

FIG. 25 reaffirms that at lower temperatures more ethylene glycol is formed. In this instance the reaction is with acetol substrate. The impact of higher pressures favoring more ethylene glycol formation is more pronounced in these than that for FIG. 22.

Based on the foregoing experiments, the major factors impacting by-products include but not limited to: Choice of Catalyst, Temperature of Operation, Residence Time, Too Low a Hydrogen Pressure (scavenging), Too High a Hydrogen Pressure (hydrocracking), Water (stops dehydration, controls temperature), Concentration (reduces $2^{nd}$ order mechanisms).

In conclusion, for the reactions of glycerol to propylene glycol and acetol to propylene glycol, at higher temperatures the by-product formation has a notable dependence on system pressure, in contrast, at lower temperatures the dependence of by-product formation on pressure is less. Ethylene glycol is the only by-product that follows the trend of propylene glycol production, and it is likely produced directly from glycerol.

For the overall reaction of producing propylene glycol from glycerol, lower temperature and higher pressure operation results in a higher yield in propylene glycol because of the reaction equilibrium on the second step of reaction (see Chapter 8). Concentration profiles of the by-products suggest that the preferred operating conditions for converting glycerol to propylene glycol with high selectivities are lower temperatures and higher pressures.

The process includes use in appropriate reactor configurations, such as the process equipment discussed above.

Those skilled in the art will appreciate that the foregoing discussion teaches by way of example, not by limitation. The disclosed instrumentalities set forth methods and materials by way of examples, and may not be narrowly construed to impose undue limitations on the invention. It is further recognized that the choice of chemicals and reaction conditions may be modified by one of skill in the art without departing from the spirit of this invention.

I claim:

1. A process for producing antifreeze from a crude glycerol byproduct of either a $C_1$ to $C_4$ alkyl alcohol alcoholysis of a glyceride or hydrolysis of a glyceride, the process comprising:
   neutralizing the crude glycerol byproduct to achieve a pH between 5 and 12 to form a neutralized crude glycerol byproduct;
   separating $C_1$ to $C_4$ alcohol and water from the neutralized crude glycerol byproduct such that the combined concentrations of water and $C_1$ to $C_4$ alcohols is less than about 5 (wt) %, thereby forming a separated crude glycerol byproduct; and
   contacting the separated crude glycerol byproduct with a hydrogenation catalyst and hydrogen at a pressure of between about 0.1 and 200 bar and at a temperature between about 100° C. and 290° C. for a period of time sufficient to achieve a conversion of glycerol of between 60 and 90% to form the antifreeze, which comprises, on a water-free basis, from about 0.5% to about 60% glycerol and from about 20% to about 85% propylene glycol.

2. The process according to claim 1, wherein the contacting pressure exists within a range from 1 to 20 bar.

3. The process according to claim 1 wherein the separating of $C_1$ to $C_4$ alcohol and water is achieved by flash separation at a temperature greater than about 60° C. and less than 300° C.

4. The process according to claim 1 wherein the separating of $C_1$ to $C_4$ alcohol and water is achieved by thermal diffusion.

5. The process according to claim 1, wherein the neutralizing comprises forming one or more substantially insoluble salt(s) and separating said insoluble salt(s) from the neutralized crude glycerol byproduct.

6. The process of claim 1, wherein the hydrogenation catalyst contains at least one element from Groups I or VIII of the Periodic Table.

7. The process according to claim 1 wherein the hydrogenation catalyst contains at least one metal from the group consisting of palladium, nickel, zinc, copper, platinum, rhodium, chromium, and ruthenium.

8. The process according to claim 1, wherein the neutralized crude glycerol byproduct has a pH that is from about 5 to about 9.

9. The process according to claim 1, wherein the crude glycerol byproduct comprises an acid catalyst of said $C_1$ to $C_4$ alkyl alcohol alcoholysis of a glyceride and the neutralizing comprises neutralizing said acid catalyst with a counter-ion to form a salt of the neutralized alcoholysis catalyst that is soluble in the neutralized crude glycerol byproduct.

10. The process according to claim 9, wherein, on a water-free basis, the glycerol content of the antifreeze is from about 10% to about 35% and the propylene content of the antifreeze is from about 40% to about 75%, and the antifreeze further comprises, on a water-free basis, from about 0.2% to about 10% $C_1$ to $C_4$ alkyl alcohol and from about 0.2% to about 5% of the salt of the neutralized alcoholysis catalyst.

11. The process according to claim 10 further comprising adding residue by-products of glycerol conversion reactions to the antifreeze, wherein said residue by-products are soluble in the antifreeze and constitute, on a water-free basis, from about 1% to about 15% of the antifreeze.

* * * * *